US011446056B2

(12) United States Patent
Allaway

(10) Patent No.: US 11,446,056 B2
(45) Date of Patent: *Sep. 20, 2022

(54) TRANSPERINEAL PROSTATE BIOPSY DEVICE, SYSTEMS, AND METHODS OF USE

(71) Applicant: Corbin Clinical Resources, LLC, Cumberland, MD (US)

(72) Inventor: Matthew J. Allaway, Cumberland, MD (US)

(73) Assignee: Corbin Clinical Resources, LLC, Cumberland, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 17/494,962

(22) Filed: Oct. 6, 2021

(65) Prior Publication Data
US 2022/0022996 A1    Jan. 27, 2022

Related U.S. Application Data

(63) Continuation-in-part of application No. 17/314,845, filed on May 7, 2021, now Pat. No. 11,246,677, and
(Continued)

(51) Int. Cl.
*A61B 90/00* (2016.01)
*A61B 17/34* (2006.01)
(Continued)

(52) U.S. Cl.
CPC ........ *A61B 17/3403* (2013.01); *A61B 8/0841* (2013.01); *A61B 8/12* (2013.01);
(Continued)

(58) Field of Classification Search
CPC ......... A61B 90/39; A61B 8/0841; A61B 8/12; A61B 10/0241; A61B 10/04;
(Continued)

(56) References Cited

U.S. PATENT DOCUMENTS 4,742,829 A    5/1988  Law et al.
5,494,039 A *  2/1996  Onik .................. A61B 17/3403
                                                   600/562
(Continued)

OTHER PUBLICATIONS

Canadian Office Action, CA2940211, dated Nov. 19, 2021.
(Continued)

*Primary Examiner* — Sanjay Cattungal
(74) *Attorney, Agent, or Firm* — Polsinelli PC

(57) ABSTRACT

A method of performing a transperineal biopsy procedure includes imaging the prostate with a transrectal ultrasound probe with a transperineal biopsy guide coupled to the probe. The transperineal biopsy guide including a mount coupled to the probe, a guide member coupled to the mount and including a rail receiving channel extending a first length, and a displacement member including a rail member extending a second length between a proximal end and a distal end, and a vertically extending member coupled to the distal end of the rail member. The vertically extending member including a plurality of needle receiving ports. The method further includes sliding the rail member within the rail receiving channel. The method further includes inserting an access needle into the perineal access site of the patient and inserting a needle through the access needle and into a first location of the prostate of the patient.

30 Claims, 31 Drawing Sheets

Related U.S. Application Data a continuation-in-part of application No. 16/991,150, filed on Aug. 12, 2020, said application No. 17/314,845 is a continuation of application No. 16/115,180, filed on Aug. 28, 2018, now Pat. No. 11,096,762, said application No. 16/991,150 is a continuation of application No. 14/874,104, filed on Oct. 2, 2015, now Pat. No. 10,743,909, said application No. 16/115,180 is a continuation of application No. 14/677,286, filed on Apr. 2, 2015, now Pat. No. 10,064,681, said application No. 14/874,104 is a continuation-in-part of application No. 14/677,286, filed on Apr. 2, 2015, now Pat. No. 10,064,681.

(60) Provisional application No. 61/974,826, filed on Apr. 3, 2014.

(51) Int. Cl.
| | | |
|---|---|---|
| *A61B 10/02* | (2006.01) | |
| *A61B 8/08* | (2006.01) | |
| *A61B 8/12* | (2006.01) | |
| *A61B 10/04* | (2006.01) | |
| A61B 18/02 | (2006.01) | |
| A61B 18/12 | (2006.01) | |
| A61B 17/00 | (2006.01) | |
| A61B 18/00 | (2006.01) | |

(52) U.S. Cl.
CPC .......... *A61B 10/0241* (2013.01); *A61B 10/04* (2013.01); *A61B 90/39* (2016.02); *A61B 18/02* (2013.01); *A61B 18/12* (2013.01); *A61B 2010/045* (2013.01); *A61B 2017/00274* (2013.01); *A61B 2017/00477* (2013.01); *A61B 2017/3405* (2013.01); *A61B 2017/3411* (2013.01); *A61B 2017/3413* (2013.01); *A61B 2018/00547* (2013.01); *A61B 2090/3925* (2016.02); *A61B 2090/3933* (2016.02); *A61B 2090/3954* (2016.02); *A61B 2090/3966* (2016.02)

(58) Field of Classification Search
CPC ..... A61B 17/3403; A61B 18/02; A61B 18/12; A61B 2010/045; A61B 2017/00274; A61B 2017/00477; A61B 2017/3413; A61B 2018/00547
See application file for complete search history.

(56) References Cited

U.S. PATENT DOCUMENTS

| | | | |
|---|---|---|---|
| 2003/0153850 A1* | 8/2003 | Davis | A61B 6/5235 601/2 |
| 2004/0162458 A1* | 8/2004 | Green | A61N 5/1007 600/7 |
| 2005/0159676 A1* | 7/2005 | Taylor | A61B 10/0275 600/564 |
| 2007/0043291 A1* | 2/2007 | Fidel | A61B 8/4281 600/439 |
| 2008/0004481 A1* | 1/2008 | Bax | A61N 5/1007 600/7 |
| 2009/0030339 A1* | 1/2009 | Cheng | A61B 8/4405 600/562 |
| 2011/0071380 A1* | 3/2011 | Goldenberg | A61N 5/1007 600/411 |
| 2011/0319759 A1* | 12/2011 | Liu | A61B 8/12 600/439 |
| 2012/0245455 A1* | 9/2012 | Bauman | A61B 17/3403 600/424 |
| 2013/0142875 A1* | 6/2013 | Shemi | A61B 10/0241 424/484 |
| 2014/0039314 A1* | 2/2014 | Stoianovici | A61B 8/483 600/439 |
| 2015/0119715 A1* | 4/2015 | Baumann | A61B 8/5215 600/407 |
| 2015/0366544 A1* | 12/2015 | Yap | A61B 17/3403 600/464 |
| 2020/0367925 A1 | 11/2020 | Allaway | |
| 2021/0259801 A1 | 8/2021 | Allaway | |
| 2021/0338267 A1 | 11/2021 | Allaway | |

OTHER PUBLICATIONS

U.S. Patent Litigation Document, *Complaint for Declaratory Judgment of Patent Noninfringement, Invalidity, and Violation of Georgia Law*, dated Oct. 22, 2021.

Dutch Patent Litigation Document, *Deed Submitting Reactive Exhibits (English translation of Netherlands document)*, dated Nov. 16, 2021.

Dutch Patent Litigation Document, *Summons in Interlocutory Proceedings (English translation of Netherlands document)*, dated Oct. 21, 2021.

Dutch Patent Litigation Document, *Expert Report of Dr. Rick Popert MS FRCS (UROL)*, dated Oct. 2021.

Dutch Patent Litigation Document, *Witness Statement of Saheed Rashid*, dated Oct. 15, 2021.

Dutch Patent Litigation Document, *Exhibit 19 Second Expert Report of Dr. Rick Popert MS FRCS (UROL)*, dated Nov. 15, 2021.

Dutch Patent Litigation Document, *Exhibit RP-T Ultrasound-Guided Biopsy, Chapter 4 from K. Ahrar, S. Gupta, Percutaneous Image-Guided Biopsy*, Springer 2014, pp. 39-47.

Dutch Patent Litigation Document, *Exhibit 21 Witness Statement of Dr. Matthew J. Allaway*, dated Nov. 15, 2021, 9 pgs.

Dutch Patent Litigation Document, *Exhibit MA-1 Ristau et al., Free-hand transperineal prostate biopsy provides acceptable cancer detection and minimizes risk of infection: evolving experience with a 10-sector template*, Urol Onc. 2018, 36(12).

Dutch Patent Litigation Document, *Exhibit MA-2 Emiliozzi et al., The value of a single biopsy with 12 transperineal cores for detecting prostate cancer in patients with elevated prostate specific antigen*, Journal of Urology, vol. 166, pp. 845-850, Sep. 2001.

Dutch Patent Litigation Document, *Exhibit 24 Dundee et al., Transperinealprostate biopsy: template-guided or freehand?*, BJU International 2014:681-3.

Dutch Patent Litigation Document, *Statement of Defense (English translation of Netherlands document)*, dated Nov. 2, 2021.

Dutch Patent Litigation Document, *Statement of Defense Nov. 2, 2021, Production GP15—Images of UA1232 BK Medical*.

Dutch Patent Litigation Document, *Statement of Defense Nov. 2, 2021, Production 16—Images of SureFire and UA1232 BK Medical*.

Dutch Patent Litigation Document, *Statement of Defense Nov. 2, 2021, Production GP18—Sasady WO 99/034,735 (Jul. 15, 1999)*.

Dutch Patent Litigation Document, *Statement of Defense Nov. 2, 2021, Production GP19—Transducer Type 8848 Product Data for BK Medical Ultrasound Systems*, Oct. 2011.

Dutch Patent Litigation Document, *Statement of Defense Nov. 2, 2021, Production GP20—Biplane Transducer Type 8808 User Guide BK Medical*, Jun. 2012.

Dutch Patent Litigation Document, *Statement of Defense Nov. 2, 2021, Production GP21—Biplane and Endfire Transducer Type 8818 for BK Medical Ultrasound Scanners, Product Data*, Apr. 2010.

Dutch Patent Litigation Document, *Statement of Defense Nov. 2, 2021, Production GP22—Endorectal Biplane Transducer Type 8808e for BK medical Ultrasound Scanners, Product Data*, Aug. 2010.

Dutch Patent Litigation Document, *Statement of Defense Nov. 2, 2021, Production GP23—Biplane and Endfire Transducer Type 8818 User Guide BK Medical*, Jun. 2012.

Dutch Patent Litigation Document, *Statement of Defense Nov. 2, 2021, Production GP24—Biopsy Devices and Techniques, Chapter 1 from K. Ahrar, S. Gupta, Percutaneous Image-Guided Biopsy*, Springer 2014, pp. 1-17.

(56) References Cited

OTHER PUBLICATIONS

Dutch Patent Litigation Document, *Statement of Defense Nov. 2, 2021, Production GP27—Novella et al., Pain Assessment after Original Transperineal Prostate Biopsy Using a Coaxial Needle*, Urology 62(4), 2003, pp. 689-692.

Dutch Patent Litigation Document, *Statement of Defense Nov. 2, 2021, Production GP28—Ficarra et al., Needle Core Length is a Quality Indicator of Systematic Transperineal Prostate Biopsy*, European Urology 50 (2006) 266-271.

Dutch Patent Litigation Document, *Statement of Defense Nov. 2, 2021, Production GP29—Galfano et al., Prostate Biopsy: The Transperineal Approach*, EAU-EBU Update Series 5 (2007) 241-249.

Dutch Patent Litigation Document, *Statement of Defense Nov. 2, 2021, Production GP30—Bluvol et al., Freehand Versus Guided Breast Biopsy: Comparison of Accuracy, Needle Motion, and Biopsy Time in a Tissue Model*, AJR:192, Jun. 2009, pp. 1720-1725.

Dutch Patent Litigation Document, *Statement of Defense Nov. 2, 2021, Production GP31—Chang et al., Transperineal biopsy of the prostate—is this the future?*, Nature Reviews, Urology, vol. 10, Dec. 2013, pp. 690-702.

Dutch Patent Litigation Document, *Statement of Defense Nov. 2, 2021, Production GP32—Zur Früherkennung von Prostatakrebs*, Gesundheitswesen, Oct. 2012.

Dutch Patent Litigation Document, *Statement of Defense Nov. 2, 2021, Production GP33—CareFusion Soft Tissue Biopsy Needles*, 2011.

Dutch Patent Litigation Document, *Instrument on the Production of Counter-Productions*, Nov. 23, 2021.

Dutch Patent Litigation Document, *Witness Statement from Assoc. Prof. Frantisek Zat'ura, M.D., Ph.D.*, Nov. 22, 2021.

Dutch Patent Litigation Document, *Tru-Cut Soft Tissue Biopsy Needles, Instructions for Use*, Aug. 7, 2019.

Dutch Patent Litigation Document, *Endosonic Probe User Guide Type 1850 BK Medical*, Aug. 2006.

Dutch Patent Litigation Document, *Statement from Jos J. Immerzeel MD*, Nov. 22, 2021.

Dutch Patent Litigation Document, Judgment, Feb. 3, 2022.

EP Examination Report, EP21153023.3, dated Mar. 24, 2022.

\* cited by examiner

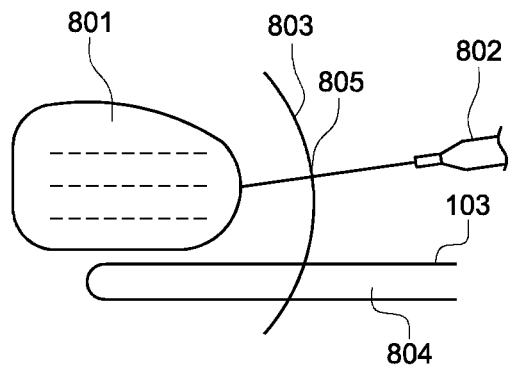
FIG. 8
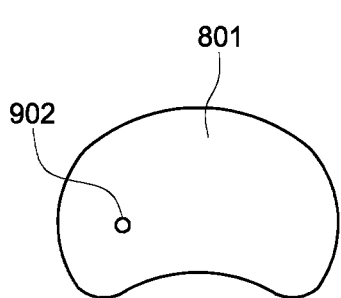
FIG. 9
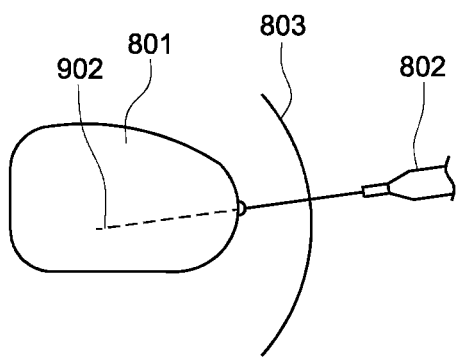
FIG. 10
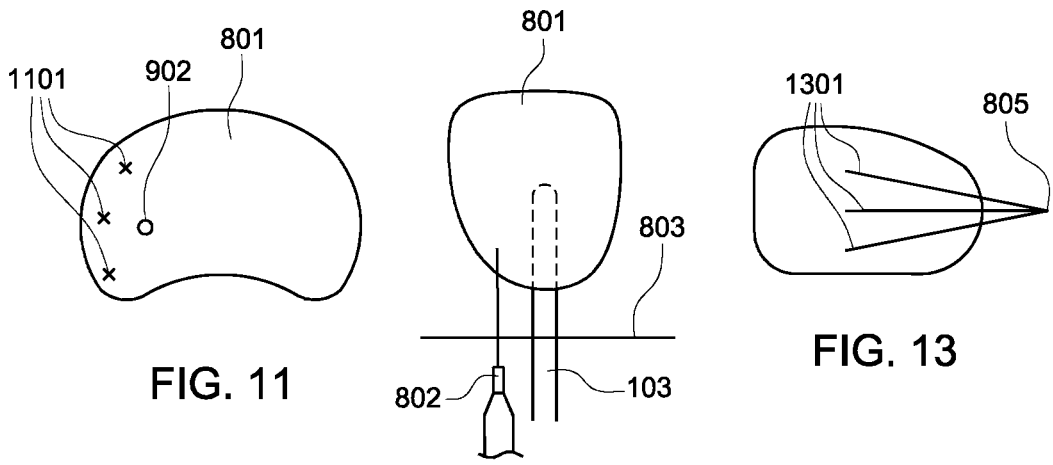
FIG. 11
FIG. 12
FIG. 13

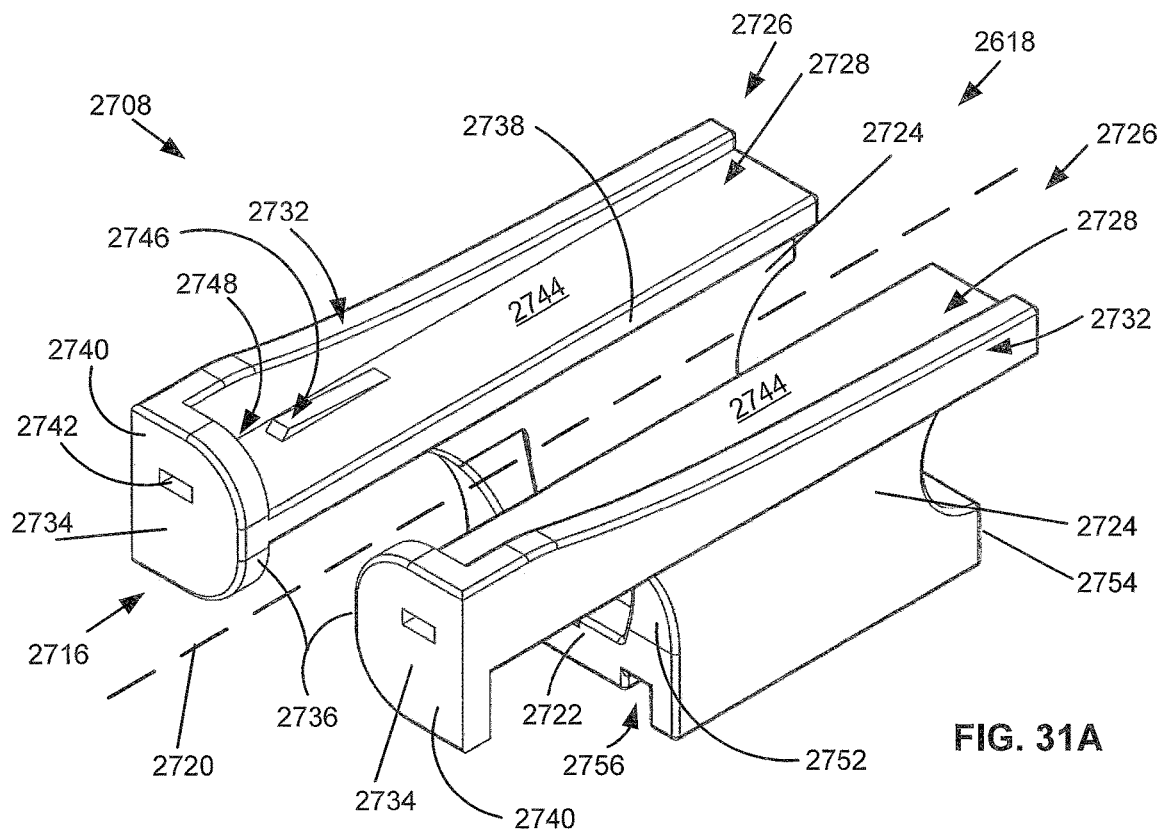
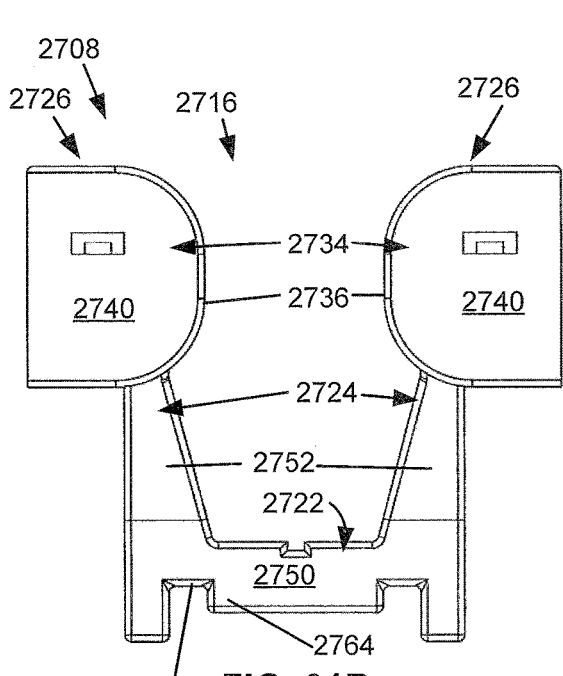 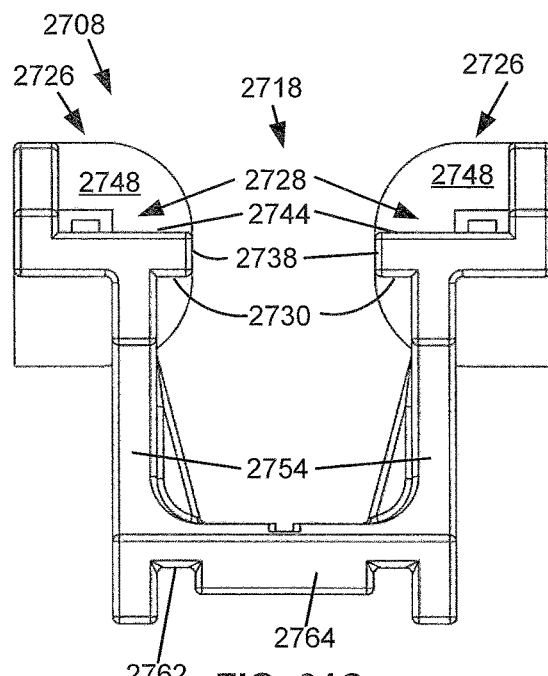
FIG. 31A
FIG. 31B
FIG. 31C

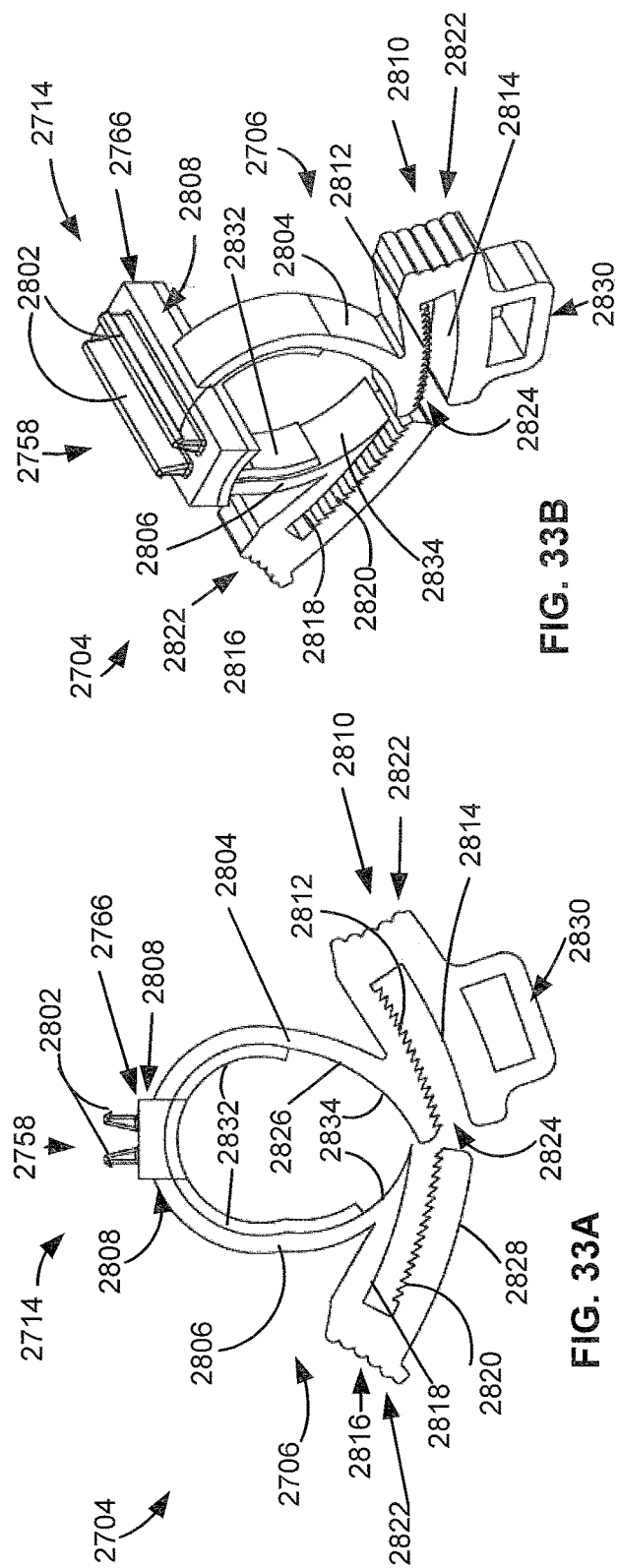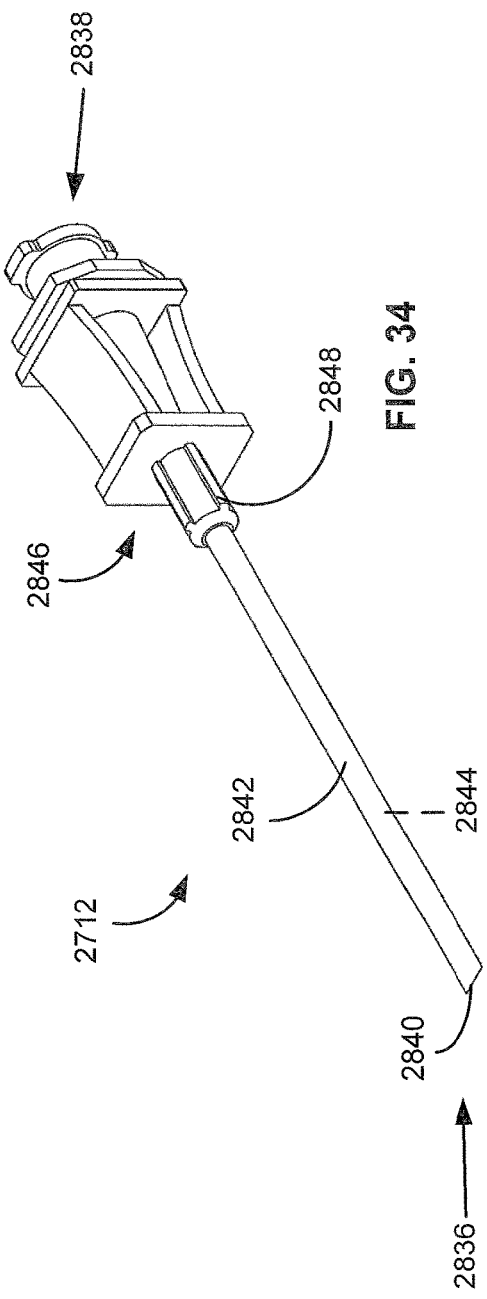

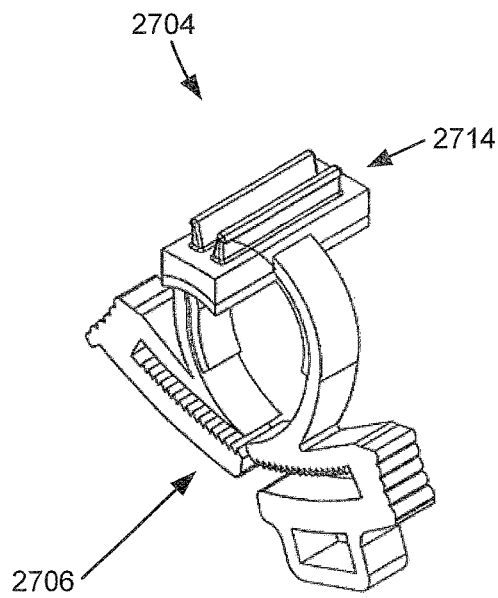
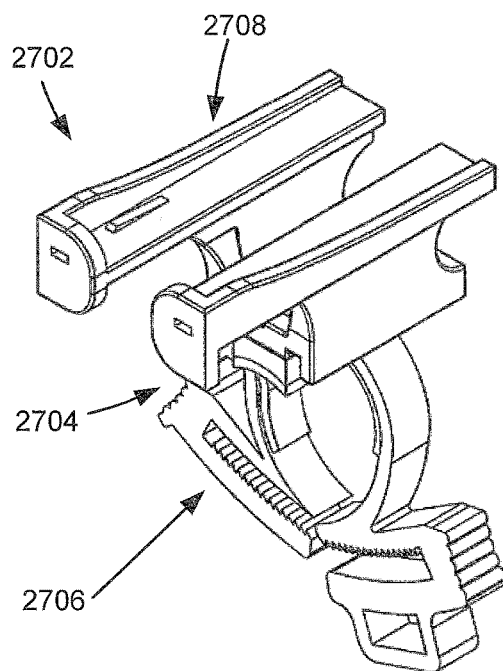
FIG. 35A    FIG. 35B
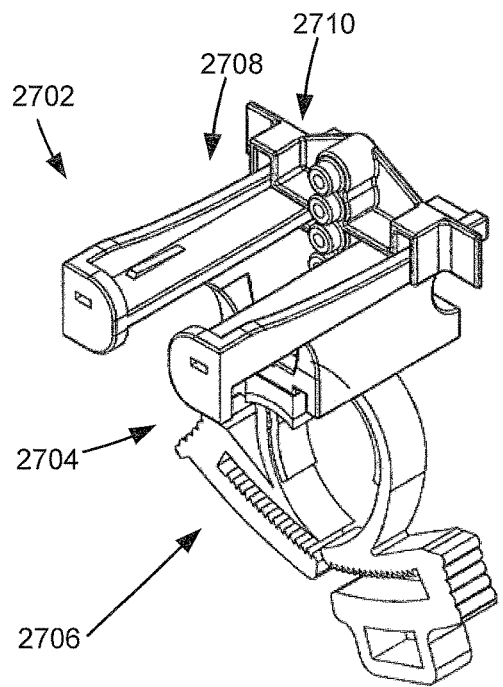
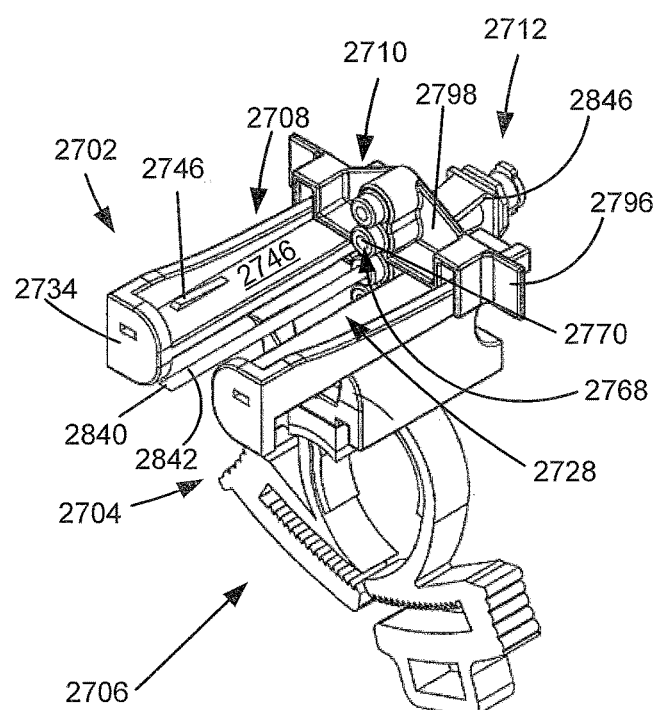
FIG. 35C    FIG. 35D

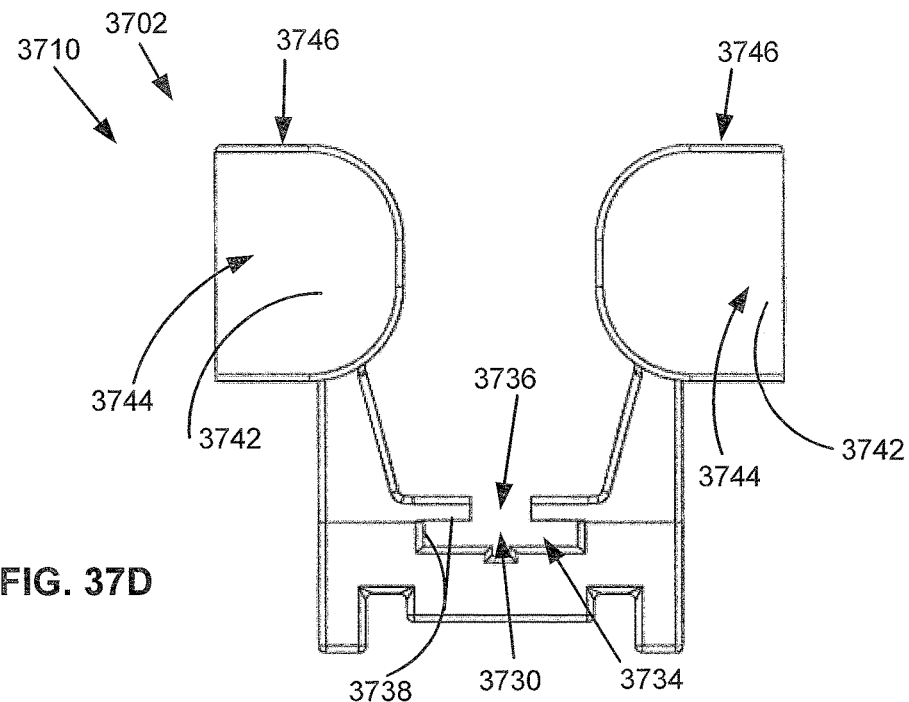
FIG. 37D
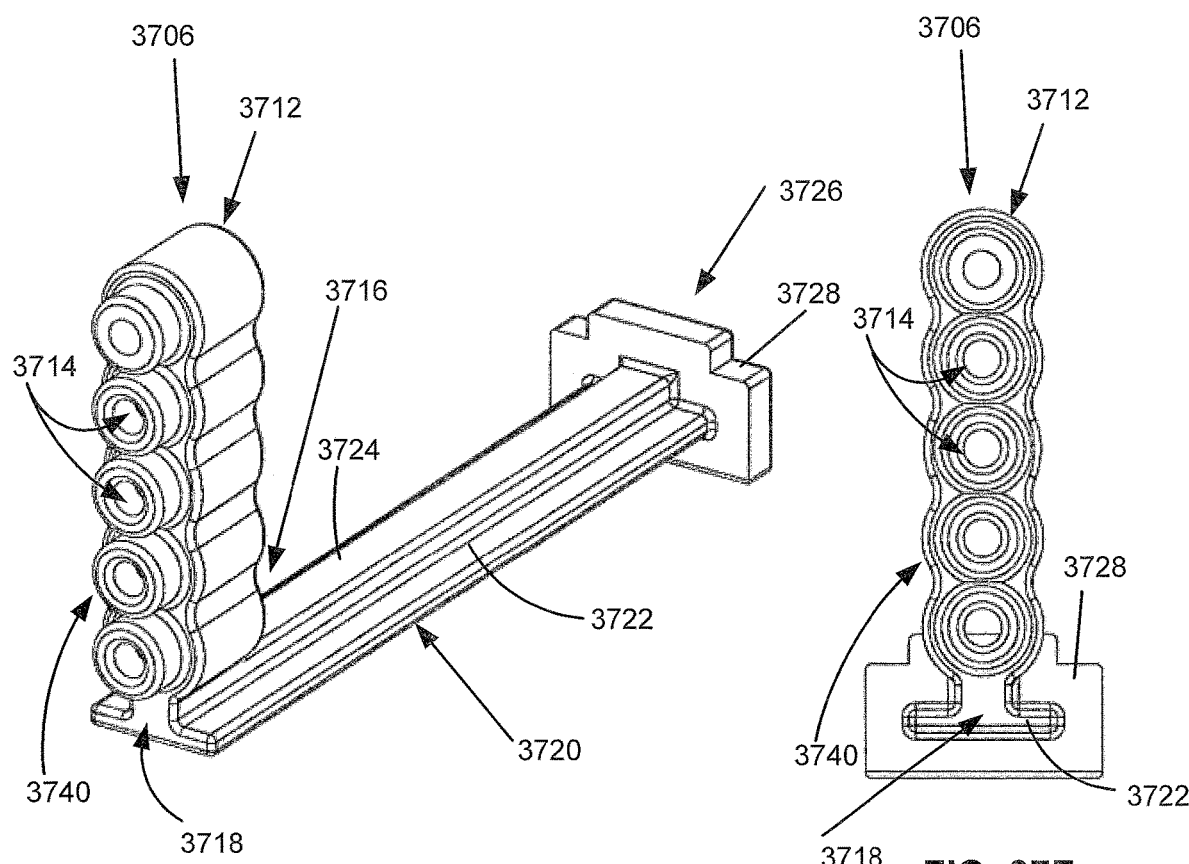
FIG. 37E
FIG. 37F

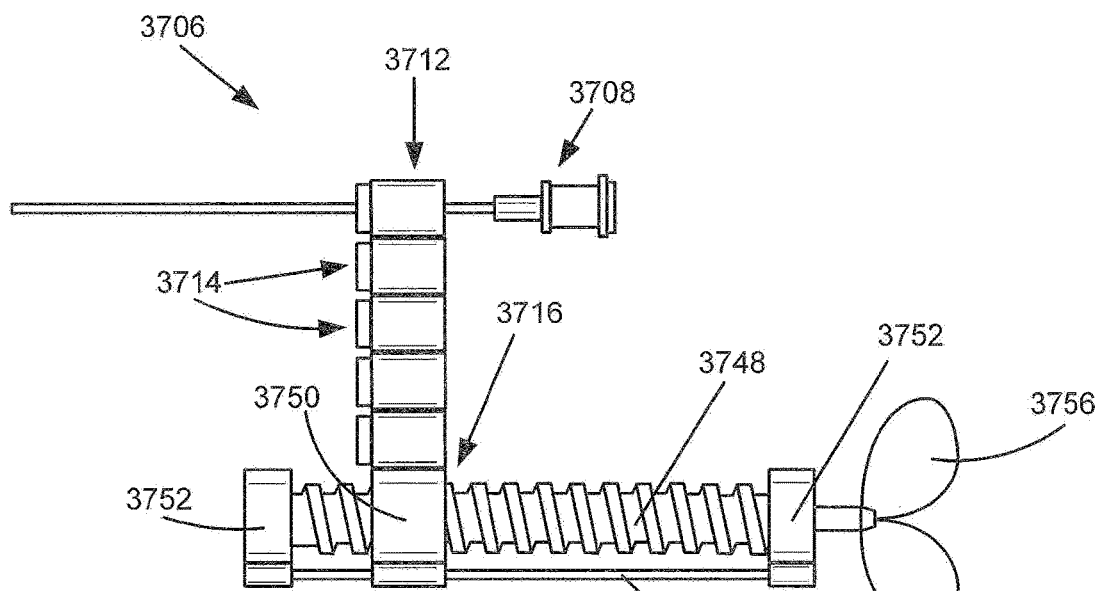
FIG. 37G
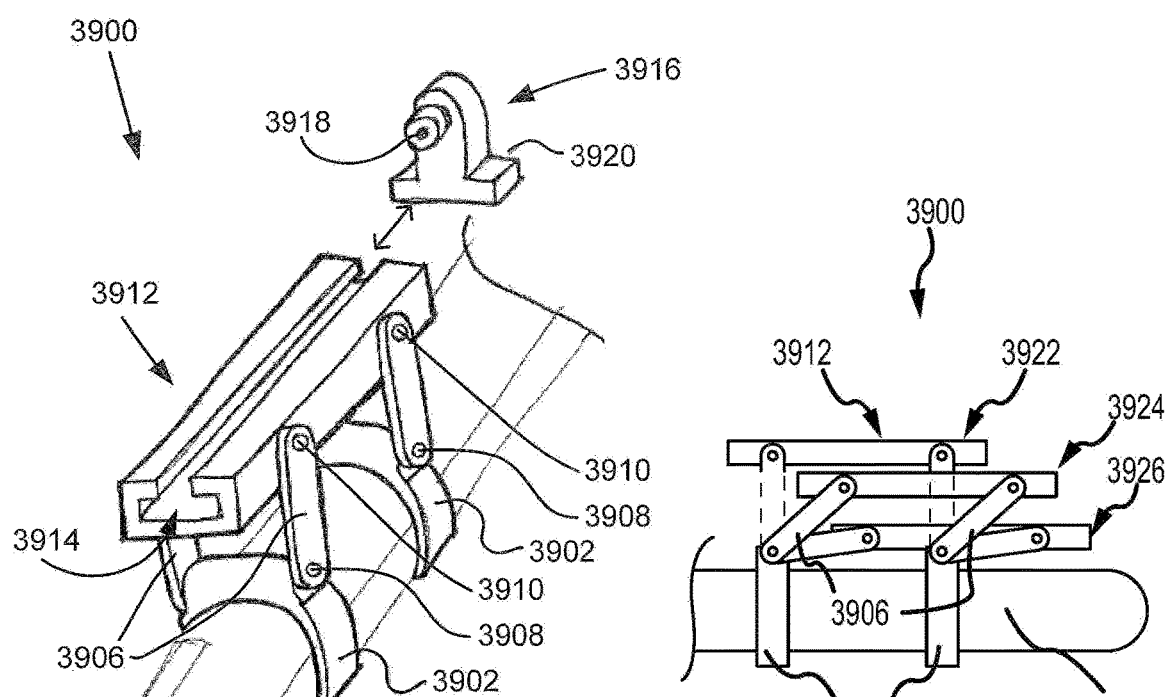
FIG. 37H
FIG. 37I

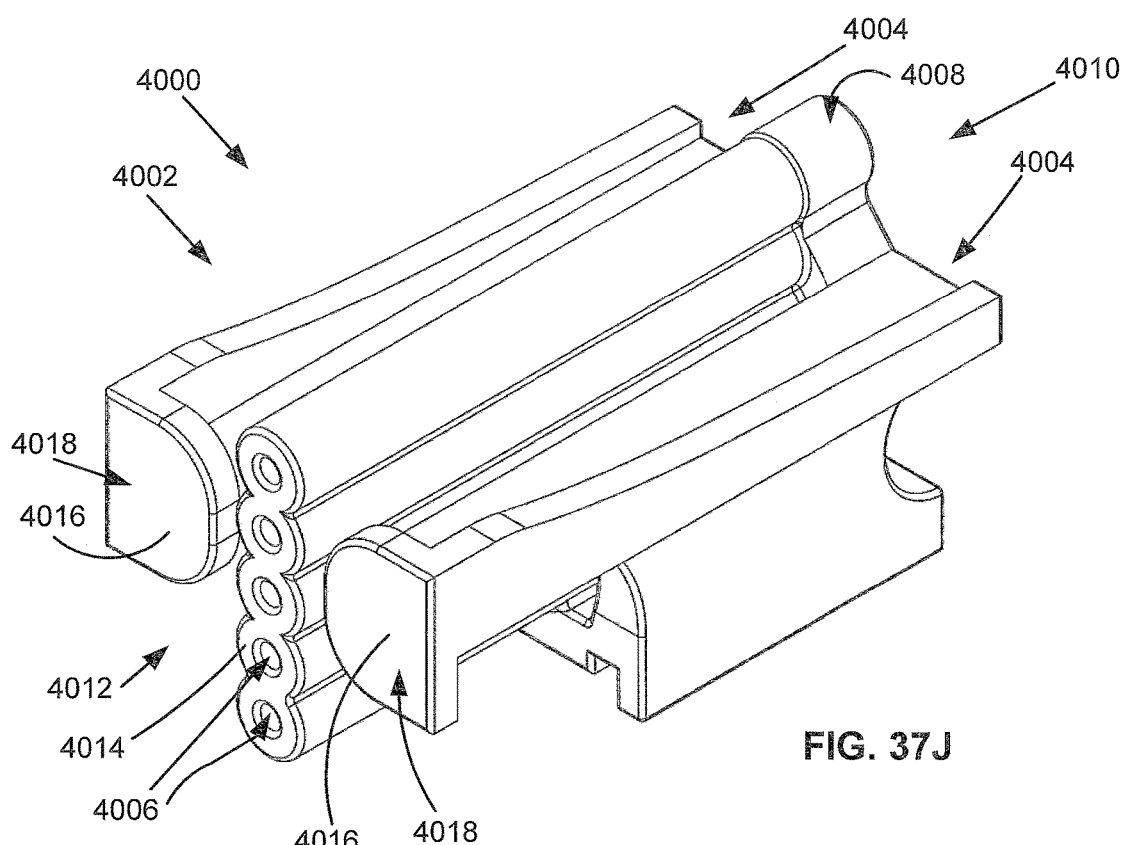
FIG. 37J
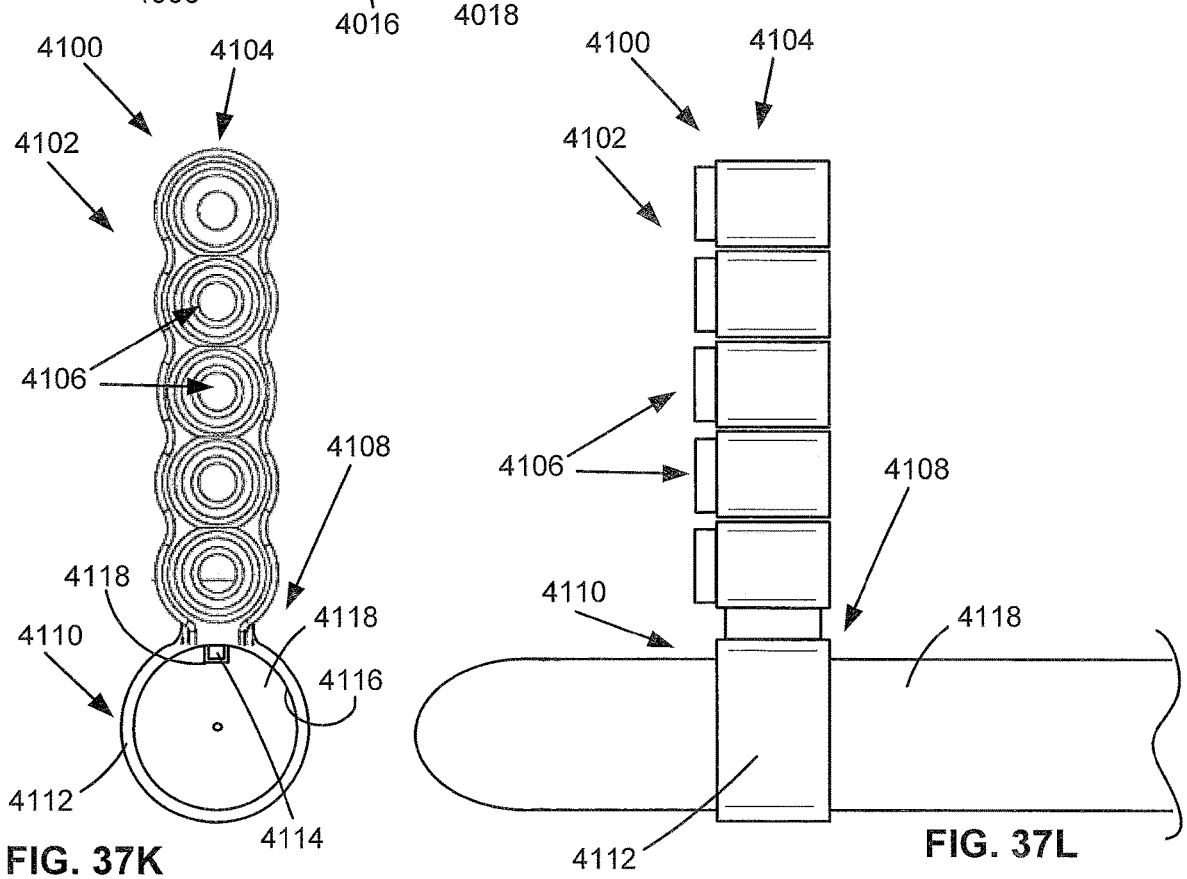
FIG. 37K
FIG. 37L

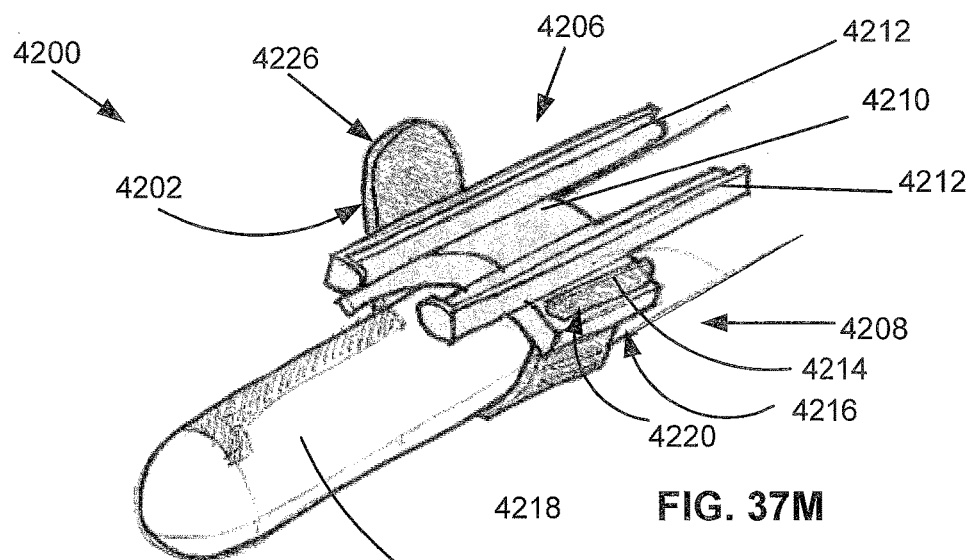
FIG. 37M
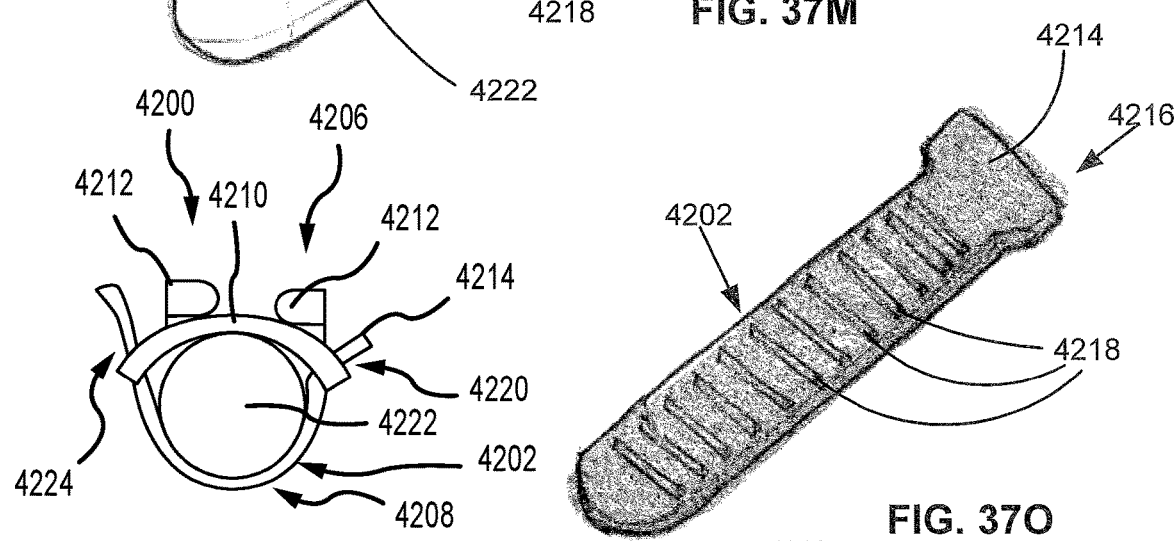
FIG.37N
FIG. 37O
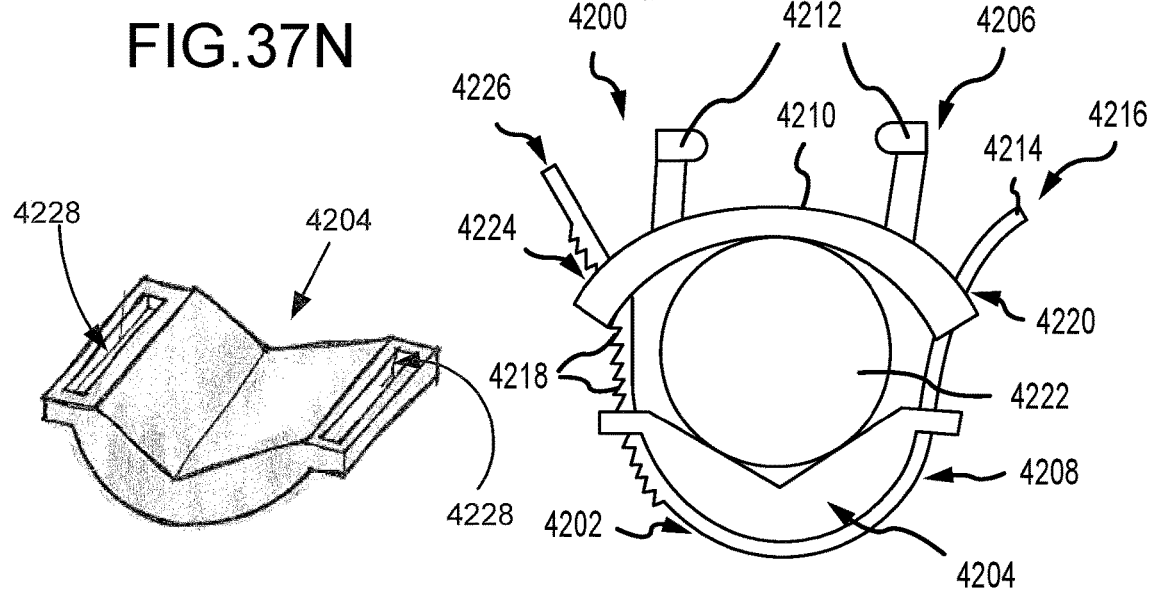
FIG. 37P
FIG.37Q

TRANSPERINEAL PROSTATE BIOPSY DEVICE, SYSTEMS, AND METHODS OF USE

CROSS-REFERENCE TO RELATED APPLICATIONS

The present application is a continuation-in-part of U.S. application Ser. No. 17/314,845 filed May 7, 2021, which application is a continuation of U.S. application Ser. No. 16/115,180 filed Aug. 28, 2018, now U.S. Pat. No. 11,096,762, which application is a continuation of U.S. application Ser. No. 14/677,286 filed Apr. 2, 2015, now U.S. Pat. No. 10,064,681, which claims priority under 35 U.S.C. § 119 to U.S. Provisional Patent Application No. 61/974,826 filed Apr. 3, 2014.

The present application is also a continuation-in-part of U.S. application Ser. No. 16/991,150 filed Aug. 12, 2020, which application is a continuation of U.S. application Ser. No. 14/874,104 filed Oct. 2, 2015, now U.S. Pat. No. 10,743,909, which application is a continuation-in-part of U.S. patent application Ser. No. 14/677,286 filed Apr. 2, 2015, now U.S. Pat. No. 10,064,681, which claims priority under 35 U.S.C. § 119 to U.S. Provisional Patent Application No. 61/974,826 filed Apr. 3, 2014.

All the above-referenced applications are hereby incorporated by reference in their entireties.

TECHNICAL FIELD

Aspects of the present disclosure relates to biopsy procedures and systems. In particular, the disclosure relates to methods, systems, and apparatus useful for planning and performing guided and free-handed transperineal prostate biopsies.

BACKGROUND

A biopsy is a medical procedure that involves sampling and removing tissues or cells from a living body for further examination and analysis. A prostate biopsy may be performed by a care provider for diagnosis and treatment of a patient's prostate. For example, the vast majority of patients with an abnormal prostate specific antigen (PSA) or suspicious results from a digital rectal examination (DRE) undergo biopsy. Typical biopsy procedures include transrectal ultrasound-guided (TRUS) biopsies and transperineal ultrasound-guided (TPUS) biopsies.

TRUS involves obtaining tissue or cell specimens by passing a biopsy needle or other biopsy instruments through the rectal wall and into the prostate at various locations using a sagittal imaging plane. The biopsy needle or other biopsy instruments may be guided by ultrasound in a sagittal plane. There are disadvantages associated with TRUS. In particular, the patient may be required to take antibiotics prior to the procedure to reduce the risk of infections. Also, TRUS requires the patient to perform bowel preparation, which is a procedure usually undertaken before the biopsy, for cleansing the intestines of fecal matter and secretions. Further, the passage of the biopsy needle through the rectal wall may introduce bacteria from the rectum into the prostate, such as coliform bacteria that may lead to an infection or other complications. Additionally, many clinically significant prostate cancers are found in locations of the prostate that are often too difficult to access when using the transrectal approach.

TPUS includes obtaining tissue or cells specimens by passing one or more biopsy needles through the perineum and into the prostate. TRUS has been favored over TPUS. Unlike TRUS, TPUS does not require a patient to take antibiotics prior to the procedure or to undergo the bowel preparation for lowering the risk of bacterial issues. Further, TPUS uses a more effective route to access the prostate and is capable of accessing target locations that may be difficult to access utilizing the transrectal approach in comparison with TRUS. In addition, the needle does not pass through the rectal wall which eliminates the risk associated with TRUS of coliform bacteria entering the prostate or the bloodstream.

Systems configured for TPUS include a biopsy grid that may be fixed to, for example, a floor, platform, or table on which the patient receiving the biopsy lies. The biopsy grid may provide multiple apertures through which a biopsy needle or other biopsy instruments may be inserted. An ultrasound probe is fixed directly to the apparatus and is used to axially guide the biopsy needle or other instruments, for example other biopsy instruments. Thus, TPUS systems require imaging in an axial plane of the ultrasound or a transverse transducer for positioning the biopsy needle.

It is with these observations in mind, among others, that various aspects of the present disclosure were conceived and developed.

SUMMARY

Aspects of the present disclosure involve a biopsy guide configured to couple with a transrectal probe and for use in guiding an access needle in a transperineal prostate biopsy procedure. The access needle may be configured to perforate and be positioned within subcutaneous tissue of a perineum at an access site of a target area of a patient. The biopsy guide may include a guide member and a displacement member supported by the guide member. The guide member may be configured to operably couple with the transrectal probe and including a distal end, a proximal end opposite the distal end, and a length extending along a longitudinal axis between the distal and proximal ends. The displacement member may be configured to support the access needle and displace the access needle along at least a portion of the length of the guide member between the distal and proximal ends. The access needle may be configured to extend into the subcutaneous tissue when the access needle is displaced to the distal end.

In certain embodiments, the biopsy guide may further include the access needle.

In certain embodiments, the biopsy guide may further include the transrectal probe.

In certain embodiments, the displacement member may be configured to displace along the at least a portion of the length of the guide member between the distal and proximal ends. In certain embodiments, the guide member may include a guide rail extending at least a portion of the length between the distal and proximal ends, and the displacement member may include a coupling mechanism to releasably couple with the guide member. In certain embodiments, the displacement member may be configured to displace relative to the guide member via interaction of the coupling mechanism and the guide rail.

In certain embodiments, the displacement member may be configured to slidingly displace relative to the guide member via interaction of the coupling mechanism and the guide rail.

In certain embodiments, the guide rail may include a first guide rail and a second guide rail opposed to the first guide rail, the displacement member releasably coupled between the first and the second guide rails.

In certain embodiments, the coupling mechanism may include: first upper and lower members which may be configured to sandwich the first guide rail; and second upper and lower members which may be configured to sandwich the second guide rail.

In certain embodiments, the coupling mechanism may include upper and lower members which may be configured to sandwich the guide rail.

In certain embodiments, the displacement member may include a plurality of needle receiving ports for positioning the access needle in a plurality of orientations relative to the transrectal probe. In certain embodiments, each of the plurality of needle receiving ports may be configured to align the access needle parallel with a longitudinal axis of the transrectal probe. In certain embodiments, the plurality of needle receiving ports may include five needle receiving ports.

In certain embodiments, the biopsy guide may include a lower mount releasably coupled to the guide member and including a probe coupling mechanism for releasably coupling with the transrectal probe.

In certain embodiments, the probe coupling mechanism extends at least partially around the transrectal probe, wherein the guide rail extends distally beyond the probe coupling mechanism.

In certain embodiments, the probe coupling mechanism extends at least partially around the transrectal probe, wherein the displacement member may be configured to distally displace beyond the probe coupling mechanism.

In certain embodiments, the guide member may include a slot extending a first length between the distal and proximal ends, the displacement member including a rail member may be configured to be received within the slot such that the displacement member is displaceable along the at least a portion of the length of the guide member between the distal and proximal ends. In certain embodiments, a longitudinal axis of the slot is generally parallel with a longitudinal axis of the transrectal probe when the guide member is secured to the transrectal probe. In certain embodiments, interaction between the slot and the rail member constrains lateral movement of the displacement member relative to the guide member. In certain embodiments, interaction between the slot and the rail member constrains the vertical tilting of the displacement member relative to the guide member. In certain embodiments, the displacement member may include a plurality of needle receiving ports oriented vertically or in a single plane relative to each other. In certain embodiments, the guide member may include a pair of guide rails, the displacement member may be configured to displace between the pair of guide rails.

In certain embodiments, the access needle may extend beyond the distal end of the guide member when the access needle is displaced to the distal end. In certain embodiments, the access needle may be configured to be locked into position at the distal end.

Aspects of the present disclosure may also involve a biopsy guide which may be configured to couple with a transrectal probe and for use in guiding an access needle in a transperineal prostate biopsy procedure. The access needle may be configured to perforate and be positioned within subcutaneous tissue of a perineum at an access site of a target area of a patient. The biopsy guide may include a guide member and a displacement member. The guide member may be configured to operably couple with the transrectal probe and may include a distal end, a proximal end opposite the distal end, and a length between the distal and proximal ends. The displacement member may be supported by the guide member and may be configured to support and displace the access needle along at least a portion of the length of the guide member between the distal and proximal ends while maintaining a fixed trajectory of the access needle.

In certain embodiments, may include the transrectal probe.

In certain embodiments, may include the access needle.

In certain embodiments, the displacement member may slidingly couple with the guide member via a coupling mechanism such that the displacement member is displaceable relative to the guide member. In certain embodiments, the guide member may include a first rail member, and the coupling mechanism may include upper and lower members that sandwich the first rail member. In certain embodiments, the guide member may further include a second rail member opposite the first rail member, the upper and lower members sandwiching the second rail member. In certain embodiments, the fixed trajectory is generally parallel to a longitudinal axis of the transrectal probe. In certain embodiments, the guide member may include a pair of guide rails extending the length, and the displacement member may be positioned between the pair of guide rails and slidingly couple with the pair of guide rails via a coupling mechanism. In certain embodiments, the coupling mechanism may include upper and lower members that sandwich each of the pair of guide rails.

In certain embodiments, the guide member may include a sheath in which the probe resides when the guide member is operably coupled with the transrectal probe.

In certain embodiments, the biopsy guide further includes a mechanical arrangement between the guide member and the displacement member that at least facilitates the displacement of the access needle along the at least a portion of the length of the guide member, wherein the mechanical arrangement may include at least one of a sliding arrangement, a lead screw, or a parallel bar linkage.

In certain embodiments, the guide member operably couples with the transrectal probe via at least one of a sheath arrangement, a ratchet arrangement, a biased collar arrangement, a flexible strap arrangement, a clamping arrangement, or a clamshell collar arrangement.

Aspects of the present disclosure also involve a biopsy guide which may be configured to couple with a transrectal probe and for use in guiding an access needle in a transperineal prostate biopsy procedure. The access needle may be configured to perforate and be positioned within subcutaneous tissue of a perineum at an access site of a target area of a patient. The transrectal probe may include a distal end, a proximal end opposite the distal end, and a longitudinal axis between the distal and proximal ends. The biopsy guide may include a displacement member which may be configured to be operably coupled with the transrectal probe and to support and displace the access needle along at least a portion of the transrectal probe. The displacement of the access needle may be along a trajectory that is parallel to the longitudinal axis of the transrectal probe.

In certain embodiments, the biopsy guide may further include a guide member operably coupled to the displacement member and by which the displacement member is operably coupled with the transrectal probe.

In certain embodiments, at least a portion of the displacement member displaces relative to the guide member when the access needle is displaced along the trajectory that is parallel to the longitudinal axis of the transrectal probe.

In certain embodiments, the biopsy guide may further include a mechanical arrangement between the guide member and the displacement member that at least facilitates the displacement of the access needle along the trajectory that is parallel to the longitudinal axis of the transrectal probe, wherein the mechanical arrangement may include at least one of a sliding arrangement, a lead screw, or a parallel bar linkage.

In certain embodiments, the guide member may operably couple with the transrectal probe via at least one of a sheath arrangement, a ratchet arrangement, a biased collar arrangement, a flexible strap arrangement, a clamping arrangement, or a clamshell collar arrangement.

In certain embodiments, the biopsy guide may further include a mechanical interface by which the displacement member is operably coupled with the transrectal probe and by which the displacement member displaces the access needle along the trajectory that is parallel to the longitudinal axis of the transrectal probe. In certain embodiments, the mechanical interface may include at least one of a sliding arrangement directly between the transrectal probe and the displacement member or a rolling arrangement directly between the transrectal probe and the displacement member.

In certain embodiments, the biopsy guide may further include the transrectal probe and wherein the transrectal probe may include a first portion of the sliding arrangement and the displacement member may include a second portion of the sliding arrangement directly engaged in sliding contact with the first portion. In certain embodiments, at least one of the first portion or second portion comprises a slot, a rail, or a bar.

In certain embodiments, the biopsy guide may further include the transrectal probe and wherein the sliding arrangement may include at least a portion of the displacement member being in direct sliding contact with an exterior surface of the transrectal probe.

In certain embodiments, the biopsy guide may further include the transrectal probe and wherein the rolling arrangement may include a roller bearing arrangement supported on the displacement member being in direct rolling contact with an exterior surface of the transrectal probe.

Related art systems and prostate biopsy TPUS methods do not allow free-hand movement of the ultrasound probe, and heavily rely on the axial ultrasound plane to confirm positioning of the biopsy needle or other instruments. Moreover, such systems and methods include extracting prostate tissue specimens by delivering separate punctures into the transperineal tissue. Also, a care provider executing TPUS procedure using related art systems may experience substantial difficulty in freely handling and positioning a biopsy needle at a desired target location of the prostate relying on the sagittal plane in using the TRUS methods.

An apparatus in accordance with an embodiment may include an upper mount and a lower mount. The lower mount may be configured to connect with the upper mount to secure a transrectal probe therebetween. The upper mount may be configured to support an access needle, the access needle configured for perforation of subcutaneous tissue of a perineum at an access site of a target area of a patient. The upper mount may be configured to guide the access needle whereby movement of the access needle is fixed relative to movement of the transrectal probe.

A system in accordance with an embodiment may include a biopsy guide and a transrectal transducer fixed to the biopsy guide. The biopsy guide may be configured to guide an access needle to perforate an access site in subcutaneous tissue of a perineum, whereby movement of the access needle is fixed relative to a movement of the transrectal transducer.

A method of performing a prostate biopsy in accordance with an embodiment may include imaging a prostate in an axial plane and a sagittal plane with a transducer providing a real-time image, locating a target area of the prostate, and positioning an access needle and an access site in subcutaneous tissue of a perineum wherein the access site is at a midpoint between a lateral edge of the prostate and a urethra along a first axis and a midpoint between an anterior capsule and a posterior capsule along a second axis. The method may include guiding a biopsy instrument along a sagittal plane to the target using the real-time image, and obtaining one or more specimens of the prostate through the access needle with a biopsy instrument.

Accordingly, there is a demand for transperineal biopsy methods, systems, and apparatus that enables a biopsy that is less burdensome for the patient and for the practitioner performing the biopsy, increased guidance of needle or other biopsy instruments, and with a higher rate of efficacy and lower rate of health risk than related art TPUS and TRUS systems and methods. Apparatus, systems, and methods disclosed herein satisfy these demands.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

BRIEF DESCRIPTION OF THE DRAWINGS

FIG. 8 is a side view of a biopsy instrument that has penetrated the prostate in accordance with an embodiment;

FIG. 9 is a front view of a designated area of the prostate where a biopsy instrument will penetrate in accordance with an embodiment;

FIG. 10 is a side view of a biopsy instrument penetrating the prostate in accordance with an embodiment;

FIG. 11 is a front view of a designated area of the prostate where a biopsy instrument will penetrate with areas in which the cell or tissue specimen has already been extracted in accordance with an embodiment;

FIG. 12 is a top view of a biopsy instrument that has penetrated the prostate in accordance with an embodiment;

FIG. 13 is a side view of a prostate and the path of the biopsy instrument;

FIG. 31A is a front isometric view of the upper mount of the biopsy guide;

FIG. 31B is a front view of the upper mount of the biopsy guide;

FIG. 31C is a back view of the upper mount of the biopsy guide;

FIG. 33A is an isometric front view of the lower mount of the biopsy guide;

FIG. 33B is a front view of the lower mount;

FIG. 34 is front isometric view of an access needle;

FIG. 35A is a front isometric view of the lower mount;

FIG. 35B is a front isometric view of the lower mount coupled with the upper mount;

FIG. 35C is a front isometric view of the lower mount coupled with the upper mount and the sliding platform engaging with the rails of the upper mount;

FIG. 35D is a front isometric view of the assembly of FIG. 35C with an access needle supported by the sliding platform;

FIG. 37D is a front view of the upper mount of the biopsy guide;

FIG. 37E is a front isometric view of the displacement member of the biopsy guide;

FIG. 37F is a front view of the displacement member;

FIG. 37G is a side view of another embodiment of the displacement member with the access needle partially positioned within the top needle receiving port of the vertically extending member;

FIG. 37H is a front isometric view of another embodiment of the a biopsy guide;

FIG. 37I is a side view of the biopsy guide of FIG. 37H showing the platform member in various positions relative to the probe;

FIG. 37J is a front isometric view of another embodiment of an upper mount;

FIG. 37K is a front view of another embodiment of a biopsy guide;

FIG. 37L is a side view of the biopsy guide of FIG. 37K;

FIG. 37M is a front isometric view of another embodiment of a biopsy guide;

FIG. 37N is a front view of the biopsy guide of FIG. 37M;

FIG. 37O is a front isometric view of a cinch strap;

FIG. 37P is a front isometric view of a V-block insert;

FIG. 37Q is a front isometric view of the biopsy guide of FIG. 37M with a V-block insert of FIG. 37P;

DETAILED DESCRIPTION

Figure 1:
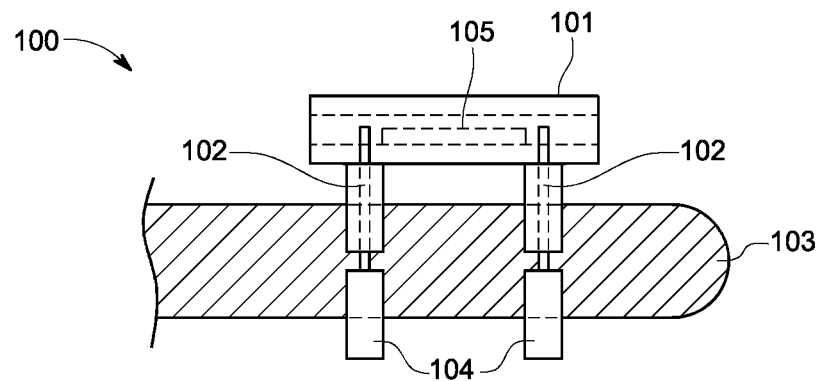
FIG. 1 shows a side view of a guide secured to a probe in accordance with an embodiment.

The apparatus, systems, and methods provided herein enable real-time visualization, free-handed, guided, and multi-sample transperineal methods for performing a biopsy. The methods, systems, and apparatus provided herein also enable a complete biopsy of the prostate with only one perforation, or with minimal perforations of a patient's skin by way of an initial access site, such that the access needle is freely moveable. The biopsy guide may be placed on or fitted to an assortment of ultrasound probes of different sizes and shapes due to an adjustable mounting system. The guide may be configured to fit to the probe using any suitably configured fastening system. For example, the guide may be configured as a sleeve that is formed to slide over an end of a probe and into an operable position. Alternatively, the guide may be configured to fit to a probe using screws, flanges, zip ties, or other temporary, permanent, or semi-permanent fastening systems.

In one embodiment, the guide allows biopsies of one or more tissue or cell samples to be obtained through an initial access needle, while providing direct, real-time ultrasound visualization by, for instance, fixing a position of the access needle relative to an ultrasound probe to provide. For example, the guide is fixed to an ultrasound probe that is not fixed and may be freely moveable in operation. Stabilization bars that are built into the guide facilitate the positioning and holding of the perineal skin and subcutaneous tissue to allow positioning of the access needle. The position of the access needle is facilitated by locking the access needle into the subcutaneous tissue of the perineum using a sliding platform that allows a user, such as a medical practitioner or patient caregiver, to place the access needle along a sagittal transducer plane at optimal positions for obtaining prostate biopsies. In some embodiments, upon placement of the access needle into a locked position, for example, in the pelvic floor, a user may then pass a biopsy needle through the access needle to a desired location of the prostate. In yet further embodiments, the passing of the biopsy needle through the access needle and to the prostate may be facilitated by direct sagittal plane visualization based on the alignment of the access needle.

Methods and systems provided herein do not require a patient to take antibiotics at any point prior to the biopsy procedure, nor do they require a patient to undergo bowel preparation in advance of the procedure. Methods, systems, and apparatus can reduce or eliminate multiple skin perforations by using a single access location or access site, while allowing multiple extractions of tissue or cell specimens from the prostate. Methods, systems, and apparatus in accordance with embodiments allow for real-time visualization during a free-handed, guided, transperineal approach, while also facilitating a complete assessment of the prostate with, for example, only one perforation of the patient's skin wherein the access needle is freely moveable in each plane.

Methods, systems, and apparatus of embodiments may include and facilitate treatment that uses a cryoablation probe for focal therapy of prostate cancer, a radiofrequency instrument, a thermotherapy instrument, any instrument for treatment of the cancerous area, or a combination of any of these instruments.

Methods, systems, and apparatus of embodiments enable planning and performing the free-hand transperineal prostate biopsies under the guidance of a device and of a real-time transducer in the sagittal imaging plane.

The biopsy is performed using a system that includes a biopsy guide, a transducer, an access needle, and a biopsy instrument. The access needle may allow the anesthesia to be injected into the patient, and the tissue or cell specimens of the prostate to be extracted. If anesthesia is used, a syringe may be included in the system. The transducer may be an ultrasound probe or any other type of device that is capable of causing a visualization of the prostate in a display device. In embodiments, the biopsy guide may be disposable. In embodiments, the biopsy guide may be formed of materials intended for a single use. In other embodiments, the biopsy guide is reusable. In some embodiments, the biopsy guide may be formed of materials intended for multiple uses.

The guide may include a sliding platform, stabilization bars, one or more upper and lower mounts, and a fastener. The upper and lower mounts may be curvilinear in shape. The upper and lower mounts may be positioned proximally or distally along an ultrasound probe, such as a transrectal ultrasound probe. The configuration and positioning of the upper and lower mounts are adjustable based on the shape of the ultrasound probe and the patient's body habitus.

The guide may be made of any material such as a plastic or metallic material. The guide may be disposable and made of a biodegradable plastic material. In other embodiments, the guide may be reusable and made of stainless steel. The dimensions, for example, the length, width, height, depth, and breadth of the sliding platform, stabilization bars, upper and lower mounts, and the fastener may vary and may be adjustable. The variable and adjustable dimensions, for example, of the stabilization bars, provide a user with flexibility in achieving and maintaining the guide in an appropriate ultrasound plane while performing biopsy procedures, while the user's patients may vary in size and levels of perineal subcutaneous tissue and fat. In a patient with an excessive amount of perineal subcutaneous tissue and fat, a larger stabilization bar will assist in locking the guide in the proper ultrasound plane.

The adjustable stabilization bars and mounts may be curvilinear in shape, allowing the guide to be placed proximally or distally along any cylindrical instrument, such as the transrectal ultrasound probe, which is determined by the surgeon based on the shape of the probe and the patient's body habitus. This allows the guide to be mounted to any assortment of ultrasound probes. Similarly, the platform may, for example, have various thicknesses.

The stabilization bars may be fixed to a top portion of the upper curvilinear mounts of the guide, and may extend beyond the front edge of the upper mounts. The stabilization bars may extend beyond the front edge of the upper curvilinear mount by approximately 8 mm. The guide may be approximately 60 mm wide, or the guide may be approximately 50 mm long, for example. The stabilization bars may have grooves for accommodating a sliding platform that is shorter in length than the stabilization bars. The grooves being configured to allow the platform to slide forward and backward along the stabilization bars.

An inner portion of the stabilization bars may have built-in grooves. The grooves accommodate a sliding platform which is shorter in length than the stabilization bars. This allows the sliding platform to slide from the back to the front of the stabilization bars. The stabilization bars may include a resistance as to prevent the sliding bar to freely move back and forth on the stabilization bar. This resistance may be introduced by the sliding platform or both the stabilization bar and the sliding platform. The resistance may be provided by a strip of rubber or any other material capable of providing friction or other. The strip may be curvilinear. The resistance may be generated by a mechanical system, such as a spring mechanism.

The sliding platform may have a hole through the platform. In some embodiments, the hole is drilled in the center of the platform. The hole can accommodate various types of needles, including access needles having various diameters, for example, spinal needles having a gauge in the range of 14-18. The hole can also accommodate needles having various lengths. The lengths of the needle may depend, in part, on the body habitus. The needle may be a reusable needle, such as a reusable spinal needle. The needle may be a disposable needle, such as a disposable spinal needle.

A flange of the guide secures the placement of the access needle to the guide. The flange may be configured to snap into the guide to secure the needle. The flange may be secured to the guide by other securing mechanisms. The flange can be of various shapes and configurations. For example, the flange may be u-shaped. As another example, the flange may have a thin or slim configuration. The guide assists in providing the appropriate angle of penetration and direction of the access needle, or other instruments that may be used in combination with the guide.

The hole in the guide is placed so that once the guide is mounted to the ultrasound probe, the drilled hole will be parallel to the sagittal transducer. The drilled hole may also accommodate the tip of a biopsy gun, or any other biopsy instrument. The sliding platform may be interchangeable and may be removed to allow placement of another sliding platform with a different sized to permit different sizes of needles and other instruments. The hole may be configured to accommodate a cryoablation instrument, a radiofrequency instrument, thermotherapy instrument, or any other instrument for diagnosis and treatment of a bodily tissue, including a cancerous area of a prostate.

The platform may have or define a predrilled hole in the center of the platform that can accommodate various sizes of needles and instruments. For example, the hole may be configured to accommodate a needle having a range of 14-18 gauges, such as a reusable 14 gauge spinal needle. Central hole placement on the platform enables alignment of the hole with a sagittal transducer when the guide is mounted to an ultrasound probe. The platform may have multiple holes to accommodate various applications and body habitus. Further, the platform may be of various thicknesses.

Once the one or more upper curvilinear mounts are placed at the desired location on the transrectal ultrasound probe, the access hole for a needle, such as a 14 gauge reusable spinal needle, will remain a fixed distance from the ultrasound probe. In embodiments, having one or more lower curvilinear mounts, the mounts may be positioned to cradle an upper aspect of the ultrasound probe.

At least two lower mounts are provided and may be individually positioned to accommodate various types of probes, which may have variable diameters along their shafts. In embodiments, a probe, such as a transrectal ultrasound probe, may have one or more diameters along the probe's shaft. In yet further embodiments, one end of the guide may be fixed at a location of the probe having a different diameter than the location where the other end of the guide is fixed. The separate lower mounts allow for the fixation of the guide, even with varying probe diameters.

The lower mount of the guide may include a lower right mount and a lower left mount connected by an adjustable mid-joint or fastener. The adjustable mid-joint or fastener allows the guide to be secured to the probe even if the diameter of the shaft of the probe is longer than the width of the lower mount. The mid-joint or fastener may be flexible to allow the right lower mount to form an acute angle with the left lower mount. This also allows for fixation of the guide to a probe shaft that is not circular in shape.

The lateral edges on both ends of the lower mounts may contain a notched post. Corresponding locations of the upper mounts contain holes, such as square shaped holes, to accommodate the notched post of a corresponding lower mount. An upper aspect of each hole includes a flange for locking the notched post in a fixed position. This configuration allows the lower mounts and the upper mounts to be secured to each other and to the probe.

Methods may include locating a suspicious area, positioning an access needle, and obtaining one or more tissue or cell specimens from an accurate point in the prostate. The method allows for multiple tissue or cell specimens to be obtained from a bodily organ, such as the prostate, and permits access to the prostate from different angles through a single initial access needle. The method may include calculating the volume of the prostate by positioning the access needle at a mid-point in the x axis from the lateral edge of the prostate to the urethra.

Methods may be performed using no anesthesia. Alternatively, an anesthetic may be used. For example, the anesthetic may be lidocaine, or any type of local anesthetic. The lidocaine may include 1 or 2% of a lidocaine solution.

The suspicious area or bodily organ may be located by using a transducer. The transducer may be any type of probe for accessing and viewing a targeted site or object, such as an ultrasound probe, or any type of transducer capable of providing visualization of the prostate and/or instruments and devices for diagnosis and treatment of the tissue. The biopsy may be performed using a biopsy gun, a suction device, or any type of instrument that is small enough to be introduced through the access needle and capable of extracting the tissue or cell specimen. The biopsy may be performed while the patient is in a dorsal lobothy position, prone position, or any position that allows for access to the perineal area.

Methods may include applying an antiseptic solution to the perineal area. The antiseptic solution may include betadine, or any other substance that reduces the possibility of infection, sepsis, or putrefaction. Methods may include applying bacitracin to the skin at the puncture site or any other type of topical preparation for preventing the possibility of infection.

Methods may include attaching a needle to a luer lock syringe, which may contain an anesthetic, or any other type of device capable of retaining its contents and dispensing its contents through the needle. A biopsy gun or any other instrument that may be attached to the needle and used for inserting or extracting any substance thru the lumen of the access needle.

Methods may include releasing the syringe from the needle after the anesthetic is injected. Methods may include dividing the prostate in three different regions and designating lateral, mid, apical prostate, and may include labeling the tissue or cell specimen containers, which will identify the tissue or cell specimens.

Methods may include securing the guide to the probe. This will permit the practitioner to take the biopsy gun as many times as necessary using his/her other hand, and, consequently, extract multiple tissue or cell specimens. It is contemplated that this can be done without assistance of any other person, and that the biopsy gun may also be attached to the guide in order to permit the surgeon to, for example, label the container with the tissue or cell specimen while performing the biopsy. Methods may also include monitoring all the actions in the prostate by way of a display device that provides images captured by the probe.

Methods may include moving the needle in x, y, and z planes. By being able to move the needle in x, y, and z planes, the surgeon is capable of extracting tissue or cell specimens from several different areas of the prostate without having to retrieve the needle and preventing other perforation of the patient's skin. In embodiments, movement of the needle within the patient's body is facilitated by using a display device.

Methods may include removing the access needle from the perineal area. This may be done while the biopsy gun is secured to the access needle or after the biopsy gun has been detached from the access needle.

Methods may include realigning the needle in the desired prostate region. If the surgeon wishes to start at the right lateral prostate region and notices that the needle tip is not directed at the lateral region, the surgeon rolls the ultrasound probe slightly and to note that the needle tip is directed to the desired region, then the surgeon may realign the needle to obtain tissue or cell specimen. The surgeon may realign the needle using one hand while having the needle attached to the biopsy gun, which may be attached to the probe through the guide.

Methods may include identifying the areas in which biopsy have already been performed. After each extraction of tissue or cell specimen during the biopsy, a hyperechoic streak remains visible on ultrasound display. This allows the surgeon to identify the area of the prostate and that an extraction has been made, as to allow the surgeon to prevent overlap of extractions.

In another embodiment, the method includes identifying the path of the urethra. This allows the surgeon from preventing passing the biopsy needle thru or into this path.

FIG. 1 is a side view of a guide 100 secured to a probe including a stabilization bar 101, fasteners 102, probe 103, lower mounts 104, and an upper mount 105. The stabilization bar 101 is an extension of the upper mount 105, as further discussed in FIG. 4. In embodiments, the distance between the fasteners 102 and the upper mount 105 may be adjustable to accommodate various applications and body habitus.

Figure 2A:
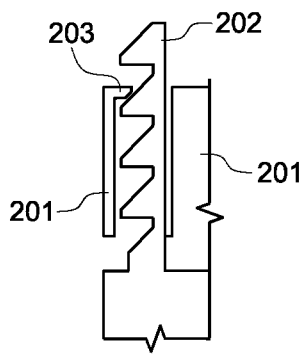
FIG. 2A shows an internal view of a guide fastener in accordance with an embodiment.

FIG. 2A is an internal view of a guide's fastener, including an aperture 201, teeth 202, and a flange 203. The flange 203 may be an extension of the aperture 201, which is part of the upper mount 105. Aperture 201 will allow the teeth 202 to be inserted into the upper mount 105, and the flange 203 will lock the teeth 202, which is connected to lower mount 104, to the upper mount 105. The aperture 201 with flange 203 and teeth 202 allows for adjusting the height of the guide 100.

In one embodiment, the fastener (e.g., via the aperture 201, flange 203, and/or the teeth 202) can be configured to fasten the guide 100 to the probe 103 with, e.g., varying levels of tension to provide for adjustments of the relative positions of the guide 100 and the probe 103 even after the guide 100 has been mounted to the probe 103. For example, the fastener 102 can provide a first level of tension sufficient to hold the position of an access needle (e.g., introduced through a hole or other needle mount of the guide 100) rotationally fixed to the probe 103 while still allowing for a forward or reverse sliding of the probe 103 with respect to the guide 100. By way of example, the forward or reverse sliding adjustment can be performed to adjust the penetration depth of the probe 103 with respect to the patient depending on a size of the patient. Once the final adjustment is made, the fastener can be actuated to final position or tension that will then lock further adjustments of the positioning of the guide 101 relative to the probe 103.

It is noted that the guide's fastener as described above is one example embodiment among other possible example fasteners that are applicable to various embodiments of the guide 100. Accordingly, it is contemplated that various embodiments of the guide 100 may use any now known or later developed fastening system that can secure the guide 100 to the probe 103.

Figure 2B:
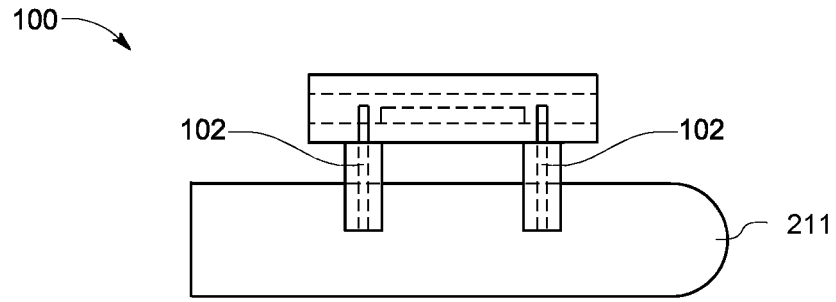
FIG. 2B shows a sheath-based guide fastener in accordance with an embodiment.
Figure 2C:
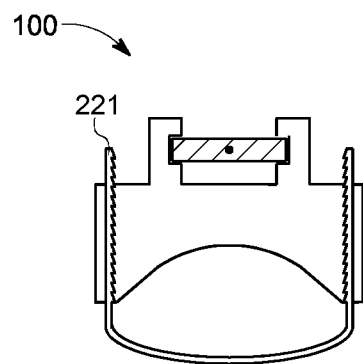
FIG. 2C shows a zip-tie-based guide fastener in accordance with an embodiment.

By way illustration and not limitation, examples of two fasteners are discussed with respect to FIGS. 2B and 2C. FIG. 2B shows a sheath-based fastener whereby the fasteners 102 are attached to a sheath 211 that is configured to slide over an end of a probe 103 and into an operable position. Although the sheath 211 is shown as a closed sheath, in another embodiment, the sheath 211 can be configured as a sleeve that is open-ended to slide over the probe 103. By way of example, the sheath 211 can be made of a flexible material (e.g., rubber) to provide for stretching and tension on probe 103.

In another embodiment, as shown in FIG. 2C, the guide 100 can be configured with a zip-tie style fastener in place of a lower mount mechanism to secure the guide 100 to the probe 100. In other embodiments (now shown), the guide 100 may be configured to fit to the probe 100 using screws, flanges, or other temporary, permanent, or semi-permanent fastening systems. In addition, although the fasteners 102 of the guide 100 may be configured as generic and adjustable fasteners that can support probes of a variety sizes and shapes, it is also contemplated that the fasteners can be fit to specific models of probes for customized applications.

Figure 3:
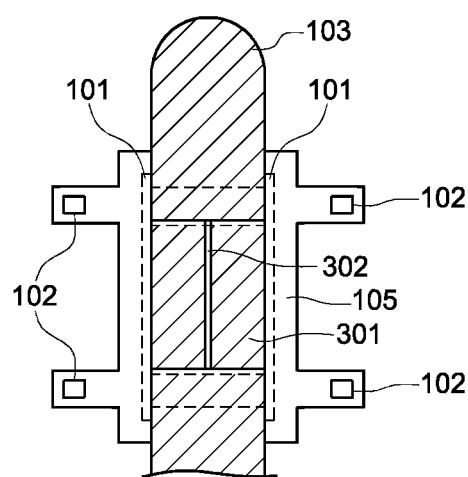
FIG. 3 shows a top view of a guide secured to a probe in accordance with an embodiment.

FIG. 3 is a top view of a guide secured to a probe. This figure includes a sliding platform 301, a drilled hole 302, stabilization bars 101, fasteners 102, an upper mount 105, and a probe 103. As previously described, in one embodiment, the drilled hole 102 can accommodate or support various sizes and/or configurations of needles (e.g., straight needles, curved needles, etc.) and instruments for performing a biopsy so that the needle can be aligned relative to the probe 103, thereby, also providing an alignment between the needle and an image produced by the ultrasound probe 103. In one embodiment, the drilled hole 102 can support an access needle through which a biopsy needle or other instrument can be introduced at a known alignment with respect to the probe 103. In addition, although the hole 102 to support, e.g., an access needle or other instrument is showed in a central midline position, the location of the hole can be configured at any position of the guide 100.

Figure 4:
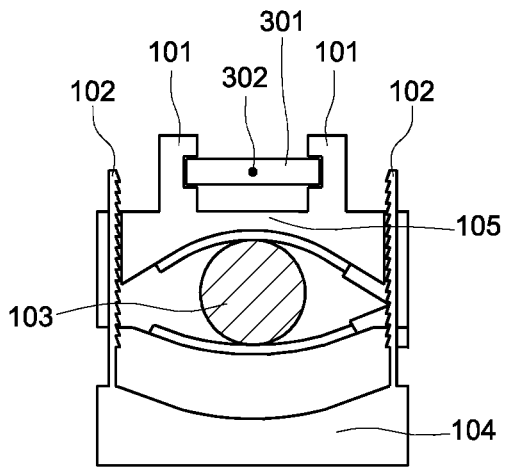
FIG. 4 shows a cross-sectional view of the back of a guide secured to a probe in accordance with an embodiment.

FIG. 4 is a cross-section view of the back of a guide secured to a probe including a sliding platform 301, drilled hole 302, stabilization bars 101, lower mount 104, upper mount 105, fasteners 102, and probe 103.

Figure 5:
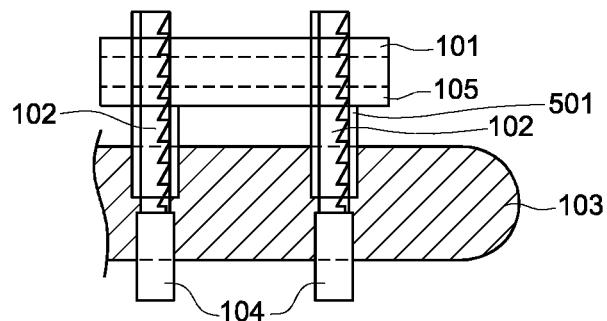
FIG. 5 shows a magnified view of a guide secured to a probe in accordance with an embodiment.

FIG. 5 is a magnified view of FIG. 1. FIG. 5 demonstrates minimum dimensions of preferred embodiments, which includes stabilization bars 101 and upper mount 105 from 30 mm to 50 mm long; the upper mount 105 with a height ranging from 10 mm to 15 mm; the stabilization bars 101 with a height that is about ⅓ of the height of the upper mount 105; fasteners 102 with a height of about 25 mm and 10 mm wide; a lower mount 104 10 mm wide. Additionally, the offset 501 from the distal point of the stabilization bar 105 to the fasteners 102 may be 5 mm. It is contemplated that any of these dimensions may vary, including the stabilization bar 101, which may be longer than the upper mount 105.

Figure 6:
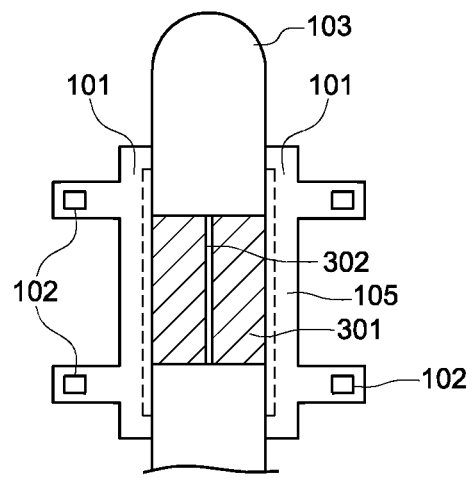
FIG. 6 is a magnified top view of a guide fastener in accordance with an embodiment.

FIG. 6 is a magnified internal view of the guide fastener shown in FIG. 2. FIG. 6 demonstrates minimum dimensions of preferred embodiments. The fasteners 102 may have an aperture 201 to accommodate teeth 202, wherein the fastener 102 is 5 mm to 10 mm wide. Additionally, the sliding platform 301, which may be from 12 mm to 25 mm wide, is slightly shorter than the distance between the two stabilization bars 101 as to accommodate the sliding platform while also securing it to the guide 100.

Figure 7:
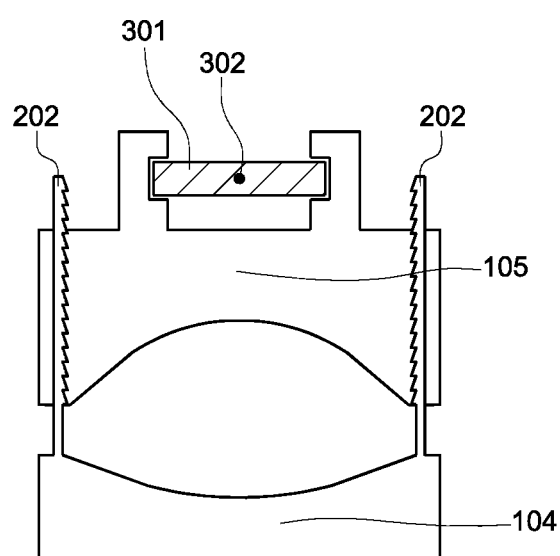
FIG. 7 is a magnified view of a guide in accordance with an embodiment.

FIG. 7 is a magnified view of the guide depicted FIG. 3, without the probe 103. FIG. 7 also demonstrates minimum dimensions of preferred embodiments, wherein the height of the upper mount 105 ranges from 5 mm to 10 mm; and the teeth 202 is from 5 mm to 8 mm wide.

FIG. 8 is a side view of a biopsy instrument that is about to penetrate the prostate, including a prostate 801, a probe 103, a biopsy instrument 802, a perineum skin 803, an anus 804, and a perforation point 805. The probe 103 is inserted into the anus 804 to provide real-time images of the biopsy, including images of the biopsy instrument 802 and the prostate 801. It is contemplated that the biopsy instrument 802 includes a needle and any other instrument capable of performing a biopsy.

FIG. 9 is a front view of a targeted area 902 of the prostate 801. FIG. 10 is a side view of a biopsy instrument penetrating the prostate 801, including a targeted area 902 of the prostate 801. The targeted area 902 is reached by biopsy instrument 802 after perforating perineum skin 803.

FIG. 11 is a front view of a targeted area of the prostate where a biopsy instrument will penetrate with areas in which the cell or tissue specimen has already been extracted. FIG. 11 depicts both an extracted area 1101 and a targeted area 902. The possibility of viewing the area in which the cell or tissue specimen has already been extracted permits the practitioner to avoid placing the access needle in an area that cell or tissue specimen has already been extracted. This allows the biopsy to be more efficient and more accurate.

FIG. 12 is a top view of FIG. 8, depicting a prostate 801, perineum skin 803, a probe 103, and a biopsy instrument 802. FIG. 13 is a right side view of a prostate and the path of the biopsy instrument including the path of the biopsy instrument 1301 and the perforation point 805. FIG. 13 illustrates that only one initial perforation to the skin of the patient is necessary in order to extract one or more cell or tissue specimens.

Figure 14:
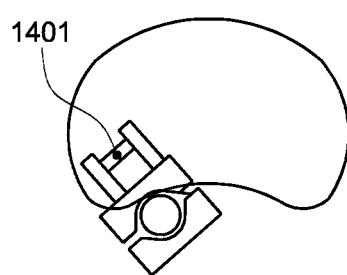
FIG. 14 is a front view of a guide positioned at a designated area of the prostate in accordance with an embodiment.
Figure 16:
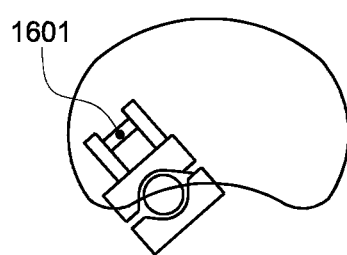
FIG. 16 is a front view of a guide positioned at another designated area of the prostate in accordance with an embodiment.
Figure 18:
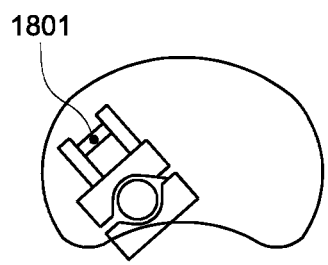
FIG. 18 is a front view of a guide positioned at a higher designated area of the prostate, according to one embodiment.

FIG. 14 is a front view of a guide determining a lower targeted or suspicious area 1401 of the prostate in which to penetrate the biopsy instrument, a prostate, and a probe. FIG. 16 is a front view of a guide determining a mid-target or suspicious area 1601 of the prostate in which to penetrate the biopsy instrument, a prostate, and a probe. FIG. 18 is a front view of a guide determining a higher targeted or suspicious area 1801 of the prostate in which to penetrate the biopsy instrument, a prostate, a probe. FIGS. 14, 16, and 18 demonstrates the variety of angles and positions in which a guide may be positioned in order to reach several regions of the prostate, such as the lateral region, mid region, and apical region. In order to the able to reach these areas, FIGS. 14, 16, and 18 demonstrate how the upper mount 105, the stabilization bars 101, or a combination of thereof can adjust in order to reach a lower targeted or suspicious area 1401, a mid-targeted or suspicious area 1601, or a higher targeted or suspicious area 1801 of the prostate.

Figure 15:
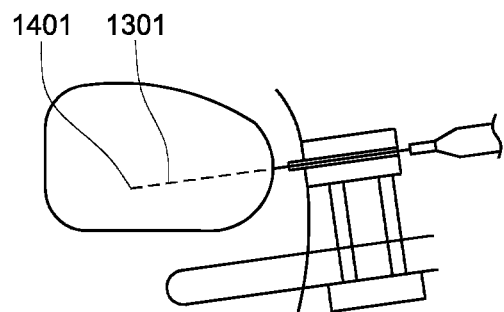
FIG. 15 is a side view of a guide positioned at a designated area of the prostate in accordance with an embodiment.
Figure 17:
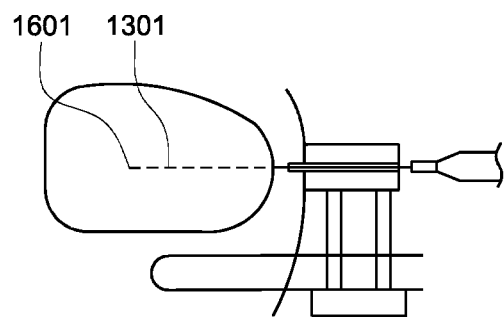
FIG. 17 is a side view of a guide positioned at another designated area of the prostate.
Figure 19:
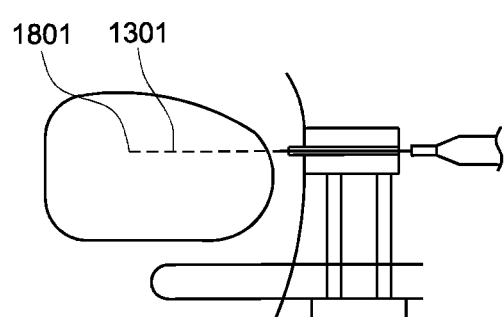
FIG. 19 is a right side view of a guide positioned at a higher designated area of the prostate in comparison with that shown in FIGS. 14-17 in accordance with an embodiment.

FIGS. 15, 17, and 19 demonstrate a side view of FIGS. 14, 16, and 18 and the paths of the biopsy instrument 1301 taken by a biopsy instrument to reach lower targeted or suspicious area 1401, a mid-targeted or suspicious area 1601, or a higher targeted or suspicious area 1801 of the prostate.

Figure 20:
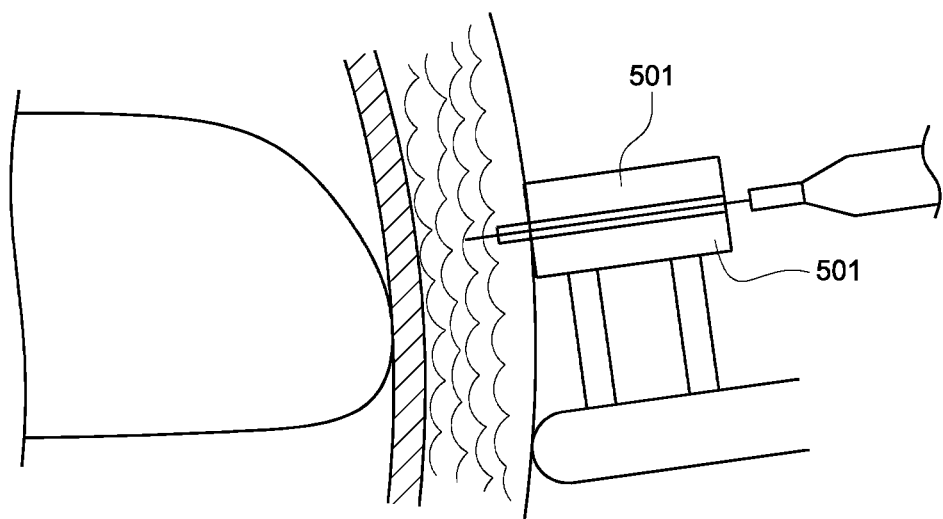
FIG. 20 is a side view of a guide and a biopsy instrument firmly penetrating a fat plane and perineum skin of a patient in accordance with an embodiment.

FIG. 20 is a right side view of a guide, and a biopsy instrument firmly penetrating a fat plane of perineum skin, including offset 501 of a stabilization bar 101. This allows for stabilization in a patient with an excessive amount of perineal subcutaneous tissue, fat, or a combination thereof. A larger stabilization bar 101 will assist in locking the guide in the proper ultrasound plane. Accordingly, the offset 501 may longer than 5 mm for these purposes.

Figure 21:
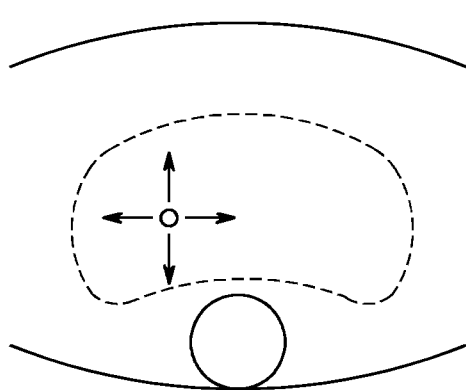
FIG. 21 is a view of an access needle positioned at the access site in accordance with an embodiment.

FIG. 21 is a front view of a prostate, a probe, a targeted or suspicious area, wherein the biopsy instrument may reach any area of the prostate. FIG. 21 demonstrates that the biopsy instrument can reach the entire prostate while using only one perforation point 805. After obtaining one cell or tissue specimen, the biopsy instrument 802 may be partially retrieved from the perineum area at a point in which the distal point of the biopsy instrument 802 is redirected to another targeted or suspicious area. Then, the biopsy instrument (usually the needle of the biopsy instrument) is inserted to the second targeted or suspicious area for obtaining a cell or tissue specimen of another area of the prostate.

Figure 22:
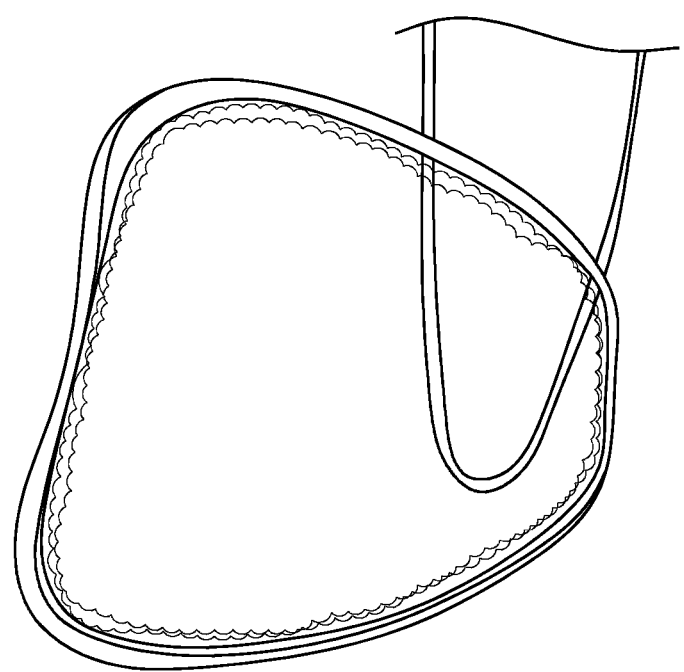
FIG. 22 is a magnified view of the right side of a prostate and a biopsy instrument in accordance with an embodiment.

FIG. 22 is a magnified view of the right side of a prostate and a biopsy instrument. FIG. 22 depicts the location of the biopsy instrument inside the prostate and the other paths in which the biopsy instrument may take utilize for additional samples or retrieval. In embodiments, the biopsy needle or other instruments do not reach the initial part of the penis, which is in a different plane from the prostate.

Figure 23:
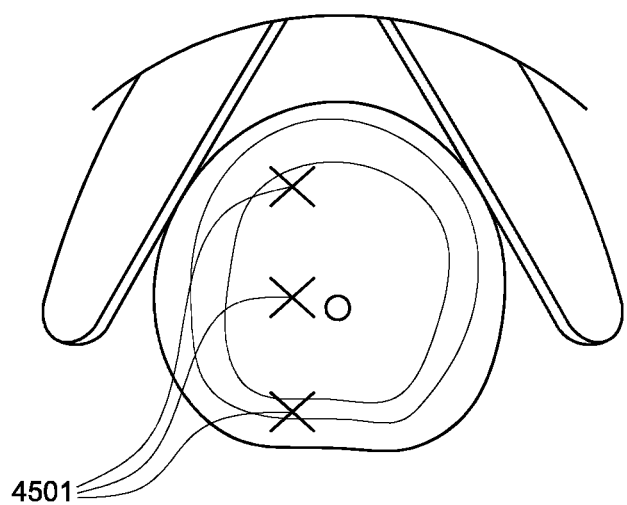
FIG. 23 is an image of the front side of a prostate and a biopsy instrument being retrieved from the prostate, and other targeted areas in accordance with an embodiment.

FIG. 23 is an image of the front side of a prostate and a biopsy instrument being retrieved from the prostate, and other targeted areas. FIG. 23 shows a procedure being applied to the apical region of the prostate.

The urethra should be avoided in any part of the procedure, but it is mostly important when extracting cell or tissue specimens from the apical region of the prostate, when the chances of perforation is greater. After several extractions, the practitioner is able to see the blood streak from where the cell or tissue specimen was taken so as to avoid overlapping.

After this procedure, the patient may be put with restriction for no more than 1 day. If the patient is put on restriction for 1 day, after the one-day-restriction, no restriction is made.

Figure 24:
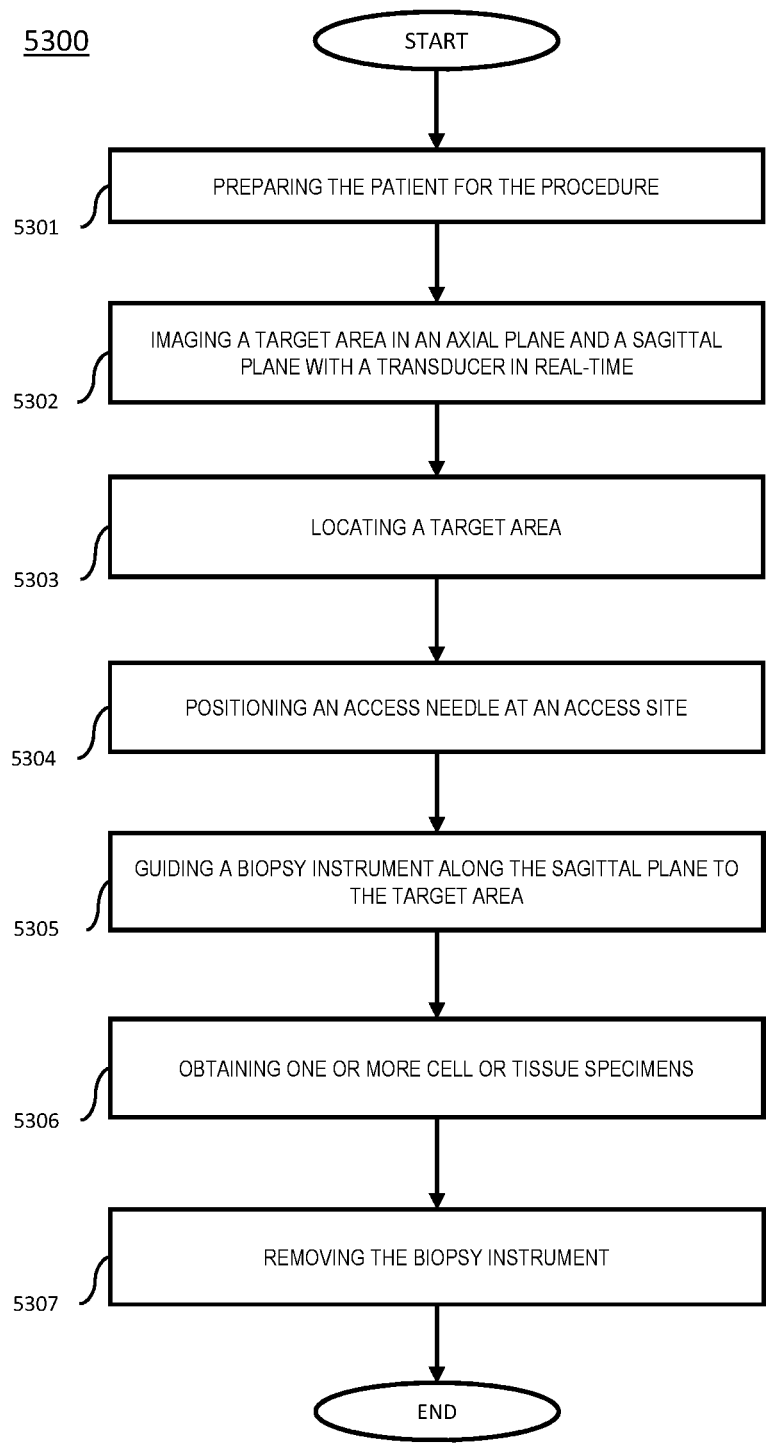
FIG. 24 shows a method for performing a prostate biopsy in accordance with an embodiment.

In an embodiment, the biopsy system performs the processes 2400 of FIG. 24. At 2401, a patient is prepared for the biopsy procedure by having the patient get into a lithotomic position, prone position, or any position that allows for access to the perineal area. The biopsy procedure may be a prostate biopsy. In some embodiments, the patient's scrotum is elevated using, for example, two strips of plastic tape. The perineum is prepared with an antiseptic solution to the perineal area, for example, the antiseptic solution may include betadine.

At 2402, a target area or object, such as the prostate, is imaged. Imaging may be performed with a transducer, such as an ultrasound probe. Imaging of a target area may be in a sagittal and/or axial plane and may be performed in real-time with direct visualization. Utilizing the real-time image, a user can identify areas of interest, e.g. suspicious areas or the target area or object at 2403.

The user may determine an access site for positioning an access needle. At 2404, an access needle is positioned at an access site in subcutaneous tissue of the perineum. The access site may be at a midpoint between a lateral edge of the prostate and the urethra along an x axis, and a midpoint between an anterior capsule and a posterior capsule along a y axis. The access needle is guided and positioned at the access site by using the guide.

At 2405, a biopsy instrument is guided to the target or suspicious areas or object. The biopsy instrument may include a biopsy needle. The guiding of the biopsy instrument can be facilitated by using the real-time visualization provided by the transducer. Real-time visualization also facilitates obtaining tissue or cell specimens from an accurate point in the prostate, for example. The method allows for one or more tissue or cell specimens to be obtained from a bodily organ, such as the prostate at 2406, and permits access to the prostate from different angles through a single initial access needle.

At 2407, the biopsy instrument may be retrieved and removed from the patient. The method may include calculating the volume of the prostate by positioning the access needle at a mid-point in x axis from the lateral edge of the prostate to the urethra.

Figure 25:
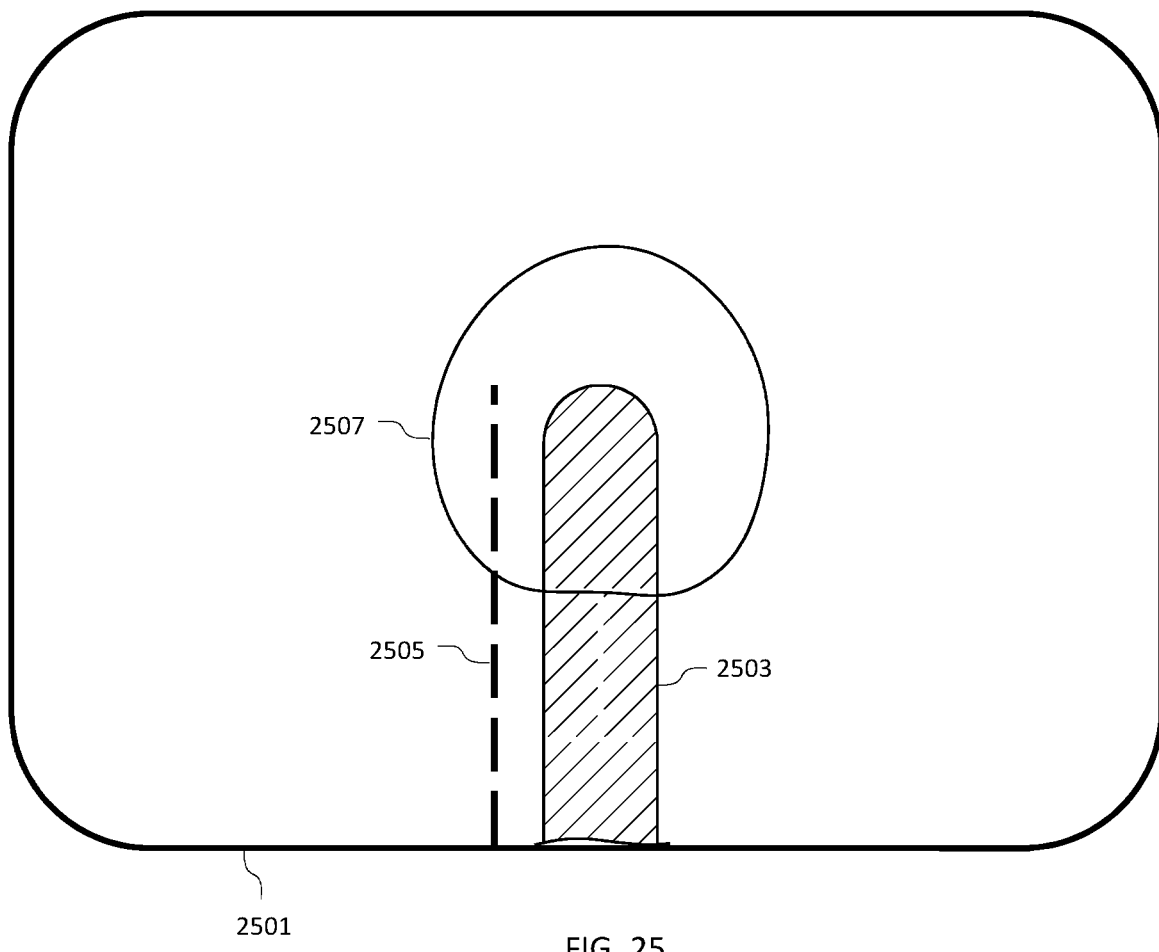
FIG. 25 is an ultrasound image showing a transducer, access needle path extending from an access point at a perineal site to a prostate, and a prostate.

FIG. 25 shows an ultrasound 2501 showing a transrectal probe 2503 and an access needle guide line 2505. The needle guide line enables the practitioner to observe a needle path whereby the access needle has contacted the prostate 2507, thereby enabling the practitioner to avoid overlapping sampling, and to avoid perforating the prostate.

Figure 26A:
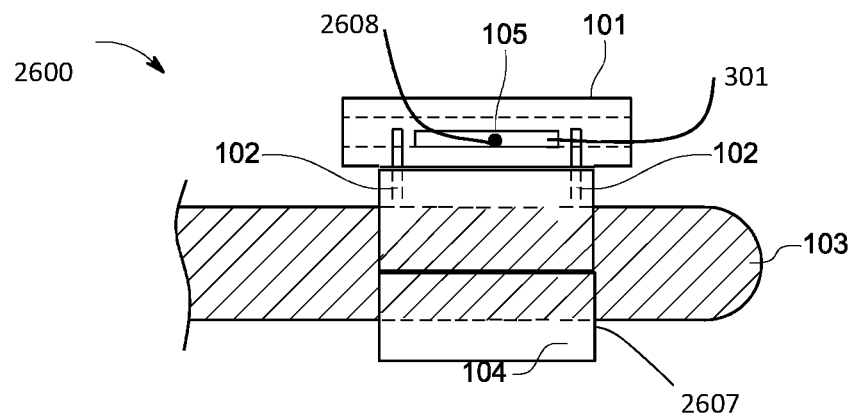
FIGS. 26A-26C show side views of a guide configured with a pivoting mount in accordance with an embodiment.
Figure 26B:
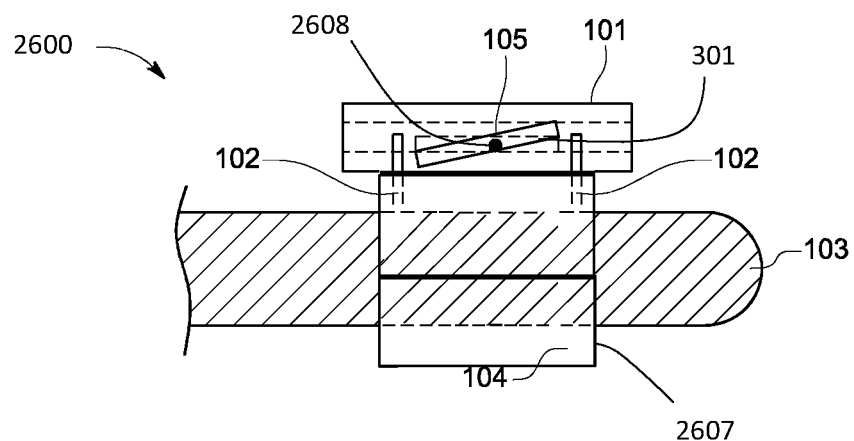
Figure 26C:
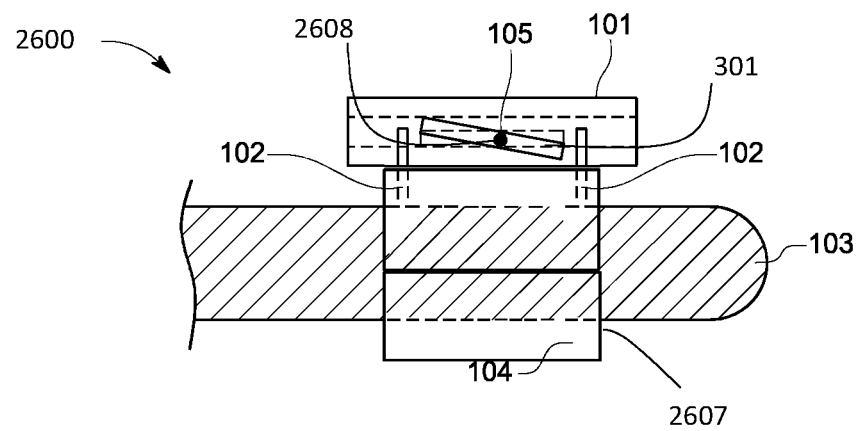

FIGS. 26A-26C show side views of an alternative embodiment of a guide 2600 secured to a probe including a stabilization bar 101, fasteners 102, probe 103, lower mount 104, and an upper mount 105. The stabilization bar 101 is an extension of the upper mount 105, as further discussed in FIG. 4. In embodiments, the distance between the fasteners 102 and the upper mount 105 may be adjustable to accommodate various applications and body habitus.

The guide 2600 includes a sliding platform 301. The guide is fitted to the probe 103 by a sleeve 2607. The sleeve 2607 is formed by the lower mount 104 and the upper mount 105. The sleeve 2607 may be configured to slide over an end of the probe 103 into an operable position as shown in FIGS. 26A-26C. The sleeve 2607 is a partial sleeve that has an opening at both ends of the sleeve 2607 to enable slidable mounting to and removal from the probe 103.

The sliding platform 301 of the guide 2600 may be pivotably mounted to enable movement in a direction perpendicular to a longitudinal axis of the probe 103, as shown in FIGS. 26A-26C. In particular FIGS. 26A-26C show that the sliding platform 103 is fixed to the guide at a pivot point 2608. The sliding platform 103 is configured to pivot at pivot point 2608 to enable, for example, normal or vertical adjustment of an access needle (not shown) in directions perpendicular to a longitudinal axis of the probe 103 while ensuring that a longitudinal axis of the access needle (not shown) remains parallel to the longitudinal axis of the probe 103.

For example, FIG. 26A shows a sliding platform 301 in a first position at which a lateral planar surface of the platform 301 extends in a direction parallel to the longitudinal axis of the probe 103. FIG. 26B shows the sliding platform 301 pivoted to a second position wherein a front end the platform 301 is disposed a distance from the probe 103 that is greater than a distance between an opposite rear portion of the platform 301 and the probe 103. FIG. 26C shows the sliding platform 301 pivoted to a third position wherein the rear end of the platform 301 is disposed a distance from the probe 103 that is greater than a distance between the opposite front end of the platform 301 and the probe 103.

In another embodiment, the method may be performed without the patient taking antibiotics or undergoing bowel preparation before having the procedure. During the procedure, the practitioner may administer an anesthetic to the patient, for example, lidocaine, or any type of local, anesthetic. The lidocaine may be included in a solution having 1% of lidocaine.

In an embodiment, the suspicious area is located by using a transducer. The transducer may be any type of transrectal robe for prostate cancer, such as an ultrasound probe, or any type of transducer capable of imaging the prostate and the extraction device. The biopsy may be performed using a biopsy gun, a suction-mechanism, or any type of instrument that is small enough to be introduced through the access needle and capable of extracting the tissue or cell specimen. The biopsy may be performed while the patient is in a lithotomy position, prone position, or any position that allows for access to the perineal area.

In another embodiment, methods may include applying an antiseptic solution to the perineal area such as betadine, or any other substance that reduces the possibility of infection, sepsis, or putrefaction.

In another embodiment, the ultrasound probe may be a B&K 8848 transrectal ultrasound probe, or any other ultrasound capable of causing visualization of the prostate and the extraction device. The frequency range may be 5-12 MHZ, and the focal range may be 3-60 mm. The ultrasound probe may be able to cause the visualization of the prostate and extraction devices at least in the axial plane, sagittal plane, or a combination thereof.

In another embodiment, methods may include attaching a needle to a luer lock syringe, which may contain an anesthetic, or any other type of device capable of retaining its contents and to dispense its contents through the needle. A biopsy gun or any other instrument may be attached to the needle for inserting or extracting any substance through the lumen of the access needle.

In another embodiment, the method includes releasing the syringe from the needle after the anesthetic is injected. The method may include dividing the prostate in three different regions and designating lateral, mid, apical prostate, and may include labeling the tissue or cell specimen containers, which will identify the tissue or cell specimens.

In another embodiment, a biopsy gun may be an 18 gauge biopsy gun, or any other size that is capable of being coaxially inserted thru the lumen of the access needle.

In another embodiment, methods may include securing the guide to the probe. This will permit the practitioner to take the biopsy gun as many times as necessary using his or her other hand, and, consequently, extract multiple tissue or cell specimens. It is contemplated that this can be done without assistance of any other person, and that the biopsy gun may also be attached to the guide in order to permit the surgeon to e.g. label the container with the tissue or cell specimen while performing the biopsy. The method may also include monitoring all the actions in the prostate thru a display device, which will transmit images captured by the probe.

In another embodiment, methods may include moving the needle in x, y, and z planes. By being able to move the need in x, y, and z planes, the surgeon is capable of extracting tissue or cell specimens from several different areas of the prostate without having to retrieve the needle and preventing other perforation of the patient's skin.

Methods may further include removing the access needle from the perennial area. Removal of the access needle may be performed while the biopsy gun is secured to the access needle or after the biopsy gun has been detached from the access needle.

Methods may include realigning the needle in the desired prostate region. If the surgeon wishes to start at the right lateral prostate region and notices that the needle tip is not directed at the lateral region, the surgeon rolls the ultrasound probe slightly and to note that the needle tip is directed to the desired region, then the surgeon may realign the needle to obtain tissue or cell specimen. The surgeon may realign the needle using one hand while having the needle attached to the biopsy gun, which may be attached to the probe through the guide.

Methods may include identifying the area in which a biopsy has already been performed. After each extraction of tissue or cell specimen during the biopsy, a hyperechoic streak remains visible on ultrasound display. This allows the surgeon to identify the area of the prostate and that an extraction has been made, as to allow the surgeon to prevent overlap of extractions.

In another embodiment, methods may include identifying the path of the urethra. This allows the surgeon from preventing passing the biopsy needle thru or into this path. In another embodiment, the method includes pressuring the perineum. In yet another embodiment, the method includes applying bacitracin to the skin at the puncture site or any other type of topical preparation for preventing the possibility of infection. In another embodiment, positioning the access needle is performed without the need of a biopsy grip, wherein the guide provides the precise point for the biopsy.

An apparatus and system in accordance with embodiments discussed above is used to carry out these methods. In an alternative embodiment of apparatus and systems, a guide may not include a lower mount, and may include an access needle. The guide includes a stabilization bar, sliding platform, a hole located in approximately the center of the platform, an upper mount, teeth, aperture, arms, and a connector. The access needle includes a hub and is secured to the guide. The teeth may be part of, or may be attached to, a lower mount. The teeth may be inserted into the aperture in order to secure the guide to a probe, for example. It is contemplated that the combination of the aperture and the teeth may form a fastener mechanism. In embodiments, connector is part of, or may be attached to, an access needle, and may be secured to the upper mount in order to provide stabilization of the access needle and to allow the practitioner to move the access needle by merely moving, for example, a probe that may be secured to the guide.

A connector and a hub permit the use of various other instruments such as, for example, a non-biopsy instrument, to be secured. A biopsy instrument may be inserted into the access needle in order to reach a targeted area. The upper mount may include arms. In embodiments, the arms may be shorter, longer, or may not exists, in which case the aperture is disposed directly in the upper mount. When the aperture is directly in the upper mount, upper mount may be longer, thicker, or a combination thereof.

In some embodiments, the guide may include lower mounts that have teeth. Arms may extend from the upper mount to allow the height of the guide to be adjusted and to be placed farther from or closer to the probe. The arms permit the access needle to be maintained at a certain distance from a probe. In embodiments, the material of the guide may be a plastic or any other material, including other plastic materials, or any other material that is cost effective. In embodiments, the guide may be reusable and may be formed with a stainless steel. The lower mount may be curvilinear and flexible to allow the lower mount to bend if necessary to secure the guide to the probe.

Reference is made to FIGS. 27-35D, which depict various views of another embodiment of a transperineal biopsy guide 2700. As with the previously described embodiments, the biopsy guide 2700 may couple with a transrectal probe and may be used in guiding an access needle in a transperineal prostate biopsy procedure. While reference will be made to the embodiment in FIGS. 27-35D, aspects of the previously described embodiments may be incorporated into the present embodiment without limitation. And, aspects of the present embodiment may be similarly incorporated into the previously described embodiments without limitation.

To begin, reference is made to FIGS. 27-30, which depict, respectively, a front isometric view, a front view, a side view, and a front isometric exploded view of the transperineal biopsy guide 2700. As seen in the figures, the biopsy guide 2700 includes an upper mount 2702 and a lower mount 2704. The lower mount 2704 includes a probe coupling or fastening mechanism 2706 to couple the lower mount 2704 with a transrectal probe (not shown in FIGS. 27-28, but shown in FIGS. 1, 2B, and 3-6, for example). The lower mount 2704 additionally includes an upper mount coupling mechanism 2714 to couple the lower mount 2704 with the upper mount 2702. While FIGS. 27-30 depict a single coupling mechanism 2706, it is foreseen that the biopsy guide 2700 may include more than one coupling mechanism 2706, as shown and described in previous embodiments.

The upper mount 2702 may couple with the lower mount 2704 and may include a guide member 2708 and a displacement member, translating member, or sliding platform 2710. The displacement member 2710 may couple with an access needle 2712 and be supported by the guide member 2708. More particularly, the displacement member 2710 may slidingly couple with the guide member 2708 such that the displacement member 2710 and the access needle 2712 are guided along a trajectory that is fixed relative to the guide member 2708 and the transrectal probe. The trajectory of the access needle 2712 may be generally parallel with a longitudinal axis of the transrectal probe when the biopsy guide 2700 is coupled with the probe.

Figure 31D:
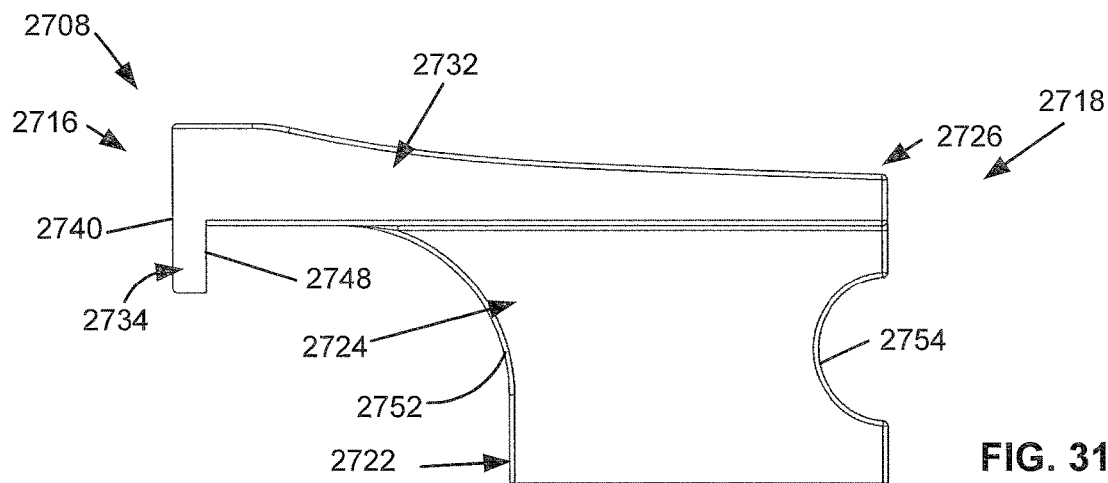
FIG. 31D is a side view of the upper mount of the biopsy guide.
Figure 31E:
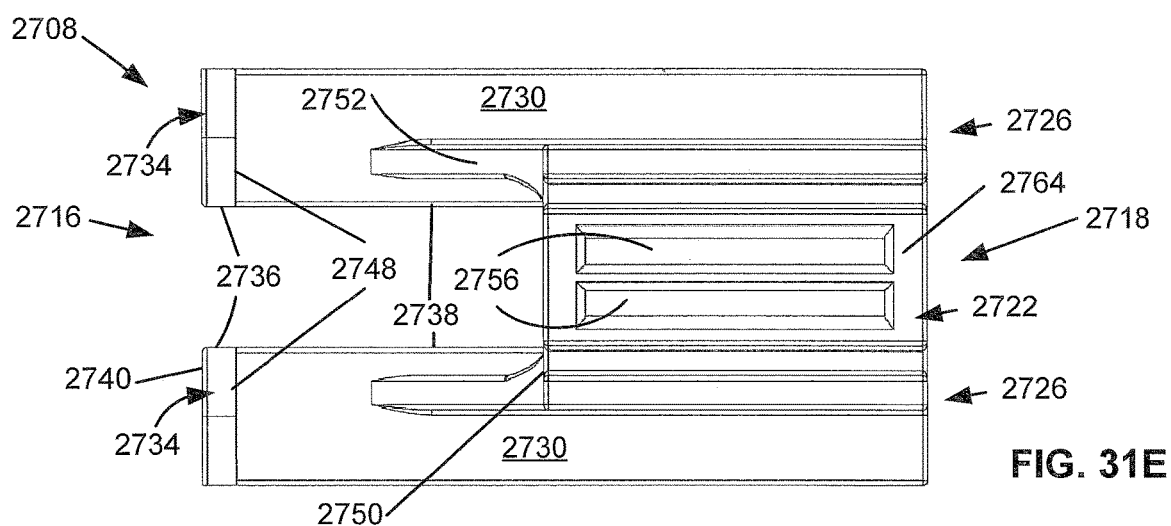
FIG. 31E is a bottom view of the upper mount of the biopsy guide.
Figure 31F:
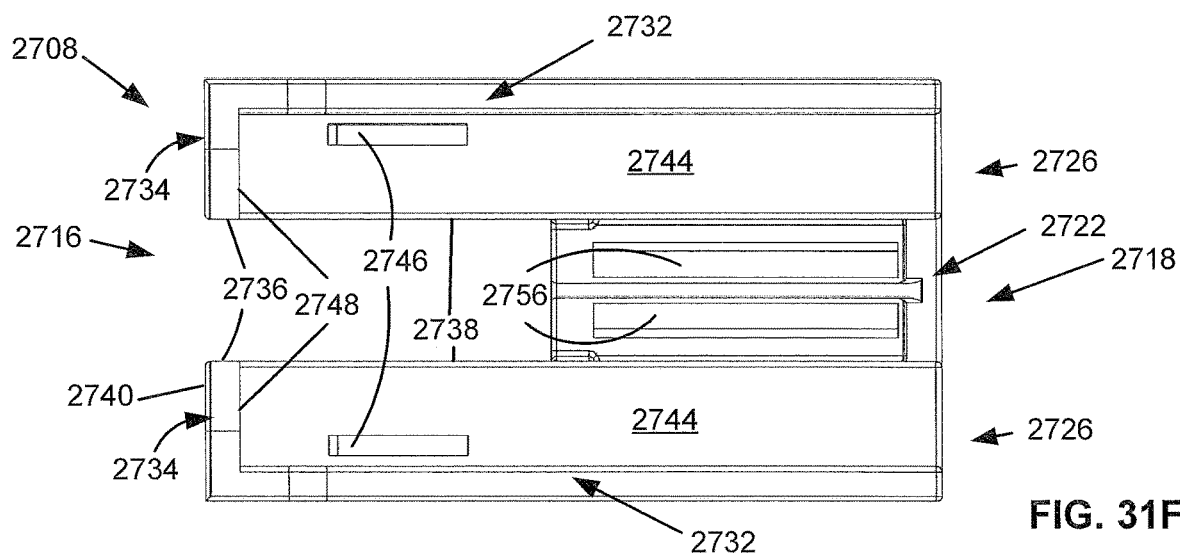
FIG. 31F is a top view of the upper mount of the biopsy guide.

Reference is made to FIGS. 31A-31F, which depict various views of the guide member 2708 of the upper mount 2702 of the biopsy guide 2700. FIG. 31A is a front isometric view of the guide member 2708; FIG. 31B is a front view of the guide member 2708; FIG. 31C Is a back view of the guide member 2708; FIG. 31D is a side view of the guide member 2708;

FIG. 31E is a bottom view of the guide member 2708; and, FIG. 31F is a top view of the guide member 2708.

As seen in the figures, the guide member 2708 includes a distal end 2716, a proximal end 2718 opposite the distal end 2716, and a longitudinal axis 2720 extending through the distal and proximal ends 2716, 2718. As described herein locational orientations of distal and proximal are relative to the patient or, more particularly, the perineum of the patient. As such, distal generally refers to towards the patient and proximal refers to away from the patient.

Referring back to the figures, the guide member 2708 further includes a base platform 2722 extending substantially perpendicularly between a pair of vertical extension members 2724. Atop each of the vertical extension members 2724 is a guide rail or stabilization bar 2726 that is adapted to slidingly engage with and allow the displacement member 2710 to translate along a trajectory that is parallel with the longitudinal axis 2720 of the guide member 2708.

As best seen in FIGS. 31A and 31C, each of the guide rails 2726 includes a generally rectangular member 2728 that is perpendicularly oriented to the vertical extension members 2724. The rectangular member 2728 extends from the proximal end 2718 to the distal end 2716 of the guide member 2708. The vertical extension members 2724 couples with a bottom surface 2730 of the rectangular member 2728. An outer lateral edge of the rectangular member is coupled with a side member 2732 that extends from the proximal end 2718 to the distal end 2716 of the guide member 2708. A distal member or flange 2734 extends inwardly from the rectangular member 2728 a distance that is equal to the width of the rectangular member 2728. More particularly, the distal member 2734 includes a rounded inner edge 2736 that is coplanar, at its apex, with an inner edge 2738 of the rectangular member 2728. The distal member 2734 may include a planar distal face or surface 2740 with an opening 2742 formed therein. The opening 2742 may facilitate an access point for injection molding. As with previously described embodiments, the guide rails 2726 and, more particularly, the distal face 2740 of the guide rails 2726 may facilitate the positioning and holding of the perineal skin and subcutaneous tissue to allow positioning of the access needle 2712.

As seen in FIGS. 31A, 31C, and 31F, a top surface 2744 of the rectangular member 2728 includes a stop feature 2746 to secure or lock the displacement member 2710 in a distal or deployed condition or position. The stop feature 2746 is a ramp that distally slopes upward until the apex of the ramp at which point the ramp distally slopes downward. In the distal position, the displacement member 2710 is at a distal-most position and abuts or is adjacent a proximal face 2748 of the distal member 2734. The distal member 2734, thus, prevents further distal movement of the displacement member 2710 and the stop feature 2746 restrains proximal movement a certain amount. In certain embodiments, as seen in the figures, the proximal end 2718 of the rectangular member 2728 is open such that the displacement member 2710 can be slidingly engaged with the rectangular member 2728.

As seen in FIGS. 31A and 31D-31F, the base platform 2722 extends about one half of the overall longitudinal distance of the guide rails 2726. In this way, the guide rails 2726 extend beyond both the base platform 2722 and the vertical extension members 2724 such that the guide rails 2726 may contact the perineal skin and subcutaneous tissue of the patient but not a distal edge 2750 of the base platform 2722 or a distal edge 2752 of the vertical extension members 2724. And since a distal portion of the lower mount 2704 lies generally flush with the distal edge 2750 of the base platform 2722, the lower mount 2704 also may be spaced apart from the skin of the patient during the biopsy procedure. In this way, in certain embodiments, the guide rails 2726 may contact the skin of the patient while the other portions of the guide 2700 remain spaced apart from the patient's skin.

As seen in FIG. 31D, the distal edge 2752 of the vertical extension member 2724 is arcuate and a proximal edge 2754 of the vertical extension member 2724 includes a semi-circular path about halfway between the base platform 2722 and the guide rails 2726. As seen in FIGS. 31E-31F, the base platform 2722 includes a pair of channels 2756 extending parallel to each other and extending longitudinally. These channels 2756 may coaxially align with snap features 2758 in the upper mount coupling mechanism 2714 of the lower mount 2704 to facilitate the upper mount 2702 being coupled with the lower mount 2704. Once the channels 2756 and the snap features 2758 are aligned, the upper and lower mounts 2702, 2704 may be snapped together such that the snap feature 2758 extends through the channels 2756 to securely couple the mounts together. While the figures show channels 2756 and snap features 2758, other mechanisms are possible to couple the upper and lower mounts 2702, 2704. For example, the base platform 2722 and the upper mount coupling mechanism 2714 may each include through holes that coaxially align. And, screws or nuts/bolts may be used to secure the mounts 2702, 2704 together.

As seen in FIGS. 31B-31C and 31E, the bottom surface 2762 of the base platform 2722 includes a rectangular rail or protrusion 2764 extending longitudinally. The top surface of the base platform 2722 includes a longitudinally extending groove, which may be used to align the guide member 2708 with the sagittal plane of the ultrasound probe. As seen in FIG. 31E, the channels 2756 extend through the rail 2764. As will be described subsequently, the rail 2764 may engage with a platform 2766 of the upper mount coupling mechanism 2714 of the lower mount 2704 so as to align the upper and lower mounts 2702, 2704 upon coupling together.

Figure 32A:
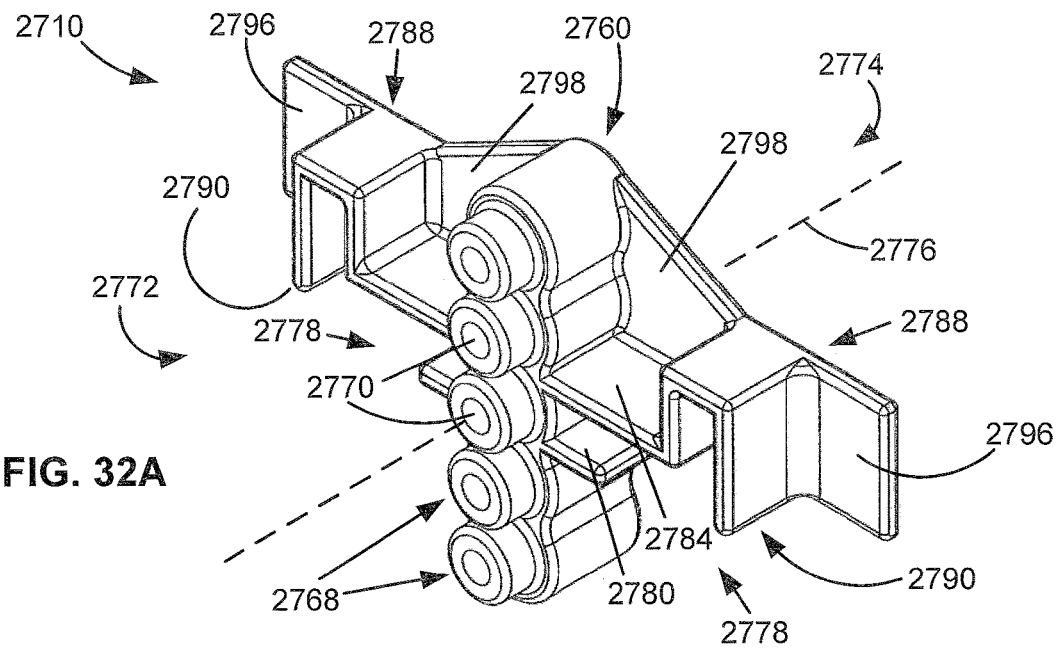
FIG. 32A is a front isometric view of the displacement member of the biopsy guide.
Figure 32B:
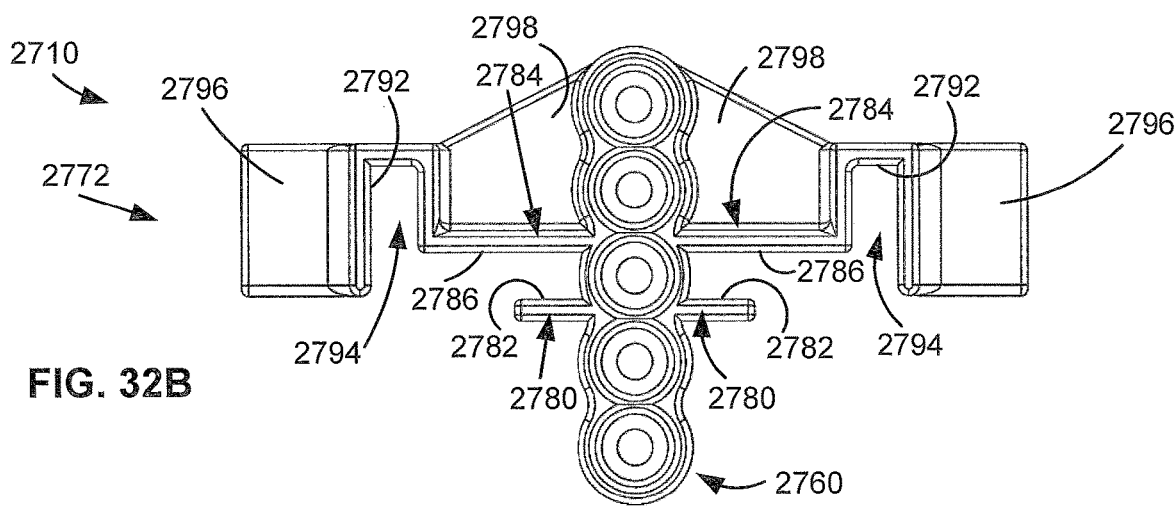
FIG. 32B is a front view of the displacement member.
Figure 32C:
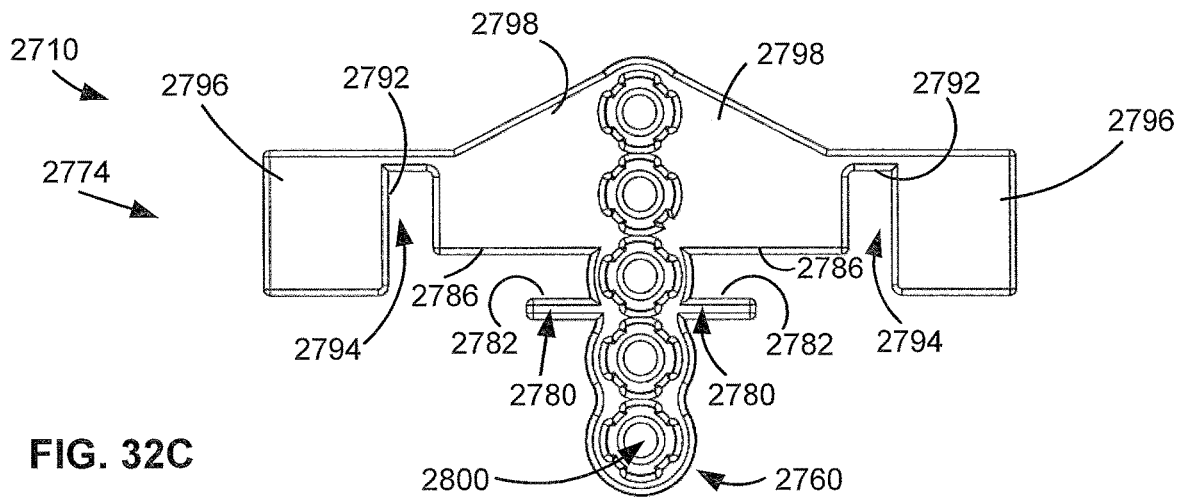
FIG. 32C is a back view of the displacement member.

Reference is made to FIGS. 32A-32C, which depict, respectively, a front isometric view, a front view, and a back view of the displacement member 2710. As described previously, the translating or displacement member 2710 may be coupled with the guide rails 2726 of the guide member 2708 so as to be displaceable or slidable between the proximal end 2718 of the guide member 2708 to the distal end 2716. Thus, when the access needle 2712 is coupled with the displacement member 2710, the access needle 2712 is also displaceable between the proximal end 2718 of the guide member 2708 to the distal end 2716.

As seen in the figures, the displacement member 2710 includes a central vertically extending member 2760 having five needle receiving ports 2768 formed therein. Each needle receiving port 2768 includes an opening 2770 extending from a distal end 2772 to a proximal end 2774 of the displacement member 2710. Each of the openings 2770 of the needle receiving ports 2768 are generally vertically aligned with each other and each includes a trajectory axis 2776 defining a trajectory of the access needle 2712 when positioned within the opening 2770. The trajectory axis 2776 is generally parallel to the longitudinal axis 2720 of the guide member 2708 when the displacement member 2710 is coupled with the guide member 2708. The trajectory axis is also generally parallel with a longitudinal axis of the probe when the biopsy guide 2700 is coupled with the probe. Thus, the trajectory axis 2776 of the access needle 2712 may be generally fixed or constant, in a generally parallel orientation to the previously described axes, as the displacement member 2710 displaces distal-proximal relative to the guide member 2708.

A particular needle receiving port 2768 may be chosen based on a desired distance from the probe. Thus, if a physician desires that the access needle 2712 should be positioned nearer the probe, a particular needle receiving port 2768 may be chosen that is at the bottom of the displacement member 2710. In certain embodiments, the openings 2770 of the needle receiving ports 2768 may be vertically spaced apart about 5 mm. In certain embodiments, the openings 2770 of the needle receiving ports 2768 may be vertically spaced apart about 3 mm. In certain embodiments, the openings 2770 of the needle receiving ports 2768 may be vertically spaced apart about 4 mm. In certain embodiments, the openings 2770 of the needle receiving ports 2768 may be vertically spaced apart at any interval between about 2 mm to about 6 mm, among other distances.

While the vertically extending member 2760 includes five needle receiving ports 2768, it is foreseen that more or less ports may be included in the displacement member 2710 without limitation.

The displacement member 2710 further includes a coupling mechanism 2778 to displaceably couple the displacement member 2710 and the guide rails 2726. The coupling mechanism 2778 includes a pair of lower tab members 2780 extending laterally out and away from the vertically extending member 2760. When coupled with the guide rails 2726, the lower tab members 2780 may abut or be positioned adjacent the bottom surface 2730 of the rectangular member 2728. The tab members 2780 include a planar top surface 2782 that may provide sliding contact with the bottom surface 2730 of the rectangular member 2728. The planar contact between the surfaces may contribute to stability of the displacement member 2710 relative to the guide rails 2726 by reducing vertical tilt of the displacement member 2710.

The coupling mechanism 2778 further include an upper member 2784 positioned above the lower tab members 2780. A bottom surface 2786 of the upper members 2784 may abut or be positioned adjacent the top surface 2744 of the rectangular member 2728 when the displacement member 2710 is coupled with the guide rails 2726. The bottom surface 2786 of the upper members 2784 is planar and, thus, the planar contact between the surfaces may contribute to stability of the displacement member 2710 relative to the guide rails 2726 by reducing vertical tilt of the displacement member 2710. The upper members 2784 and the lower tab members 2780 operate to sandwich the rectangular members 2728 of the guide rails 2726 when the displacement member 2710 is coupled with the guide member 2708.

The coupling mechanism 2778 further includes a lateral brace mechanism 2788 at lateral ends of the upper members 2784. The lateral brace mechanism 2788 includes an upside-down U-shaped member 2790 having three inner surfaces 2792 that define a longitudinal extending channel 2794 therein. The channel 2794 may receive the side members 2732 therein when the displacement member 2710 couples with the guide rails 2726. In this way, the lateral brace mechanism 2788 may contribute to stability of the displacement member 2710 relative to the guide rails 2726 by reducing lateral tilt of the displacement member 2710. It is foreseen that the displacement member 2710 may not include the lateral brace mechanism 2792 and may instead only include the upper member 2784 and the lower tab members 2780. Alternatively, it is foreseen that the displacement member 2710 may not include the upper member 2784 and the lower tab members 2780, but may only include the lateral brace mechanism 2792. Additionally and alternatively, other mechanisms are possible to facilitate the displacement member 2710 displacing between the proximal and distal ends 2718, 2716 of the guide member 2708. For example, the guide member 2708 could include longitudinally extending rods (not shown) and the displacement member 2710 may include a sleeve that engages and is guided by the rods. In such an embodiment, the rods may be adapted to slide within the openings 2770 of the needle receiving ports 2768 with or without modification to the displacement member 2708.

Still referring to FIGS. 32A-32C, flanges 2796 extend laterally from the upside-down U-shaped members 2790, which may act as grasping points for the physician. The flanges 2796 extend inwardly and are coplanar with a back wall member 2798 that spans between the upside-down U-shaped members 2790, the vertically extending member 2760, and the upper members 2784. The back wall member 2798 may function to provide rigidity between the various components of the displacement member 2710. As seen in FIG. 32C, a proximal side 2800 of the needle receiving ports 2768 includes keyed features to lockingly engage the access needle 2712 such that it does not rotate once it is coupled with the port 2768.

Reference is made to FIGS. 33A and 33B, which depict, respectively, a front isometric view and a front view of the lower mount 2704 of the biopsy guide 2700. As previously described, the upper mount coupling mechanism 2714 includes the snap features 2758 to couple with the channel 2756 in the base platform 2722. Each of the snap features 2758 may be vertical flanges 2802 with a lip 2804 at its vertical termination. As the inner surfaces defining the channels 2756 contact the vertical flanges 2802, the inner surfaces compress the lips 2804 together relative to each other until the flanges 2802 "snap" or expand outwardly relative to each other such that the lips 2804 are on a top surface of the base platform 2722. The vertical flanges 2802 extend from the platform 2766 of the upper mount coupling mechanism 2714. The platform 2766 is coupled with the probe coupling mechanism 2706, which, as seen in the figures, may be a snap-grip or snap-clip type of hose or tube clamp. The mechanism 2706 may include a first and a second arm member 2804, 2806 extending from opposite sides 2808 of the platform 2766. The arm members 2804, 2806 are flexible and designed to wrap around a portion of the probe fitted within the opening formed by the first and second arms 2804, 2806. The first arm member 2804 includes a first clamping structure 2810 including an upper row of teeth 2812 and a lower smooth sliding surface 2814. The second arm member 2806 includes a second clamping structure 2816 including an upper smooth sliding surface 2818 and a lower row of teeth 2820. The first and second clamping structures 2810, 2816 work together to provide a clamping or gripping function to securely support the transrectal probe to the lower mount 2704 and, thus, the upper mount 2702.

In operation, a transrectal probe is positioned within the opening between the first and second clamping structures 2810, 2816. The physician may determine a desired position on the probe based on the patient's anatomy, the particular transrectal probe, or the particular procedure to be performed, among other possible criteria. Once a position for the lower mount 2704 is chosen, the physician may cause the first and second arm members 2804, 2806 to be contracted relative to each other by pushing on the outer ends 2822 of the clamping structures 2810, 2816, respectively. As the clamping structures 2810, 2816 converge relative to each other, the lower row of teeth 2820 on the second clamping structure 2806 is received within an opening 2824 formed between the upper row of teeth 2812 and the lower smooth surface 2814. The upper row of teeth 2812 are caused to engage with the lower row of teeth 2820. Additionally, the upper smooth surface 2818 is caused to slide on an inner smooth surface 2826 of the first arm member. And, the lower smooth sliding surface 2814 is caused to slide on a lowest smooth surface 2828 on the second clamping structure 2816. The teeth of the upper and lower row 2812, 2820 are arranged in a saw tooth like manner such that when they are increasingly engaged with each other the teeth grip each other and resist moving in the opposite direction. Once engaged, the teeth may be disengaged by pulling on a tab 2830 on a bottom portion of the first clamping structure 2810. Pulling on the tab 2830 allows the teeth 2812, 2820 to disengage with each other and the flexible nature of the first and second arms 2804, 2806 are caused to spring back into the shape shown in FIG. 33B. As seen in FIGS. 33B-33B, an inner surface 2834 of the first and second arms 2804, 2806 includes a gasket 2832 that may be flexible and deformable to provide for a gripping surface between the probe and the lower mount 2704.

Reference is made to FIG. 34, which depicts a front isometric view of an access needle 2712. As seen in the figure, the needle 2712 includes a distal end 2836 and a proximal end 2838 opposite the distal end 2836. At the distal end 2836 is the bevel 2840 extending distally from a shaft 2842. Within the shaft 2842 is a lumen 2844 for communication of fluids or, in the case of the access needle 2712, a shaft of a smaller gage biopsy needle. The proximal end 2838 of the needle 2712 includes a hub 2846 with ridges 2848 extending longitudinally around a circumference of the hub 2846. The ridges 2848 may engage with corresponding and negatively shaped features on the proximal side 2800 of the needle receiving ports 2768.

The following discussion will focus on use of the biopsy guide 2700 and will refer to FIGS. 35A-35D, which depict, respectively: a front isometric view of the lower mount 2704; a front isometric view of the lower mount 2704 coupled with the upper mount 2702; a front isometric view of the lower mount 2704 coupled with the upper mount 2702 and the displacement member 2710 positioned at a proximal end of the guide member 2708; and, a front isometric view of the lower mount 2704 coupled with the upper mount 2702 and the displacement member 2710 positioned at a proximal end of the guide member 2708 with the access needle 2712 positioned within one of the needle receiving ports 2768.

As seen in FIG. 35A, the lower mount 2704 is positioned with the first and second clamping structures 2810, 2816 of the first and second arm members 2804, 2806 uncoupled such that a transrectal probe may positioned between the arm members 2804, 2806. While it is not depicted in the figures, the first and second clamping structures 2810, 2816 may be engaged with each other or coupled as described previously to grasp the probe between the arm members 2804, 2806 and against the gasket 2832.

As seen in FIG. 35B, the upper mount 2702 may be coupled with the lower mount 2704. More particularly, the vertical flanges 2802 on the platform 2766 of the upper mount coupling mechanism 2714 may be engaged with or snapped together with the channels 2756 on the base platform 2722 of the guide member 2708.

As seen in FIG. 35C, the displacement member 2710 may be engaged with the guide member 2708. More particularly, the distal end 2772 of the displacement member 2710 is longitudinally aligned with the proximal end 2718 of the guide member 2708 such that the proximal ends of the guide rails 2726 are positioned to extend into the corresponding features of the displacement member 2710. That is, the rectangular member 2728 is aligned with the opening between the upper members 2784 and the lower tab members 2780, and the vertically extending side members 2732 are aligned with the channels 2794 between the inner surfaces 2792 of the upside-down U-shaped member 2790 of the displacement member 2710. Once aligned, the displacement member 2710 is displaced, moved, or translated into engagement with the guide member 2708, as seen in FIG. 35C, which depicts the displacement member 2710 in a proximal-most position.

As seen in FIG. 35D, the access needle 2712 is coupled with the displacement member 2710. More particularly, the bevel 2840 and shaft 2842 of the access needle 2712 are extended through the proximal side 2800 of a particular opening 2770 of a needle receiving port 2768 until the hub 2846 of the access needle 2712 engages with the proximal side 2800 of the port 2768. The ridges 2848 of the access needle 2712 may engaged with corresponding features within the opening 2770 of the port 2768 such that the access needle 2712 remains coupled with the displacement member 2710. The access needle 2712 may be restrained from rotating by the ridges 2848. In certain embodiments, the access needle 2712 may be secured to the displacement member 2710 by, for example, a threaded features on the hub 2846 and openings 2770 of the ports 2768 such that the needle 2712 and the displacement member 2710 may be threadably engaged and disengaged with each other.

In the orientation shown in FIG. 35D, the displacement member 2710 and the access needle 2712 are in a proximal-most position or condition. As seen in the figure, in this particular embodiment, the bevel 2840 of the access needle 2712 lies about flush with the planar distal face 2740 of the distal member 2734. In other embodiments or with a different sized needle 2712, the bevel 2840 of the access needle 2712 may extend beyond the distal face 2740 of the distal member 2734 when the displacement member 2710 is in the proximal-most position, or the bevel 2840 of the access needle 2712 may be positioned proximal of the distal face 2740 of the distal member 2734 when the displacement member 2710 is in the proximal-most position.

In certain embodiments where the bevel 2840 of the access needle 2712 does not extend past the distal face 2740 of the distal member 2734, the physician may use the distal member 2734 to manipulate the perineal skin and subcutaneous tissue of the patient while having the displacement member 2710 coupled to the guide member 2708, but while not having the bevel 2840 of the access needle 2712 contact the patient's skin.

Figure 27:
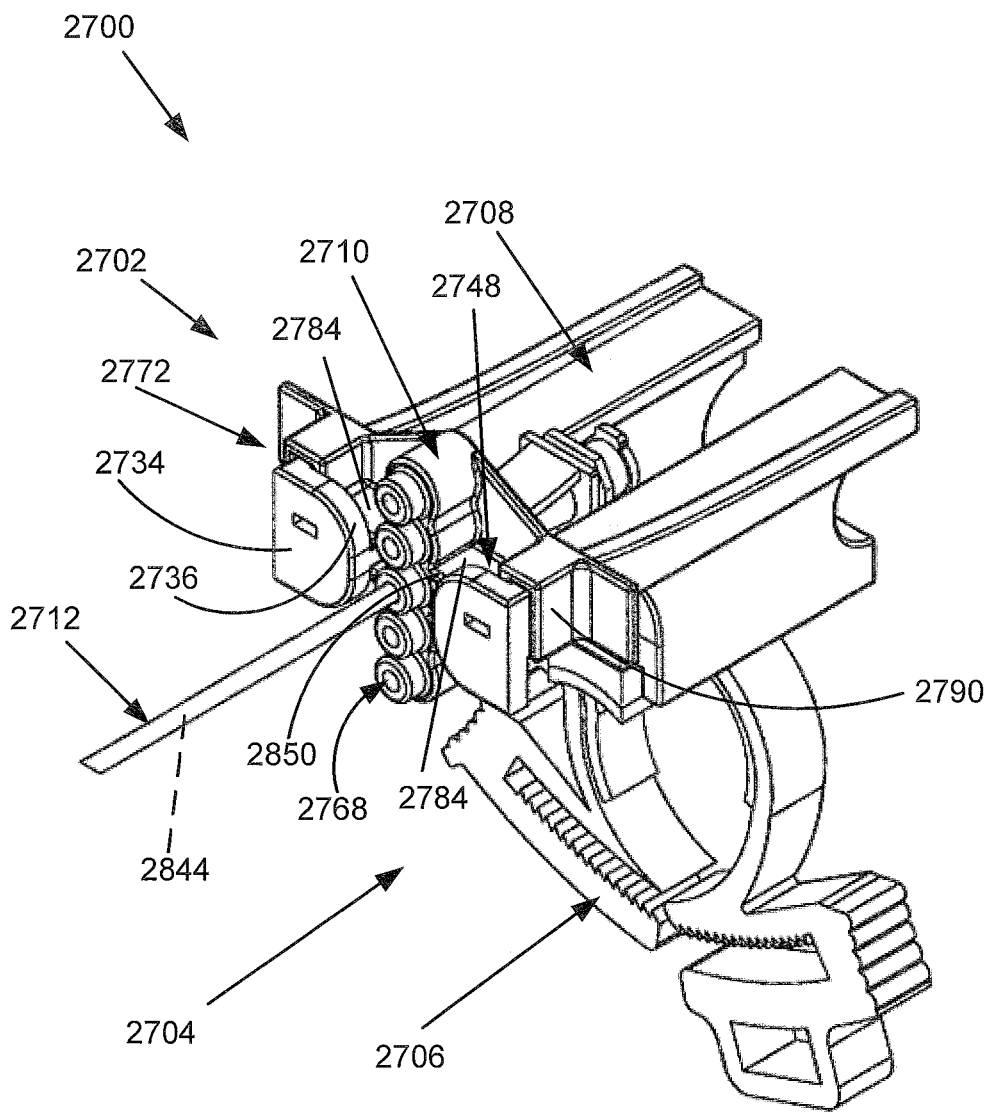
FIG. 27 is an isometric front view of another embodiment of a biopsy guide.
Figure 29:
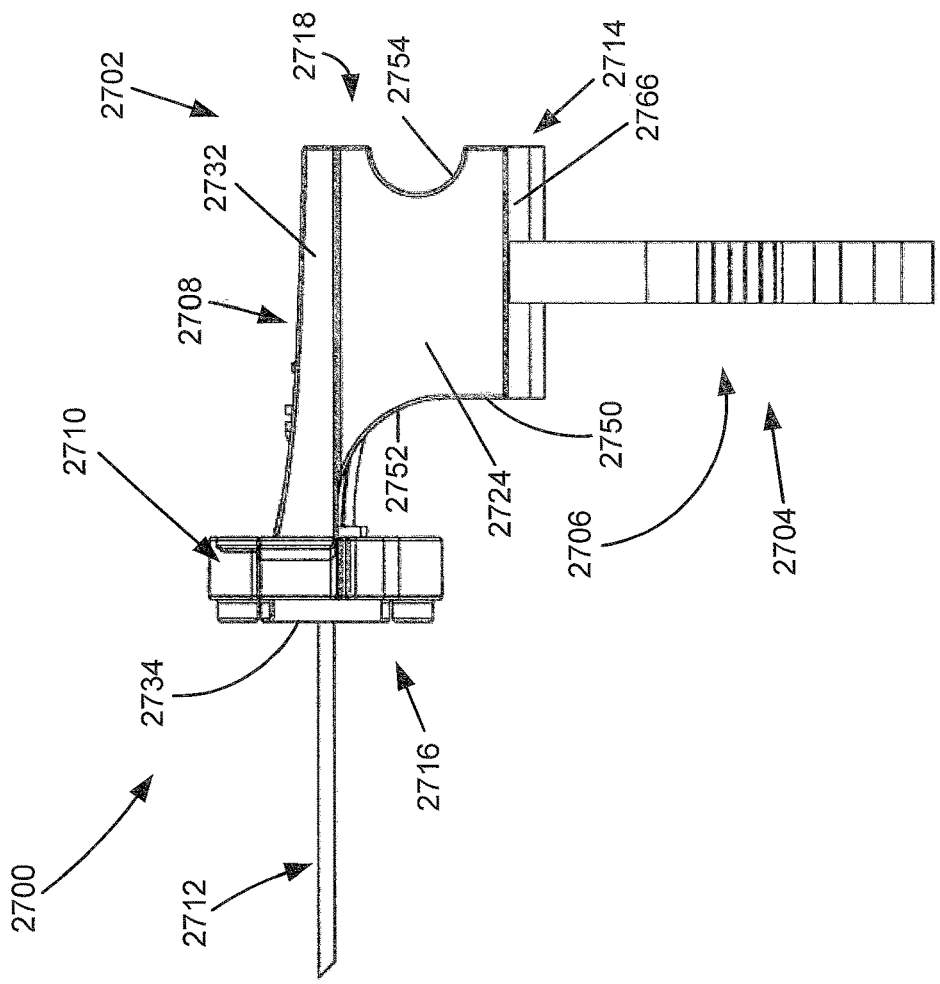
FIG. 29 is a side view of the biopsy guide of FIG. 27.
Figure 28:
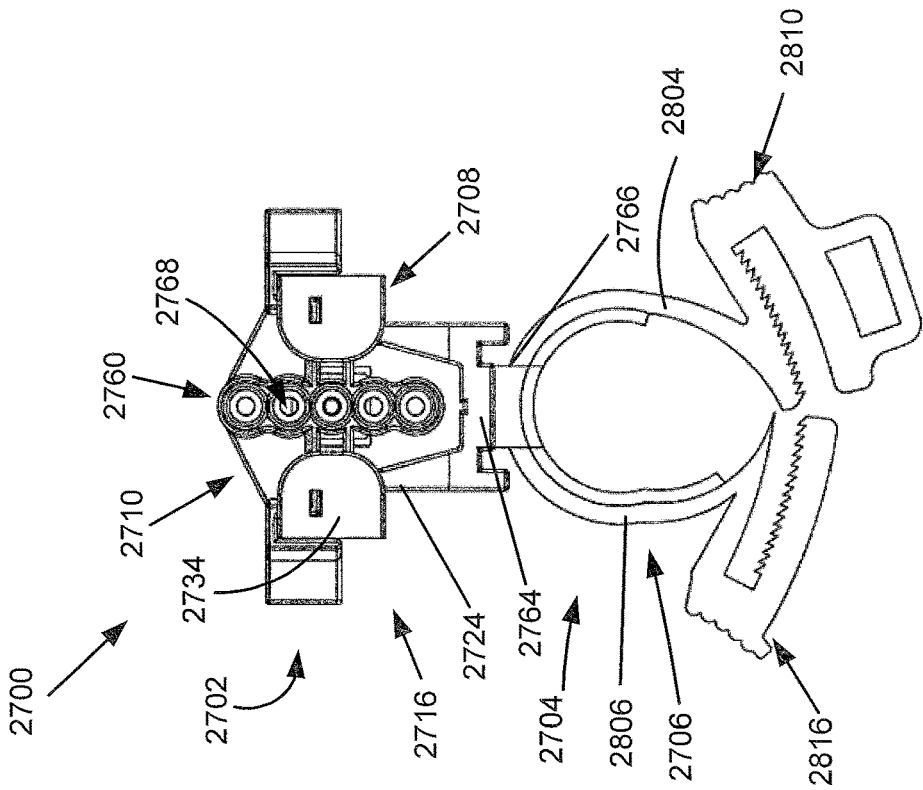
FIG. 28 is a front view of the biopsy guide of FIG. 27.
Figure 30:
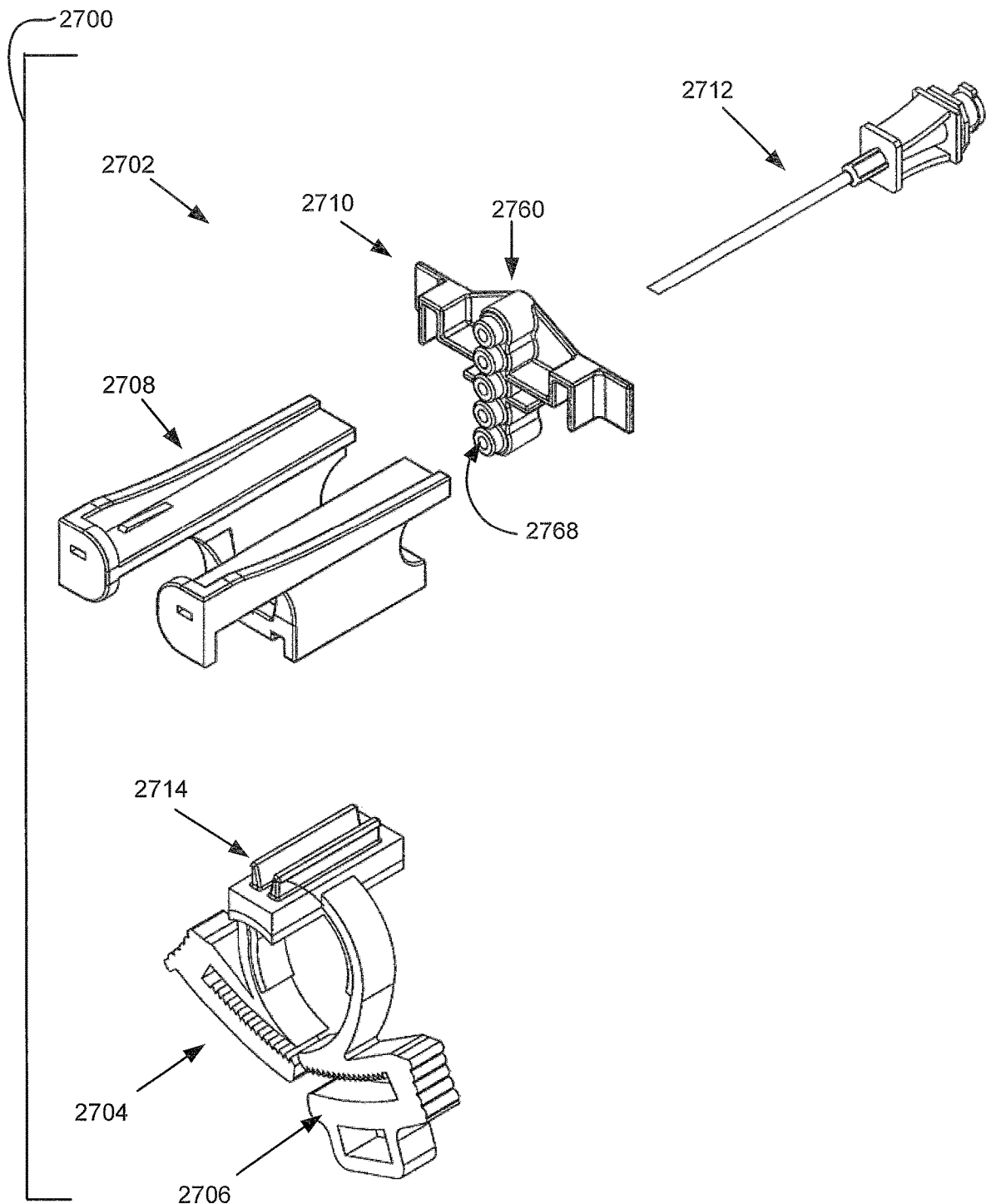
FIG. 30 is an isometric front exploded view of the biopsy guide of FIG. 27.

While FIG. 35D depicts the access needle 2712 coupling with the displacement member 2710 when the displacement member 2710 is in the proximal-most position, the access needle 2712 may be engaged with the displacement member 2710 when the displacement member is at the distal-most position or at any position between the distal-most position and the proximal-most position. When the access needle 2712 is in the proximal-most position, as shown in FIG. 35D, the physician may manipulate the probe and the distal member 2734 of the upper mount 2702 to manipulate the perineal skin and subcutaneous tissue of the patient. When the trajectory of the access needle 2712 is appropriately positioned relative to the patient's perineal skin and subcutaneous tissue, the physician may distally displace the access needle 2712 by pushing on one or more of the back wall member 2798 or flanges 2796 of the displacement member 2710, or the hub 2846 of the access needle 2712. In certain embodiments, the displacement member 2710 may be biased or spring-loaded such that the physician may actuate a mechanism that distally advances the displacement member 2710 and the access needle 2712 without a need for manual advancement by the physician. As the access needle 2712 and the displacement member distally advance or displace, the displacement member 2712 will lock or be secured into the distal-most position via the ramps of the stop feature 2746 positioned on the top surface 2744 of the rectangular member 2728. In the distal-most position, as seen in FIG. 27, the displacement member 2710 is prevented from further distal displacement via the distal member 2734. In particular, a front edge or surface 2850 of the distal end 2772 of the displacement member 2710 abuts or is adjacent a proximal surface 2748 of the distal member 2734 when the displacement member 2710 is in the distal-most position. In certain embodiments, as seen in FIG. 27, the back surface 2748 may abut or be adjacent the front edge or surface 2850 of the upper members 2784, the lower tab members 2780 (not seen in FIG. 27) and/or part of the upside-down U-shaped member 2790.

As further seen in FIG. 27, the distal members 2734 extend inward towards the needle receiving ports 2768 but may define an opening or gap between the rounded inner edges 2736 for the access needle 2712 to extend therethrough.

Once the access needle 2712 is in position in the patient's skin and subcutaneous tissue, the biopsy procedure may continue, as described previously, with the physician extending a biopsy needle through the lumen 2844 of the access needle 2712 and into the patient's prostate. Once procedure is complete, the physician may remove the access needle 2712 from the patient's body by proximally displacing the displacement member 2710 and the access needle 2712 by pulling or pushing on the displacement member 2710 or access needle. Alternatively, the access needle 2712 may be disengaged with the displacement member 2710 while the displacement member 2710 is in the distal-most position.

Figure 36:
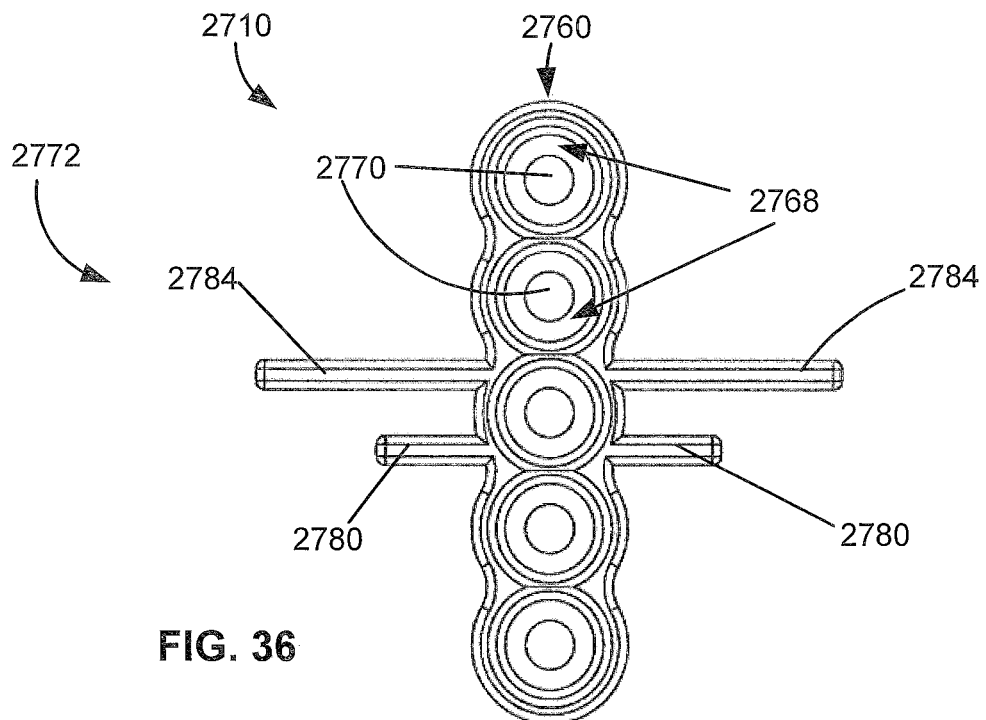
FIG. 36 is a front view of another embodiment of the displacement member.

The discussion will now focus on additional and alternative embodiments of the biopsy guide. As seen in FIG. 36, the displacement member 2710 may include the upper members 2784 and the lower tab members 2780 for engaging with and sliding or displacing relative to the rectangular members 2728 of the guide rails 2726. The displacement member 2710 of FIG. 36, however, does not include an upside-down U-shaped member for engaging with the side members 2732 of the guide rails 2726 and, further, does not include the back wall member 2798 and the flanges 2796. Features of both embodiments of the displacement member 2710 may be combined as needed and without limitation.

The lower mount 2704, as described herein, may take many forms without departing from the scope of the present disclosure. Other mechanisms to couple the upper mount 2702 to the probe are possible and contemplated herein. For example, the upper mount 2702 may couple with or be integrally formed with a thin sheath or sleeve of latex, polyurethane, or other materials, such as a male condom. The sheath may be fitted over the probe in a tight fitting manner such that the upper mount 2702 is secured in position relative to the probe.

Additional or alternative embodiments of the lower mount 2704 may include rubber or rubber-type cinch straps that are coupled with or integral with the upper mount 2702.

The upper mount 2702, as described herein, may take many forms without departing from the scope of the present disclosure. Other mechanisms to guide the access needle 2712 are possible and contemplated herein. For example, the displacement member 2710 supporting the access needle 2712 may be coupled to a platform on a coupler side of a four-bar linkage (e.g., parallelogram linkage) where the fixed portion of the linkage may be coupled with the base platform 2722 of the guide member 2710. The platform may be displaceable distal-proximal by urging the platform distally or proximally, while displacing in an arcuate path. In the case of a parallelogram linkage, the trajectory of the access needle 2712 may remain parallel to the longitudinal axes of the probe and guide member 2710 while vertically displacing. In this way, such a linkage may be used for distal-proximal displacement as well as vertical displacement or adjustment, as needed for a particular biopsy procedure. This type of displacement member 2710 may be used with the guide member 2708 as described herein with or without modification.

As another example, the displacement member 2710 supporting the access needle 2712 may be coupled to a carriage or lead screw nut that is displaced relative to the guide member 2708 (and probe) via rotation of a lead screw. The lead screw may be positioned parallel to the longitudinal axis of the guide member 2708 and the probe such that displacement of the lead screw nut and, thus, the displacement member 2710 and access needle 2712 displace or translate distal-proximal while maintaining a trajectory of the access needle 2712 that may be fixed. A bottom side of the lead screw nut may include a feature or protrusion that extends into a channel formed in the base platform 2722 of the guide member 2708 such that the lead screw nut does not rotate, but, rather, displaces or translates linearly distal-proximal in response to rotation of the lead screw. The lead screw may be rotatable by hand via, for example, a handle at the proximal end of the lead screw.

Figure 37A:
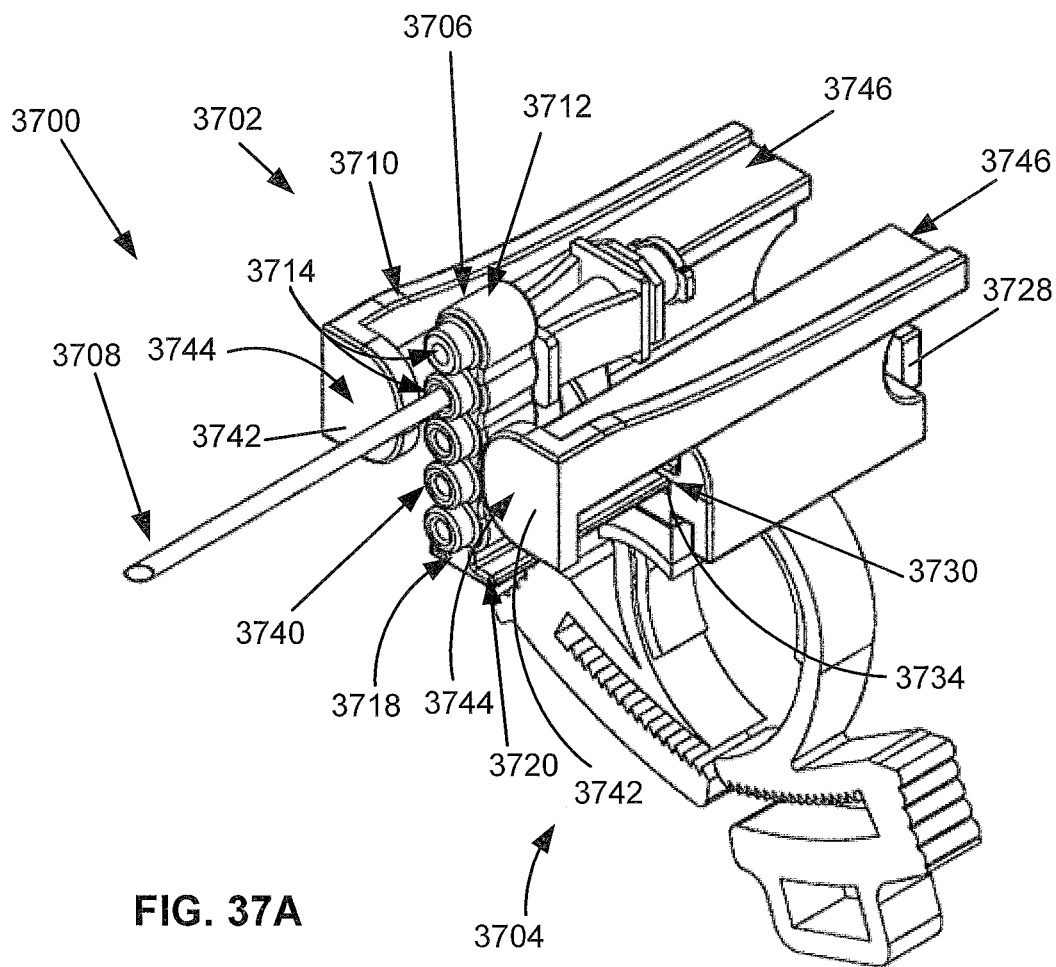
FIG. 37A is an isometric front view of another embodiment of the biopsy guide.
Figure 37B:
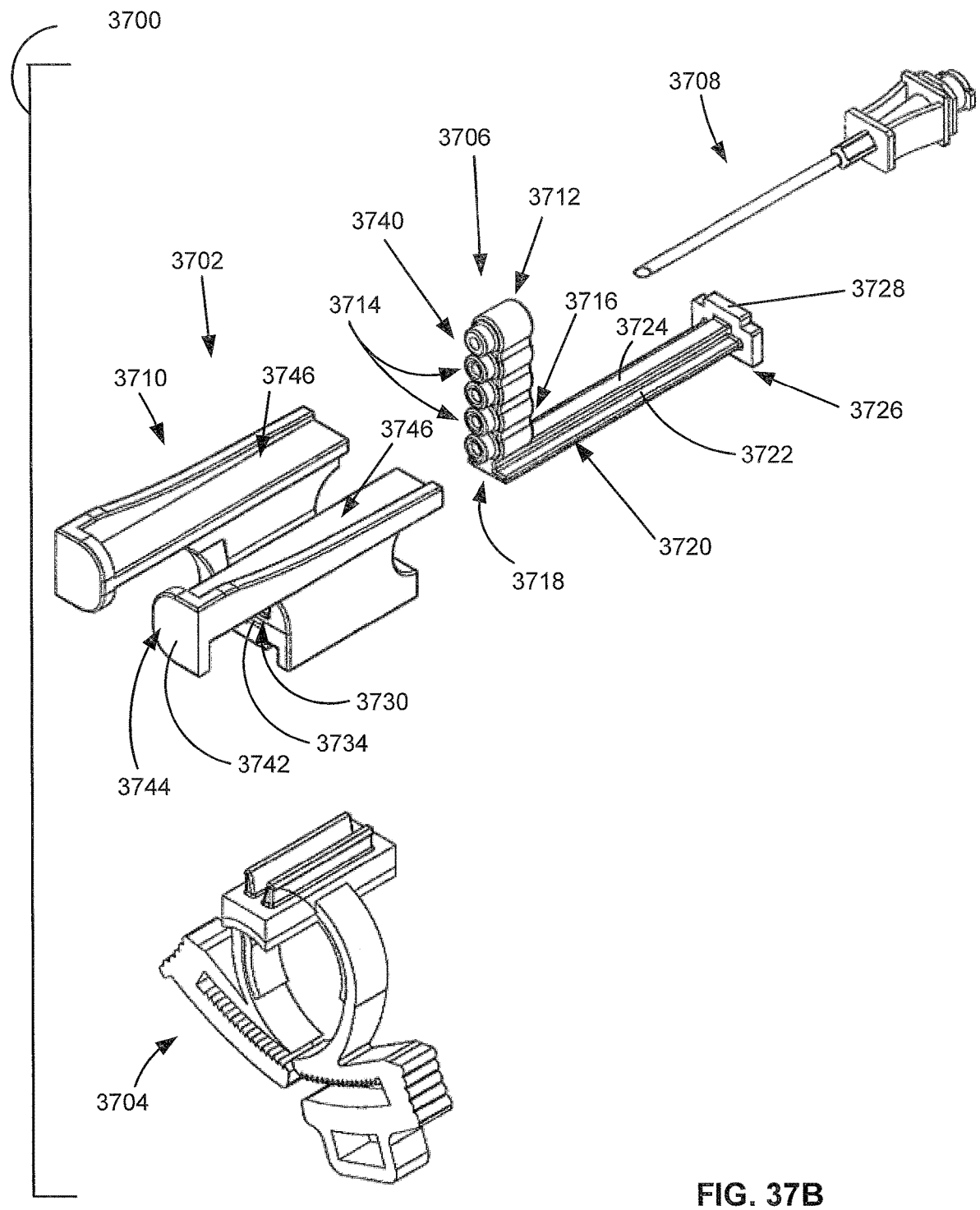
FIG. 37B is an isometric front exploded view of the upper mount of the biopsy guide of FIG. 37A.
Figure 37C:
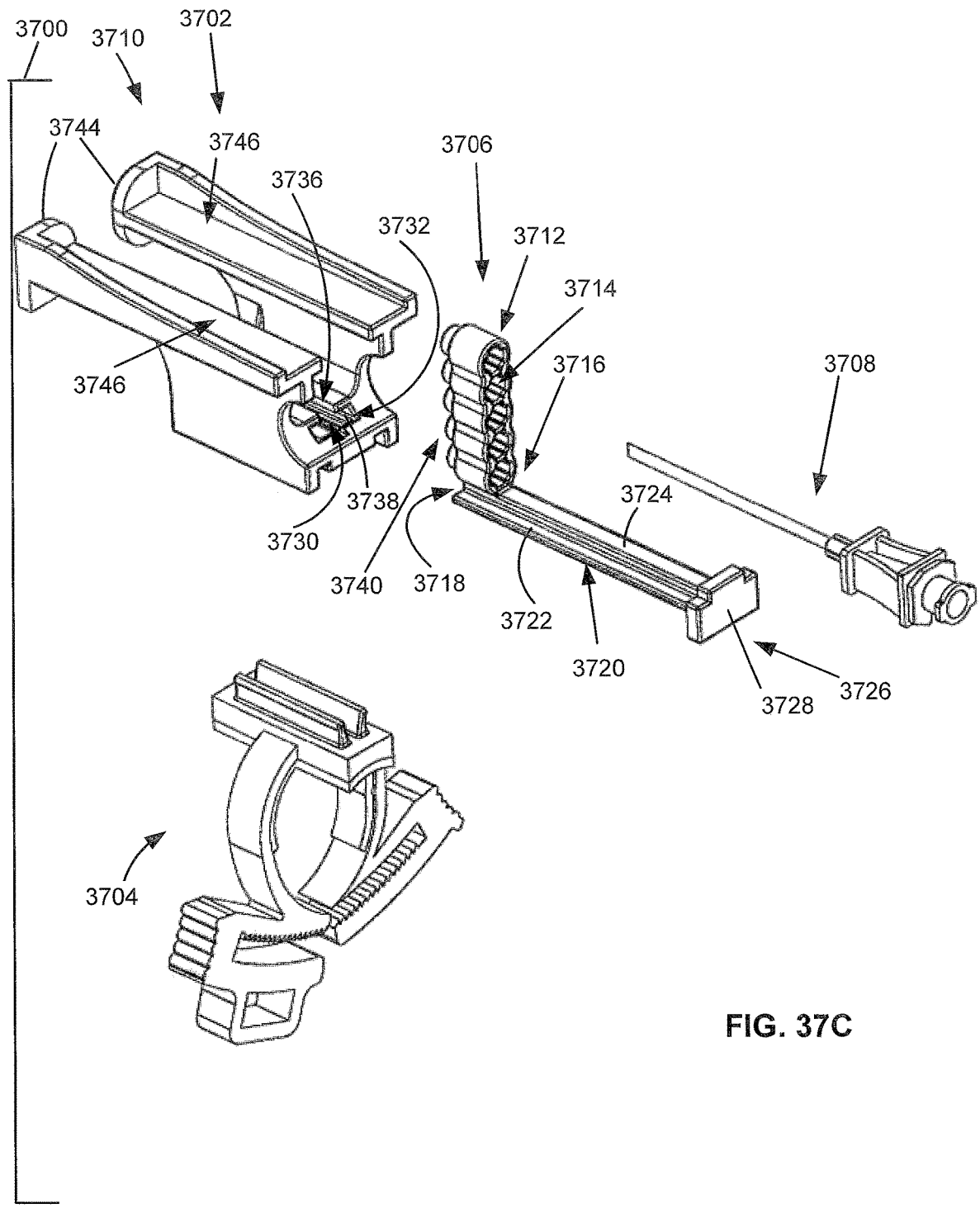
FIG. 37C is an isometric back exploded view of the upper mount of the biopsy guide of FIG. 37A.

Reference is now made to FIGS. 37A-37F, which depict various views of another embodiment of the biopsy guide 3700. As seen in FIG. 37A, which is a front isometric view of the biopsy guide 3700, the guide 3700 is similar to previously described embodiments of the guide in that it includes an upper mount 3702 and a lower mount 3704. The lower mount 3704 is adapted to secure the guide 3700 to a transrectal probe and includes the same features as the previously described embodiment. The upper mount 3702 may releasably couple with the lower mount 3704. As seen in FIGS. 37B and 37C, which are, respectively, front and back isometric exploded views of the upper mount 3702, the biopsy guide 3700 further includes a guide member 3710 and a displacement, sliding, or translating member 3706 that is adapted to couple with an access needle 3708.

As seen in FIGS. 37B-37C and 37E-37F, the displacement member 3706 includes a vertically extending member 3712 having five needle receiving ports 3714 formed within the member 3712. The ports 3714 may receive the access needle 3708 within any of the ports 3714, as previously described, to vary the height of the access needle 3708 relative to the probe (not shown). The access needle 3708 may couple with the needle receiving ports 3714 such that they may be displaced together relative to the guide member 3710.

As seen in the figures, a bottom end 3716 of the vertically extending member 3712 is coupled to a distal end 3718 of a rail member 3720 that may slidingly engage with the guide member 3710. The rail member 3720 includes a flange member 3722 and a web member 3724 arranged in a T-beam shape. That is, the flange member 3722 is wider than the web member 3724, which projects upward and substantially perpendicularly from a central portion of the flange member 3722. From the distal end 3718, the rail member 3720 extends proximally to a proximal end 3726. At the proximal end 3726 is an end plate member 3728, which prevents distal displacement of the displacement member 3706 past a certain point.

As seen in FIGS. 37C and 37D, the guide member 3710 includes a rail receiving slot or channel 3730 having a proximal opening 3732, a distal opening 3734 (seen in FIG. 37B), and a top opening 3736. The rail receiving slot 3730 is generally a negative shape of the rail member 3720 and may receive the rail member 3720 therein and permit the rail member 3720 and, thus, the displacement member 3706 and access needle 3708 to displace relative to the guide member 3710. When the rail member 3720 is positioned within the rail receiving slot 3730, inner surfaces 3738 of the slot 3730 may contact the flange and web members 3722, 3724 and restrain the displacement member 3706 from lateral displacement and vertical tilting while allowing distal-proximal displacement or translation of the displacement member 3706. Thus, the displacement member 3706 may be displaced or translated distally and proximally while maintaining alignment of a trajectory of the access needle 3708 substantially parallel with a longitudinal axis of the probe when the biopsy guide 3700 is coupled with the probe.

As seen in FIG. 37A, the displacement member 3706 is in a distal-most position with the distal end 3718 of the rail member 3720 and a distal end 3740 of the vertically extending member 3712 being about coplanar with a distal face 3742 of a distal member 3744 of the guide rail members 3746, which may be similar to as previously described in relation to previous embodiments. In the distal-most position, the rail member 3720 extends past the distal opening 3734 of the rail receiving slot 3730, and the end plate member 3728 of the rail member 3720 abuts or is adjacent the proximal opening 3732 of the rail receiving slot 3730. To proximally displace the displacement member 3706 from the distal-most position, the physician may pull or push on the end plate member 3728, the vertically extending member 3712, or the access needle 3708.

It is noted that the guide rail members 3746 and, more particularly, the distal members 3744 may be used by the physician to manipulate the perineal skin and subcutaneous tissue of the patient, as described previously. And while the embodiment of the biopsy guide 3700 in FIGS. 37A-37F describe a rail and slot type of arrangement between the displacement member 3706 and the guide member 3710, other mechanisms are possible to displace the displacement member 3706 relative to the guide member 3710. Additionally or alternatively, features and elements from other embodiments of the biopsy guide may be incorporated into the present embodiment without limitation. Similarly, features and elements from the present embodiment of the biopsy guide may be incorporated into any of the other embodiments of the biopsy guide without limitation.

As seen in FIG. 37G, which is a side view of another embodiment of the displacement member 3706 with the access needle 3708 partially positioned within the top needle receiving port 3714 of the vertically extending member 3712, the rail member 3720 may be replaced by a lead screw 3748 and the bottom end 3716 of the vertically extending member 3712 may include a lead screw nut 3750 that rotationally engages with the lead screw 3748 to cause the displacement member 3706 and the access needle 3708 to displace or linearly translate relative to the probe and the guide member 3710 (not shown). The lead screw 3748 may be rotationally coupled with bearings 3752 at opposite ends which allow the lead screw 3748 to rotate thereon. The lead screw nut 3750 may be prevented from rotating by a guide rail 3754 that extends between the bearings 3752 and also extends through a passageway in the lead screw nut 3750. In this way, as the lead screw 3748 rotates, the lead screw nut 3750, as well as the vertically extending member 3712 and the access needle 3708, are caused to displace or translate distal-proximal because the lead screw nut 3750 is prevented from rotating by the guide rail 3754. The lead screw 3748 may include a handle 3756 for rotating the lead screw 3748. The displacement member 3706 shown in FIG. 37G may be coupled with the guide member 3710 shown in the previous figures such that the lead screw 3748 is generally parallel with the longitudinal axis of the guide member 3710 and the probe. The displacement member 3706 may, for example, couple with the base platform of the guide member 3710 at the bearings 3752, or at other parts of the member 3706.

As seen in FIGS. 37H-37I, which are, respectively, an isometric front view and a side view of another embodiment of the biopsy guide 3900, it includes a probe coupling mechanism 3902 in the form of collars that may be adjustably secured to the probe 3904. Four arm members 3906 are pivotally coupled at bottom ends 3908 to the probe coupling mechanism 3902 and pivotally coupled at top ends 3910 to a platform member 3912. The arm members 3906 may be of equal length such that the platform member 3912 is capable of displacing distal-proximal while maintaining a parallel orientation relative to the probe 3904. More particularly, as seen in FIG. 37I, the platform member 3912 may include a longitudinal axis that is generally parallel to a longitudinal axis of the probe 3904 in all distal-proximal orientations of the platform member 3912 relative to the probe 3904. The platform member 3912 may include a longitudinally extending channel 3914 for receiving and guiding a displacement member 3916 having a needle receiving port 3918. The displacement member 3916 may include a flanged lower body portion 3920 that matches a shape of the channel 3914 such that the displacement member 3916 may slide within the channel 3914 or displace relative to the platform member 3912 while maintaining an orientation of a needle positioned within the needle receiving port 3918 that is generally parallel to the longitudinal axis of the probe 3904.

As seen in FIG. 37I, the biopsy guide 3900 may function as a four bar parallel or parallelogram linkage during displacement of the platform member 3912. In particular, FIG. 37I shows three positions of the platform member 3912 as it displaces. A first position 3922 shows the platform member 3912 at a highest position relative to the probe 3904 where the arm members 3906 are vertically extended to their maximum. A second position 3924 shows the platform member 3912 as it distally displaces while rotating clockwise and lowering the platform member 3912 relative to the probe. A third position 3926 shows the platform member 3912 as it further distally displaces while rotating clockwise and lowering the platform member 3912 relative to the probe. As seen in all positions 3922, 3924, 3926, a longitudinal axis of the platform member 3912 may remain generally parallel with a longitudinal axis of the probe 3904.

Reference is now made to FIG. 37J, which is a front isometric view of another embodiment of an upper mount 4000. As seen in the figure, the upper mount 4000 includes a guide member 4002 that is similar to previously described embodiments in that it includes a pair of guide rails 4004 that extend longitudinally and are spaced apart from each other. This embodiment of the upper mount 4000, however, does not include a displacement member. Rather, the guide mount 4002 of the upper mount 4000 of FIG. 37J includes a vertically oriented member 4008 including needle receiving ports 4006 that are also vertically aligned. The member 4008 may not be displaceable relative to the guide member 4002 in this particular embodiment.

That is, the needle receiving ports 4006 may align a trajectory of an access needle in any of the ports 4006 such that a trajectory of the access needle may be generally parallel to a longitudinal axis of the probe. The needle receiving ports 4006 may be integrally formed with the guide member 4002. Or, the vertical member 4008 including the needle receiving ports 4006 may be releasably coupled to the guide member. In a releasable arrangement, the vertical member 4008 may be coupled with the guide member via any coupling mechanism described herein or known in the art. As seen in the figure, the needle receiving ports 4006 are cylindrical and extend generally from a proximal end 4010 to a distal end 4012 of the guide member 4002. The distal tip 4014 of the needle receiving ports 4006 may be about coplanar with a distal face 4016 of the distal members 4018 of the guide rails 4004.

Reference is made to FIGS. 37K-37L, which are, respectively, front and side views of another embodiment of a biopsy guide 4100. As seen in the figures, the biopsy guide 4100 includes displacement member 4102 including a vertically oriented body 4104 having five vertically aligned needle receiving ports 4106 for receiving, supporting, and orienting an access needle. At a bottom end 4108 of the vertical body 4104 is a probe coupling mechanism 4110 including a collar 4112 having a guide rail or protrusion 4114 extending from an inner surface 4116 of the collar 4112. The guide rail 4114 extends longitudinally in the collar 4112 and may be received by a correspondingly shaped channel or slot 4120 in a transrectal probe 4118. In this way, the displacement member 4102 may slide, displace, or translate relative to the probe 4118 while being restrained from certain movements by the interaction between the guide rail 4114 and the channel 4120. As such, the access needle supported by the needle receiving port 4106 may displace or translate distal-proximal relative to the probe 4118 while maintaining a trajectory that is generally parallel with a longitudinal axis of the probe 4118.

The inner surface 4116 may include roller bearings or similar structures to permit the collar 4112 to roll, translate, or displace relative to the probe 4118. While the channel 4120 is described as being formed in the probe 4118, the channel 4120 may be formed in a separate member that is coupled to the probe 4118. In this case, a specialized probe having a channel may not be needed; rather, any off-the-shelf ultrasound probe may be used with the separate member having the channel 4120 to utilize the biopsy guide 4100 of the present embodiment.

Reference is made to FIGS. 37M-37U, which depict various views of alternative embodiments of the lower mount. To begin, reference is made to FIGS. 37M-37Q. FIG. 37M is a front isometric view of a biopsy guide 4200. FIG. 37N is a front view of the biopsy guide 4200. FIG. 37O is a front isometric view of a cinch strap 4202. FIG. 37P is a front isometric view of a V-block insert 4204. FIG. 37Q is a front view of the biopsy guide 4200 of FIG. 37M with an insert 4204 of FIG. 37P.

As seen in FIG. 37M, the biopsy guide 4200 includes an upper mount 4206 and a lower mount 4208. The upper mount 4206 may include a base platform 4210 and a pair of guide rails 4212 extending longitudinally from the base platform 4210. The guide rails 4212 may guide a displacement member (not shown), which may support an access needle (not shown), as described in previous embodiments. The lower mount 4208 may include a cinch strap 4202, as shown in FIG. 37), which may include a flange 4214 at one end 4216 and a series of transversely extending ridges 4218. The cinch strap 4202 may be fitted or positioned within a slot 4220 in the base platform 4210 such that the flange 4214 abuts the surfaces of the slot 4220 and is prevented from extending through the slot 4220. The cinch strap 4202 may be fitted around the transrectal probe 4222 and positioned within a locking opening 4224 opposite the slot 4220 in the base platform 4210. The cinch strap 4202, which may be rubber or otherwise made of a flexible material, may be pulled tightly at the free end 4226 such that the ridges 4218 are progressively locked by the locking opening 4224. Once appropriately tightened, the upper mount 4206 is now secured to the probe 4222.

As seen in FIGS. 37P-37Q, the lower mount 4208 of the biopsy guide 4200 may include a V-block insert 4204 positioned between the probe 4222 and the cinch strap 4202. The V-block insert 4204 may include a pair of slots 4228 on opposite sides of the insert 4204 that may be sized to receive the cinch strap 4202 therethrough to secure the V-block insert 4204 into position relative to the cinch strap 4202. The V-block insert 4204 ensures at least three points of contact between the probe and the biopsy guide 4200: one point of contact between the probe 4222 and an underside of the base platform 4210; and, two points of contact between the probe 4222 and the V-block insert 4204.

Figure 37R:
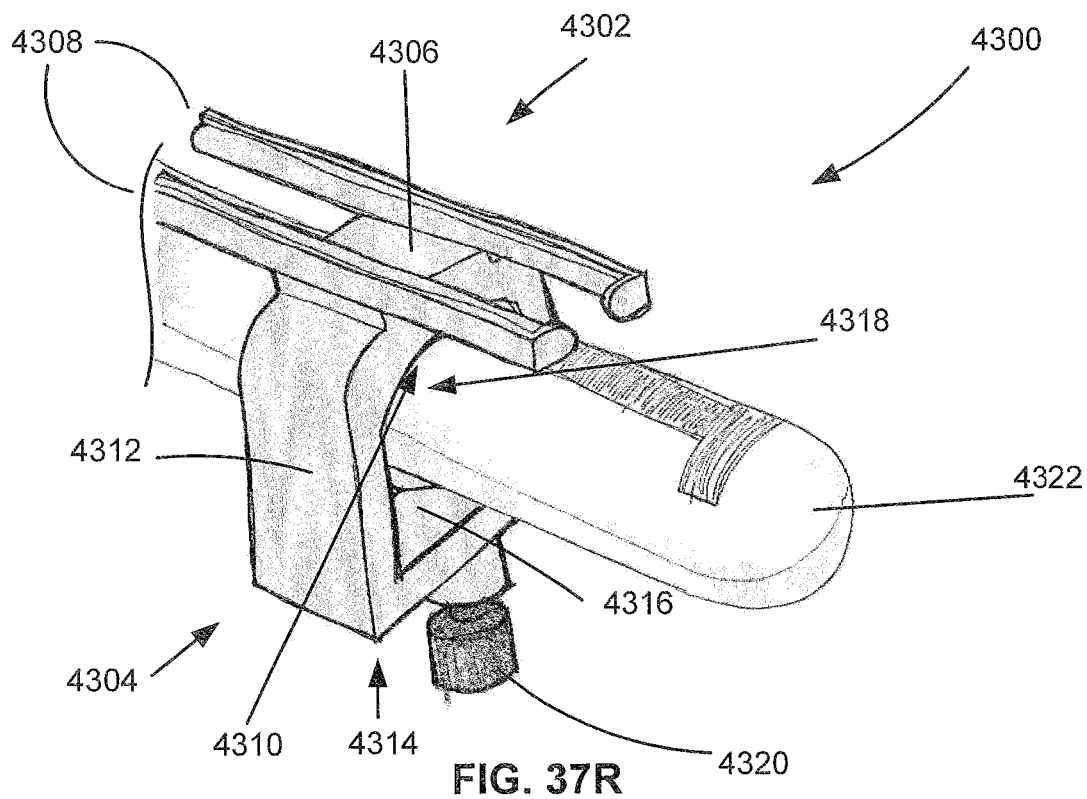
FIG. 37R is a front isometric view of another embodiment of a biopsy guide.
Figure 37S:
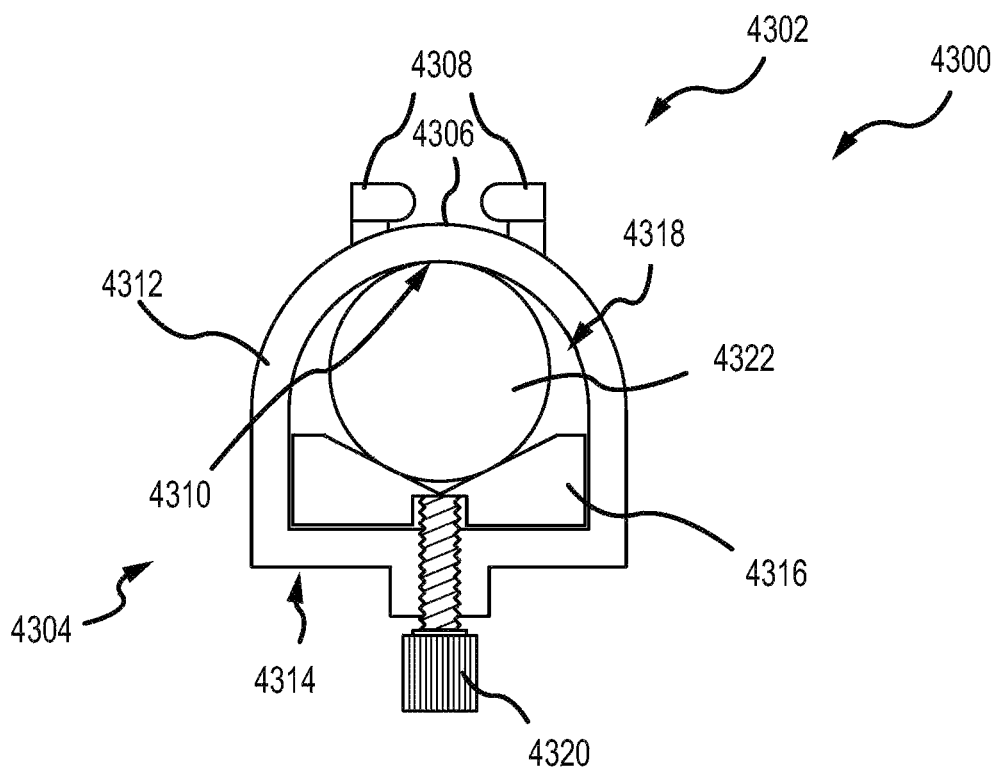
FIG. 37S is a front view of the biopsy guide of FIG. 37R.

Reference is made to FIGS. 37R-37S, which depict, respectively, a front isometric view and a front view of another embodiment of a biopsy guide 4300. Similar to the previously described embodiments, the biopsy guide 4300 includes an upper mount 4302 and a lower mount 4304. The upper mount 4302 may include a base platform 4306 and a pair of guide rails 4308 extending longitudinally and spaced apart from each other. The guide rails 4308 may guide a displacement member (not shown), which may support an access needle (not shown), as described in previous embodiments. The lower mount 4304 may include a curvilinear shaped inner surface 4310 opposite the base platform 4306 and pair of opposing arms 4312 extending downward. The arms 4312 may converge on a bottom side 4314 of the lower mount 4304. A V-block insert 4316 may be positioned an opening 4318 of the lower mount 4304. The opening 4318 may be sized and shaped to receive the transrectal probe 4322 therein. The V-block insert 4316 may be vertically adjustable within the opening 4318 via a thumb-screw 4320. When actuated or rotated, the thumb-screw 4320 may push the V-block insert 4316 vertically to exert a force on the probe 4322, which, in turn, exerts a force on the inner surface 4310 of the base platform 4306 of the lower mount 4304.

Figure 37T:
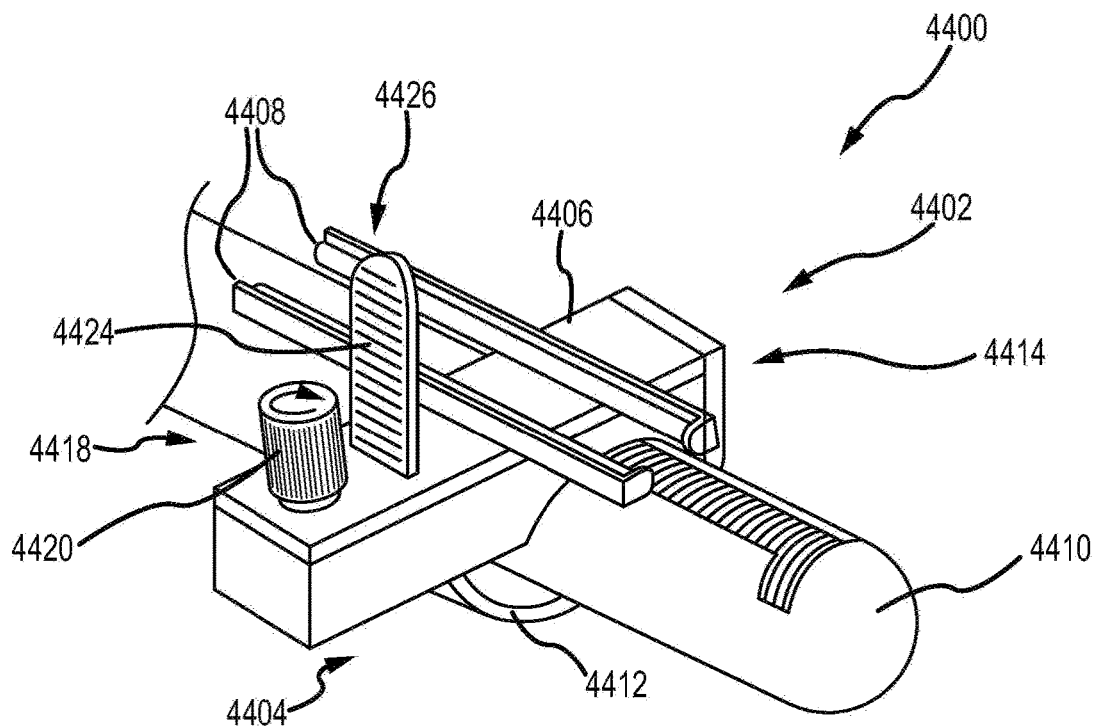
FIG. 37T is a front isometric view of another embodiment of a biopsy guide.
Figure 37U:
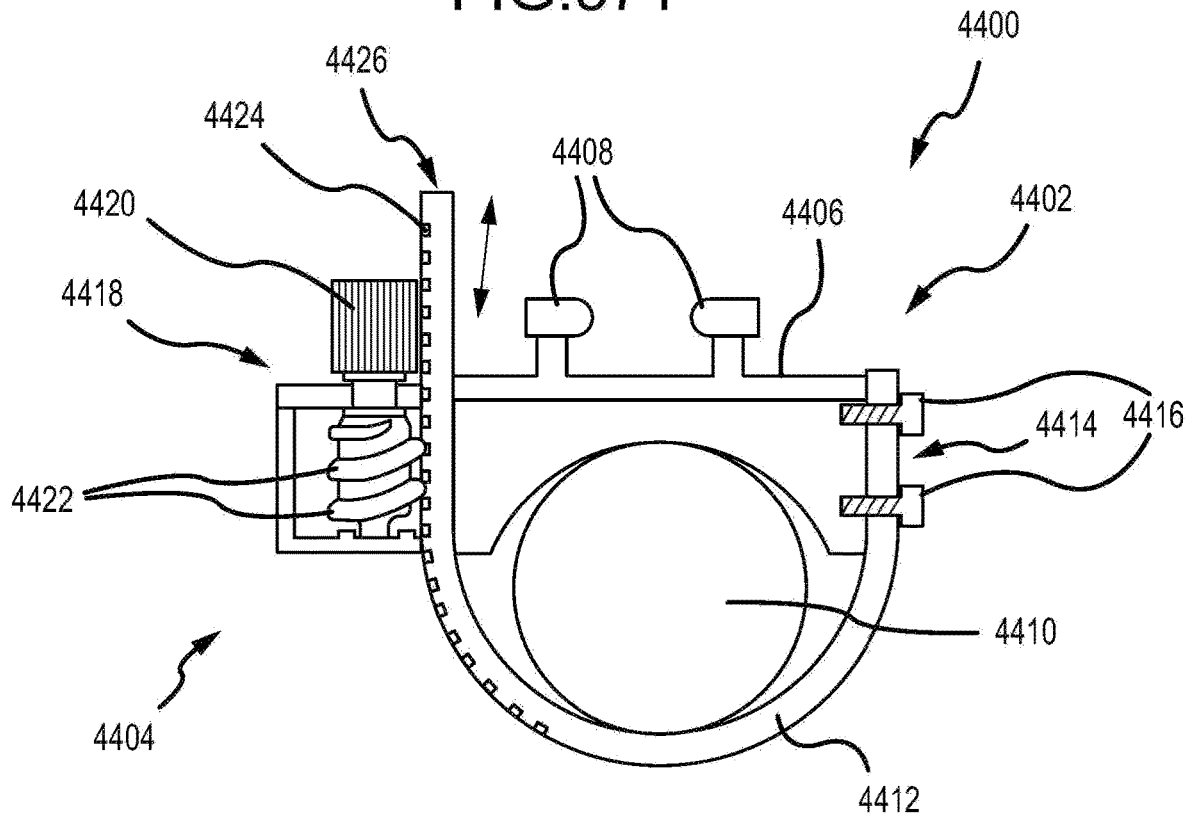
FIG. 37U is a front view of the biopsy guide of FIG. 37T.

Reference is made to FIGS. 37T-37U, which depict, respectively, a front isometric view and a front view of another embodiment of a biopsy guide 4400. As seen in the figures, the device 4400 includes an upper mount 4402 and a lower mount 4404. The upper mount 4402 may include a base platform 4406 and a pair of guide rails 4408 extending longitudinally and spaced apart from each other. The guide rails 4408 may guide a displacement member (not shown), which may support an access needle (not shown), as described in previous embodiments. The lower mount 4404 couples the upper mount 4402 to the probe 4410 and may include a strap 4412 that is affixed at one side 4414 via a pair of fasteners (e.g., screws, bolts) 4416. The strap 4412 may wrap around the probe 4410 and be secured in place via a worm gear mount 4418. The worm gear mount 4418 may include a thumb-knob 4420 that is rotatable and extending to a threaded feature (e.g., ACME threads) 4422 that threadably engage with slots 4424 on the second end 4426 of the strap 4412. As the thumb-knob 4420 is tightened, the thread feature 4422 advances on the slots 4424 and pulls the strap 4412 tighter on the probe 4410 (similar to a hose clamp). This embodiment may include a V-block insert (not shown). As seen in the figures, an underside 4426 of the base platform 4406 may be curvilinear to match the shape of the probe 4410. These features among features from other embodiments may be combined as needed to modify any of the features of any of the biopsy guides described herein.

Figure 37V:
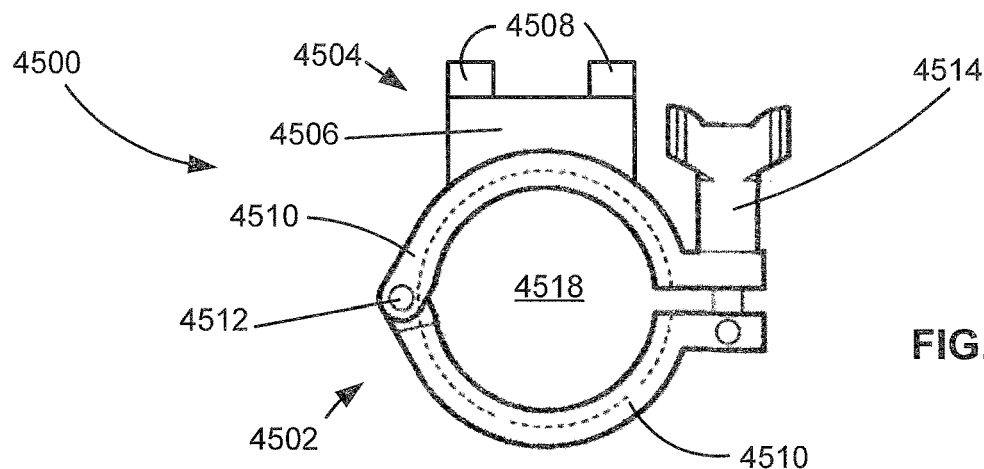
FIG. 37V is a front view of another embodiment of a lower mount.
Figure 37W:
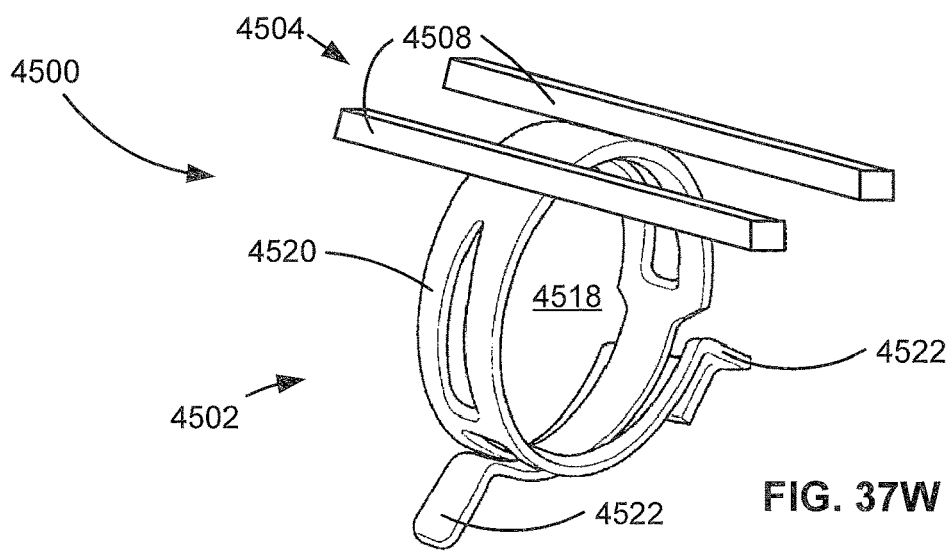
FIG. 37W is an isometric front view of another embodiment of a lower mount.
Figure 37X:
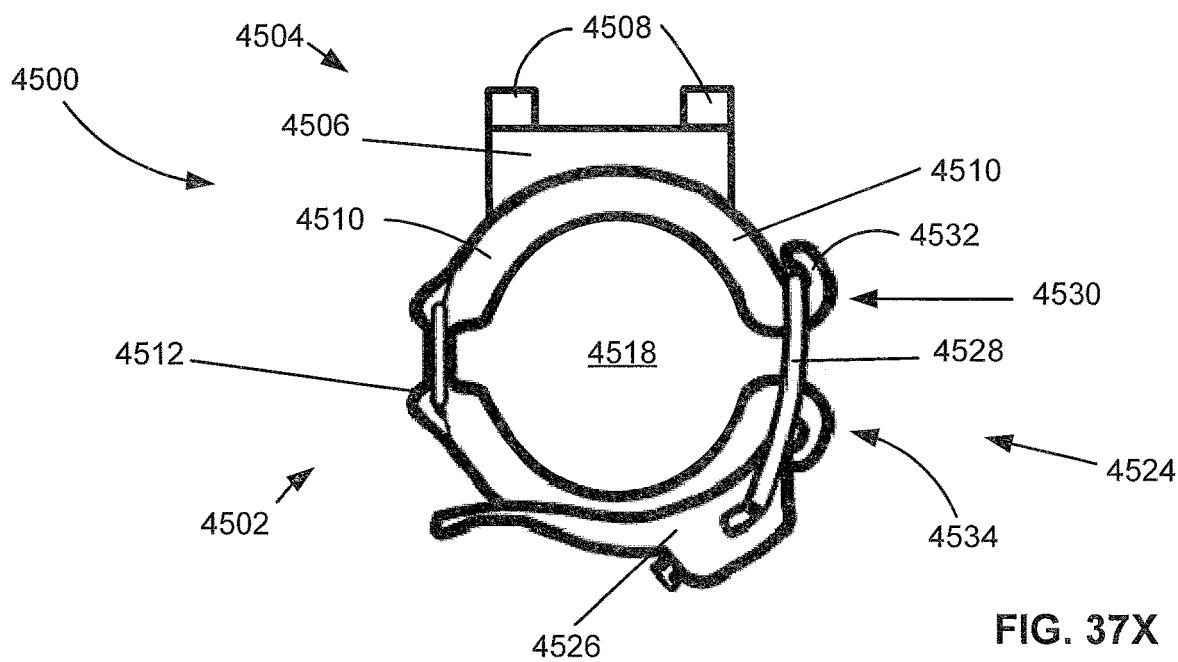
FIG. 37X is a front view of another embodiment of a lower mount.

Reference is made to FIGS. 37V-37X, which depict additional and alternative embodiments of a lower mount 4502 of a biopsy guide 4500. As seen in FIG. 37V, which is a front view of a lower mount 4502, the upper mount 4504 may be similar to previously describe embodiments in that it includes a base platform 4506 and a pair of guide rails 4508. The lower mount may include a pair of semi-circular arm members, clamps, or collars 4510 that are pivotally coupled together at a joint 4512 (e.g., pin). The pair of semi-circular arm members 4510 may open and close about the joint 4512 in a clam-shell type manner. Opposite the joint 4512, the arm members 4510 are adjustably secured together via a thumb-screw 4514 that extends between a pair of flanges 4516. Thus, turning the thumb-screw 4514 in a first direction may cause the pair of arm members 4510 to constrict against a probe (not shown) positioned within the opening 4518 between the arm members 4510. And, turning the thumb-screw 4514 in a second direction may cause the pair of arm members 4510 to loosen against the probe positioned within the opening 4518.

FIG. 37W depicts a front isometric view of the lower mount 4504 including a flexible spring band or biasing collar 4520 extending circumferentially and terminating in a pair of flanges or tabs 4522 that may be compressed together, relative to each other, to selectively enlarge the opening 4518. The probe (not shown) may be positioned within the opening 4518 and the spring band 4520 may compress against the probe and cause a constant force to be exerted on the probe, allowing it to be used on probes of multiple diameters. The flat spring band 4520 may be replaced by a wire spring band (i.e., dumbbell clamp) without departing from the scope of the disclosure.

FIG. 37X depicts a front view of a lower mount 4504 having a pair of semi-circular arm members, clamps, or collars 4510 that are pivotally coupled together at a joint 4512 (e.g., pin). The pair of semi-circular arm members 4510 may open and close about the joint 4512 in a clamshell type manner. Opposite the joint 4512, the arm members 4510 are adjustably secured together via a snap-clip, ratchet, or clamp assembly 4524 including a lever arm handle 4526 a wire arm or loop 4528. The lever arm handle 4526 is attached to one free end 4534 of the arm members 4510 and the wire arm 4528 is attached to the lever arm handle 4526. The other free end 4530 of the other arm member 4510 includes a lip 4532 such that the wire arm 4528 may be fitted around the lip 4532 with the lever arm handle 4526 in an opened position. Once the wire arm 4528 is positioned within the lip 4532, the lever arm handle 4526 may be pivoted towards the arm member 4510, which pulls the free ends 4534, 4530 together to secure the arm members 4510 against the probe (not shown). To remove the probe from the lower mount 4504, the lever arm handle 4526 may be pivoted outward away from the arm member 4510 of the free end 4534 and the arm members 4510 will expand relative to each other and release the probe.

As with many of the embodiments of the biopsy guide described herein, there may be a particular type of mechanical arrangement between the guide member and the displacement member that at least facilitates the displacement of the access needle along at least a portion of the length of the guide member. As discussed in relation to each of the embodiments, the mechanical arrangement may include at least one of a sliding arrangement, a lead screw, or a parallel bar linkage. And, as described with reference to the various embodiments of the biopsy guide, the guide member may operably couple with the transrectal probe via at least one of a sheath arrangement, a ratchet arrangement, a biased collar arrangement, a flexible strap arrangement, a clamping arrangement, or a clamshell collar arrangement.

Reference is now made to FIGS. 38A-38D, which depict, respectively, a transverse plane or slice image of a prostate 3800 and a urethra 3804, a sagittal plane or slice image of a prostate 3800 and a urethra 3804, a transverse plane or slice image of a prostate 3800 and a urethra 3804 with a marking device 3824 positioned within the urethra 3804, and a sagittal plane or slice image of a prostate 3800 and a urethra 3804 with a marking device 3824 positioned within the urethra 3804. As mentioned previously, during a prostate biopsy procedure it may important for the physician to identify the path of the urethra so that he or she can avoid puncturing the urethra with the access needle and the biopsy needle. The biopsy guides described herein may be used with various systems to locate the urethra via the transrectal probe in sagittal and axial planes.

Figure 38A:
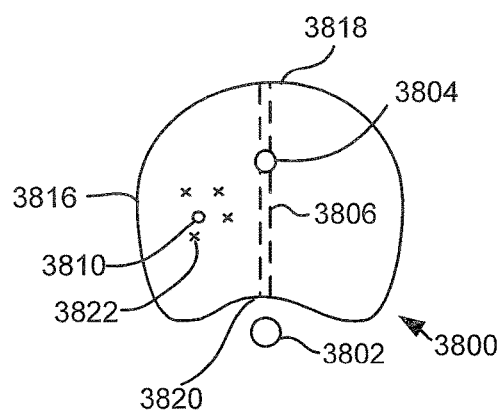
FIG. 38A is a transverse plane or slice view of a prostate depicting the urethra and an access site for penetration of the access needle.
Figure 38B:
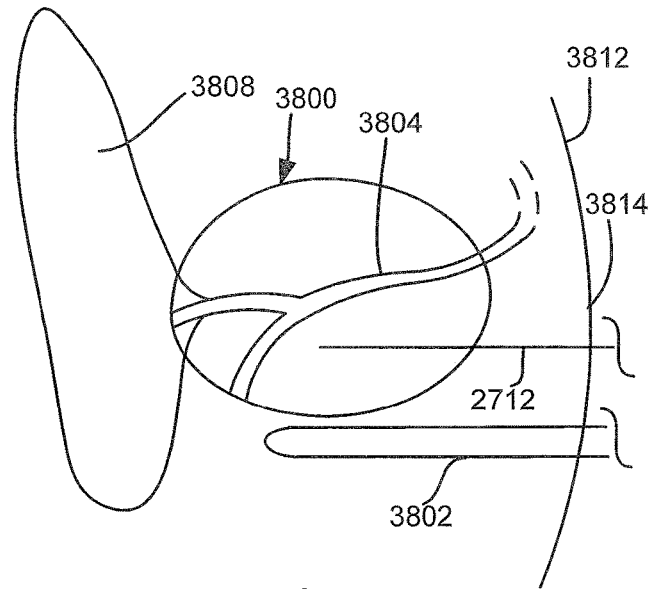
FIG. 38B is a sagittal plane or slice view of the prostate depicting the urethra and an access site for penetration of the access needle.

As described previously, the probe or transducer provides imaging in axial and sagittal planes so as to provide real-time images of the prostate. As seen in FIG. 38A, which is a transverse plane showing the prostate 3800 and the probe 3802, the urethra 3804 is shown, as well as a path 3806 of the urethra 3804, as would be seen in a sagittal plane. As seen in FIG. 38B, which is a sagittal plane showing the prostate 3800 and the probe 3802, the urethra 3804 is shown extending over the prostate 3800 and connecting with the bladder 3808.

When the prostate is viewed, as seen in FIGS. 38A and 38B, the physician may then position the access needle 2712 in an access site 3810 in the subcutaneous tissue 3812 of the perineum 3814, where the access site 3810 is at a midpoint between a lateral edge of the prostate 3816 and the urethral path 3806 along a first axis and a midpoint between an anterior capsule 3818 and a posterior capsule 3820 along a second axis. The physician may guide the probe 3802 and the biopsy guide (not shown) along a sagittal plane to the target using the real-time image from the probe 3802, and the physician may obtain one or more specimens 3822 of the prostate 3800 through the access needle 2712 being guided by the biopsy guide.

Figure 38C:
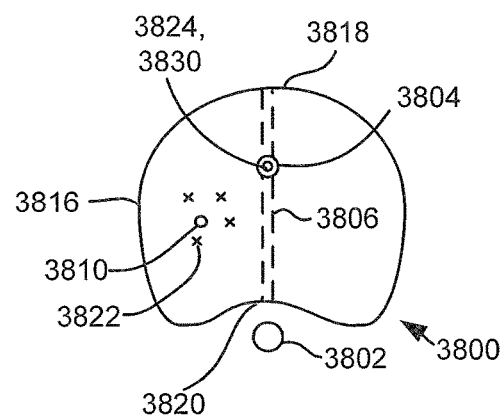
FIG. 38C is the same transverse plane or slice view as FIG. 38A, but including a marking device positioned within the urethra for biopsy navigation.
Figure 38D:
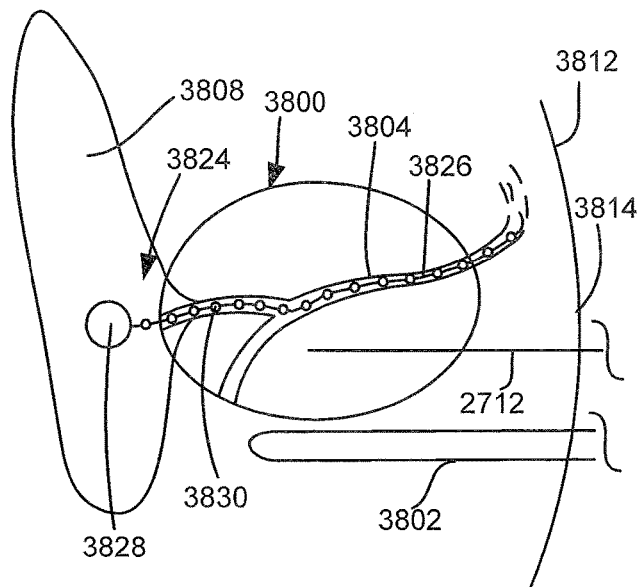
FIG. 38D is the same sagittal plane or slice view as FIG. 38B, but including a marking device positioned within the urethra for biopsy navigation.

Identifying the urethra may be accomplished via a number of methods. First, as seen in FIGS. 38C-38D, a marking device 3824 such as, for example, a balloon catheter can be inserted into the urethra 3804 and used by the physician to locate the urethra 3804. As seen in FIG. 38C-38D, the marking device 3824 may include a catheter 3826 and a balloon 3828. The balloon 3828 may be expanded in the bladder 3808 and the catheter 3826 may extend through the urethra 3804 and out of the patient's body. The balloon 3828 and/or catheter 3826 may be visible in certain planes during the biopsy procedure and may aid in identifying the urethra 3804.

Additionally or alternatively, the marking device 3824 may include markers 3830 such as physical or chemical markers that are visible in an ultrasound environment (e.g., pellets of polylactic and polyglycolic acids containing carbon dioxide, polyglycolic acid pads) along the length of the catheter 3826 so that the physician can view the path of the urethra 3804 as viewed in transverse or sagittal planes. Thus, the physician may be able to position a trajectory of the access needle 2712 to be adjacent and not intersecting with the path of the urethra as indicated by the markers 3830 on the catheter 3826. The markers 3830 may be positioned on the catheter at certain intervals so as to provide a way to estimate the size or volume of the prostate 3800. Additionally or alternatively, the catheter 3826 may include a contrast medium (e.g., dye) for visualization purposes and may otherwise function similarly to markers 3830 positioned on the catheter 3826.

The biopsy guides and devices described herein may additionally include markers or sensors positioned on the biopsy guide or access needle such that movement of the guide or needle, or any device/material placed through the access needle, may be visualized via the markers/sensors by ultrasound equipment (e.g., probe) or other equipment using different imaging modalities (e.g., MRI, CT). In this way, for example, a marker positioned at a distal end of the access needle may provide visual guidance as to the location of the tip of the access needle relative to the boundaries of the prostate.

Although various representative implementations have been described above with a certain degree of particularity, those skilled in the art could make numerous alterations to the disclosed embodiments without departing from the spirit or scope of the inventive subject matter set forth in the specification. All directional references (e.g., distal, proximal, front, back, side, top, bottom, fore, aft, right, left, etc.) are only used for identification purposes to aid the reader's understanding of the implementations, and do not create limitations, particularly as to the position, orientation, or use of the embodiments described herein unless specifically set forth in the claims. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A method of performing a transperineal biopsy procedure on a prostate of a patient using a transrectal ultrasound probe configured to provide imaging, the patient comprising a perineal access site leading to the prostate, the method comprising:
    imaging the prostate of the patient with the transrectal ultrasound probe, wherein a transperineal biopsy guide is coupled to the transrectal ultrasound probe, the transperineal biopsy guide comprising a mount coupled to the transrectal ultrasound probe, a guide member coupled to the mount and including a rail receiving channel extending a first length between a proximal end and a distal end of the rail receiving channel, and a displacement member including a rail member extending a second length between a proximal end and a distal end of the rail member and a vertically extending member extending from the distal end of the rail member, the vertically extending member including a plurality of needle receiving ports, wherein the rail receiving channel is positioned generally parallel with a longitudinal axis of the transrectal ultrasound probe;
    sliding the rail member within the rail receiving channel so as to position the vertically extending member of the displacement member adjacent the perineal access site of the patient;
    inserting an access needle into the perineal access site of the patient, the access needle supported by one of the plurality of needle receiving ports; and
    inserting a needle through the access needle and into a first location of the prostate of the patient.

2. The method of claim 1, further comprising: contacting a distal end of a pair of guide rails of the guide member with the perineal access site of the patient, the pair of guide rails being spaced apart from each other and positioned on opposite sides of the rail receiving channel.

3. The method of claim 1, further comprising injecting a substance into the patient via the needle.

4. The method of claim 1, further comprising taking a first biopsy of the first location of the prostate of the patient via the needle.

5. The method of claim 4, further comprising taking a second biopsy of a second location of the prostate of the patient via the needle, the second location being different than the first location.

6. The method of claim 5, wherein the access needle remains positioned within the perineal access site of the patient for the first biopsy and the second biopsy.

7. The method of claim 1, wherein the displacement member includes an end plate coupled to the proximal end of the rail member, the end plate configured to contact a proximal end of the guide member in order to limit displacement of the displacement member relative to the guide member.

8. The method of claim 1, wherein the plurality of needle receiving ports comprises at least five needle receiving ports oriented vertically relative to the rail member.

9. The method of claim 1, further comprising engaging a portion of the guide member to the perineal access site of the patient prior to inserting the access needle into the perineal access site of the patient.

10. The method of claim 1, wherein the access needle has a needle size of 14 gauge, 15 gauge, or 16 gauge.

11. The method of claim 10, wherein the needle is a biopsy needle with a needle size of 18 gauge.

12. The method of claim 1, wherein the needle is a biopsy needle with a needle size of 18 gauge.

13. The method of claim 1, further comprising securing the access needle to the one of the plurality of needle receiving ports such that movement of the access needle relative to the vertically extending member is restrained.

14. The method of claim 13, wherein the access needle and the plurality of needle receiving ports including corresponding features that restrain relative movement when secured together.

15. The method of claim 1, wherein the mount includes a releasable fastener, and wherein a distal portion of the guide member is offset from the releasable fastener of the mount.

16. A method of performing a transperineal biopsy procedure on a prostate of a patient using a transrectal ultrasound probe configured to provide imaging, the patient comprising a perineal access site leading to the prostate, the method comprising:
    imaging the prostate of the patient with the transrectal ultrasound probe, wherein a transperineal biopsy guide is coupled to the transrectal ultrasound probe, the transperineal biopsy guide comprising a mount coupled to the transrectal ultrasound probe, a guide member coupled to the mount and including a rail receiving channel extending a first length between a proximal end and a distal end of the rail receiving channel, and a displacement member including a rail member extending a second length between a proximal end and a distal end of the rail member and being positioned within the rail receiving channel of the guide member and a vertically extending member extending from the distal end of the rail member, the vertically extending member including a plurality of needle receiving ports, the guide member further including a pair of stabilization members extending away from the rail receiving channel;

positioning the vertically extending member of the displacement member adjacent the perineal access site of the patient;

inserting an access needle into the perineal access site of the patient, the access needle supported by one of the plurality of needle receiving ports; and inserting a needle through the access needle and into a first location of the prostate of the patient.

17. The method of claim 16, further comprising: contacting a distal end of the pair of stabilization members of the guide member with the perineal access site of the patient, the pair of stabilization members being spaced apart from each other and positioned on opposite sides of the rail receiving channel.

18. The method of claim 16, further comprising injecting a substance into the patient via the needle.

19. The method of claim 16, further comprising taking a first biopsy of the first location of the prostate of the patient via the needle.

20. The method of claim 19, further comprising taking a second biopsy of a second location of the prostate of the patient via the needle, the second location being different than the first location.

21. The method of claim 20, wherein the access needle remains positioned within the perineal access site of the patient for the first biopsy and the second biopsy.

22. The method of claim 16, wherein the rail receiving channel is positioned generally parallel with a longitudinal axis of the transrectal ultrasound probe.

23. The method of claim 16, wherein the displacement member includes an end plate coupled to the proximal end of the rail member, the end plate configured to contact a proximal end of the guide member in order to limit displacement of the displacement member relative to the guide member.

24. The method of claim 16, wherein the plurality of needle receiving ports comprises at least five needle receiving ports oriented vertically relative to the rail member.

25. The method of claim 16, further comprising engaging a portion of the guide member to the perineal access site of the patient prior to inserting the access needle into the perineal access site of the patient.

26. The method of claim 16, wherein the access needle has a needle size of 14 gauge, 15 gauge, or 16 gauge.

27. The method of claim 26, wherein the needle is a biopsy needle with a needle size of 18 gauge.

28. The method of claim 16, wherein the needle is a biopsy needle with a needle size of 18 gauge.

29. The method of claim 16, further comprising securing the access needle to the one of the plurality of needle receiving ports such that movement of the access needle relative to the vertically extending member is restrained.

30. The method of claim 29, wherein the access needle and the plurality of needle receiving ports including corresponding features that restrain relative movement when secured together.

* * * * *

EX PARTE REEXAMINATION CERTIFICATE (13048th)
United States Patent
Allaway

(10) Number: US 11,446,056 C1
(45) Certificate Issued: Oct. 2, 2025

(54) TRANSPERINEAL PROSTATE BIOPSY DEVICE, SYSTEMS, AND METHODS OF USE

(71) Applicant: Corbin Clinical Resources, LLC, Cumberland, MD (US)

(72) Inventor: Matthew J. Allaway, Cumberland, MD (US)

(73) Assignee: CORBIN CLINICAL RESOURCES, LLC, Cumberland, MD (US)

Reexamination Request:
No. 90/019,257, Sep. 22, 2023

Reexamination Certificate for:
Patent No.: 11,446,056
Issued: Sep. 20, 2022
Appl. No.: 17/494,962
Filed: Oct. 6, 2021

Related U.S. Application Data

(63) Continuation-in-part of application No. 17/314,845, filed on May 7, 2021, now Pat. No. 11,246,677,
(Continued)

(51) Int. Cl.
| | |
|---|---|
| *A61B 90/00* | (2016.01) |
| *A61B 8/08* | (2006.01) |
| *A61B 8/12* | (2006.01) |
| *A61B 10/02* | (2006.01) |
| *A61B 10/04* | (2006.01) |
| *A61B 17/34* | (2006.01) |
| *A61B 17/00* | (2006.01) |
| *A61B 18/00* | (2006.01) |
| *A61B 18/02* | (2006.01) |
| *A61B 18/12* | (2006.01) |

(52) U.S. Cl.
CPC ........ *A61B 17/3403* (2013.01); *A61B 8/0841* (2013.01); *A61B 8/12* (2013.01); *A61B 10/0241* (2013.01); *A61B 10/04* (2013.01); *A61B 90/39* (2016.02); *A61B 2010/045* (2013.01); *A61B 2017/00274* (2013.01); *A61B 2017/00477* (2013.01); *A61B 2017/3405* (2013.01); *A61B 2017/3411* (2013.01); *A61B 2017/3413* (2013.01); *A61B 2018/00547* (2013.01); *A61B 18/02* (2013.01); *A61B 18/12* (2013.01); *A61B 2090/3925* (2016.02); *A61B 2090/3933* (2016.02); *A61B 2090/3954* (2016.02); *A61B 2090/3966* (2016.02)

(58) Field of Classification Search
None
See application file for complete search history.

(56) References Cited

To view the complete listing of prior art documents cited during the proceeding for Reexamination Control Number 90/019,257, please refer to the USPTO's Patent Electronic System.

*Primary Examiner* — Catherine S Williams

(57) ABSTRACT

A method of performing a transperineal biopsy procedure includes imaging the prostate with a transrectal ultrasound probe with a transperineal biopsy guide coupled to the probe. The transperineal biopsy guide including a mount coupled to the probe, a guide member coupled to the mount and including a rail receiving channel extending a first length, and a displacement member including a rail member extending a second length between a proximal end and a distal end, and a vertically extending member coupled to the distal end of the rail member. The vertically extending member including a plurality of needle receiving ports. The method further includes sliding the rail member within the rail receiving channel. The method further includes inserting an access needle into the perineal access site of the patient and inserting a needle through the access needle and into a first location of the prostate of the patient.

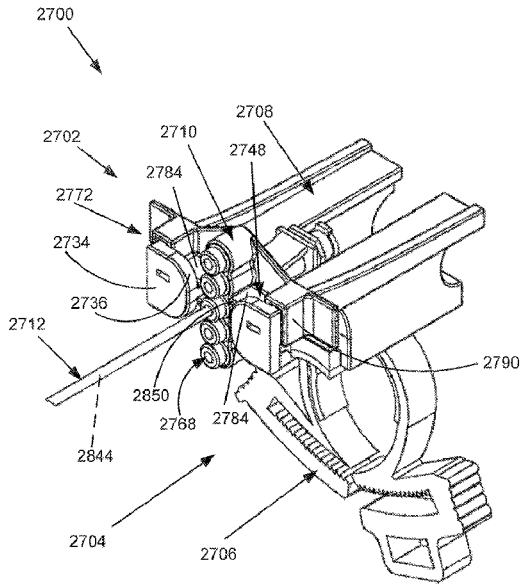

Related U.S. Application Data which is a continuation of application No. 16/115,180, filed on Aug. 28, 2018, now Pat. No. 11,096,762, which is a continuation of application No. 14/677,286, filed on Apr. 2, 2015, now Pat. No. 10,064,681, said application No. 17/494,962 is a continuation-in-part of application No. 16/991,150, filed on Aug. 12, 2020, now Pat. No. 11,583,310, which is a continuation of application No. 14/874,104, filed on Oct. 2, 2015, now Pat. No. 10,743,909, which is a continuation-in-part of application No. 14/677,286, filed on Apr. 2, 2015, now Pat. No. 10,064,681.

(60) Provisional application No. 61/974,826, filed on Apr. 3, 2014.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1, 4-6 and 10-13 is confirmed.

New claims 31-34 are added and determined to be patentable.

Claims 2-3, 7-9 and 14-30 were not reexamined.

*31. The method of claim 13, wherein the access needle is secured to the one of the plurality of needle receiving ports such that rotational movement of the access needle relative to the vertically extending member is restrained.*

*32. The method of claim 31, wherein the one of the plurality of needle receiving ports is a hole extending through the vertically extending member.*

*33. A method of performing a transperineal biopsy procedure on a prostate of a patient using a transrectal ultrasound probe configured to provide imaging, the patient comprising a perineal access site leading to the prostate, the method comprising:*

*imaging the prostate of the patient with the transrectal ultrasound probe, wherein a transperineal biopsy guide is coupled to the transrectal ultrasound probe, the transperineal biopsy guide comprising a mount coupled to the transrectal ultrasound probe, a guide member coupled to the mount and including a rail receiving channel extending a first length between a proximal end and a distal end of the rail receiving channel, and a displacement member including a rail member extending a second length between a proximal end and a distal end of the rail member and a vertically extending member extending from the distal end of the rail member, the vertically extending member including a plurality of needle receiving ports, wherein the rail receiving channel is positioned generally parallel with a longitudinal axis of the transrectal ultrasound probe;*

*sliding the rail member within the rail receiving channel so as to position the vertically extending member of the displacement member adjacent the perineal access site of the patient;*

*inserting an access needle into the perineal access site of the patient, the access needle supported by one of the plurality of needle receiving ports;*

*inserting a needle through the access needle and into a first location of the prostate of the patient; and*

*wherein the access needle is secured to the one of the plurality of needle receiving ports.*

*34. The method of claim 33, wherein the one of the plurality of needle receiving ports is a hole extending through the vertically extending member.*

\* \* \* \* \*